(12) United States Patent  (10) Patent No.: US 9,070,885 B2
Ono  (45) Date of Patent: Jun. 30, 2015

(54) ANTHRACENE COMPOUND AND ORGANIC ELECTROLUMINESCENCE ELEMENT USING SAME

(75) Inventor: Yohei Ono, Chiba (JP)

(73) Assignee: JNC CORPORATION, Tokyo (JP)

( * ) Notice: Subject to any disclaimer, the term of this patent is extended or adjusted under 35 U.S.C. 154(b) by 67 days.

(21) Appl. No.: 13/980,177

(22) PCT Filed: Jan. 26, 2012

(86) PCT No.: PCT/JP2012/051640
§ 371 (c)(1),
(2), (4) Date: Jul. 17, 2013

(87) PCT Pub. No.: WO2012/102333
PCT Pub. Date: Aug. 2, 2012

(65) Prior Publication Data
US 2013/0292665 A1    Nov. 7, 2013

(30) Foreign Application Priority Data

Jan. 27, 2011 (JP) .................................. 2011-015702

(51) Int. Cl.
*H01L 51/50* (2006.01)
*H01L 51/00* (2006.01)
*C09K 11/06* (2006.01)
*H05B 33/14* (2006.01)
(Continued)

(52) U.S. Cl.
CPC ............ *H01L 51/0058* (2013.01); *C09K 11/06* (2013.01); *C09K 2211/1007* (2013.01); *C09K 2211/1011* (2013.01); *H01L 51/5012* (2013.01); *H05B 33/14* (2013.01); *C07B 2200/05* (2013.01); *C07C 15/28* (2013.01); *C07C 15/30* (2013.01); *C07C 15/38* (2013.01); *H01L 51/0054* (2013.01); *C07C 2103/24* (2013.01); *C07C 2103/26* (2013.01); *C07C 2103/42* (2013.01); *C07C 2103/48* (2013.01); *C07F 7/0818* (2013.01)

(58) Field of Classification Search
None
See application file for complete search history.

(56) References Cited

U.S. PATENT DOCUMENTS

2005/0275341 A1   12/2005   Satsuki et al.
2006/0014046 A1    1/2006   Wang et al.
(Continued)

FOREIGN PATENT DOCUMENTS

CN   103313958   9/2013
JP   2004-6222    1/2004
(Continued)

OTHER PUBLICATIONS

International Search Report issued Mar. 6, 2012 in International (PCT) Application No. PCT/JP2012/051640.
(Continued)

*Primary Examiner* — Gregory Clark
(74) *Attorney, Agent, or Firm* — Wenderoth, Lind & Ponack, L.L.P.

(57) ABSTRACT

Provided is an organic electroluminescence element having superior element service life. An anthracene compound in which an aryl group having C10 or greater is bonded to the 9-position and a naphthyl group is bonded to the 10-position, wherein a compound in which a specific aryl group has been substituted, in particular, at the 7-position of the naphthyl group (which is bonded at the 2-position thereof to the anthracene) is used as a material for a luminescence layer to produce the organic electroluminescence element.

14 Claims, 1 Drawing Sheet

(51) Int. Cl.
*C07C 15/28* (2006.01)
*C07C 15/30* (2006.01)
*C07C 15/38* (2006.01)
*C07F 7/08* (2006.01)

(56) References Cited

U.S. PATENT DOCUMENTS

| | | |
|---|---|---|
| 2007/0152565 A1 | 7/2007 | Kubota et al. |
| 2007/0212568 A1 | 9/2007 | Wang |
| 2008/0206447 A1 | 8/2008 | Inoue et al. |
| 2009/0189521 A1 | 7/2009 | Chun et al. |
| 2009/0206740 A1 | 8/2009 | Chun et al. |
| 2009/0230855 A1 | 9/2009 | Kim et al. |
| 2011/0057173 A1* | 3/2011 | LeCloux et al. ............. 257/40 |
| 2011/0175079 A1 | 7/2011 | Yokoyama et al. |
| 2011/0220886 A1 | 9/2011 | Takeshima et al. |
| 2013/0300638 A1 | 11/2013 | Kamatani et al. |

FOREIGN PATENT DOCUMENTS

| | | |
|---|---|---|
| JP | 2005-139390 | 6/2005 |
| JP | 2007-299980 | 11/2007 |
| JP | 2009-33146 | 2/2009 |
| JP | 2009-177128 | 8/2009 |
| KR | 10-2009-0052774 | 5/2009 |
| KR | 10-2009-0107209 | 10/2009 |
| KR | 10-2011-0076376 | 7/2011 |
| WO | 2010/032447 | 3/2010 |
| WO | 2010/035723 | 4/2010 |
| WO | 2010/052885 | 5/2010 |
| WO | 2010/099534 | 9/2010 |
| WO | 2010/114256 | 10/2010 |
| WO | 2010/137678 | 12/2010 |

OTHER PUBLICATIONS

Hung et al., "Recent progress of molecular organic electroluminescent materials and devices", Materials Science and Engineering R 39, 2002, pp. 143-222.
Kim et al., "A stable blue host material for organic light-emitting diodes", Applied Physics Letters, vol. 91, 251111-1-251111-3, 2007.
Ho et al., "Highly efficient deep blue organic electroluminescent device based on 1-methyl-9,10-di(1-napthyl)anthracene", Applied Physics Letters, vol. 89, 252903-1-252903-3, 2006.
Gao et al., "High-efficiency deep blue host for organic light-emitting devices", Applied Physics Letter, vol. 90, 123506-1-123506-3, 2007.
Ho et al., "Efficient deep blue emitters for organic electroluminescent devices", Applied Physics Letters, vol. 91, 083515-1-083515-3, 2007.
Chinese Office Action issue Jul. 28, 2014 in corresponding Chinese Application No. 2012800056203.

* cited by examiner

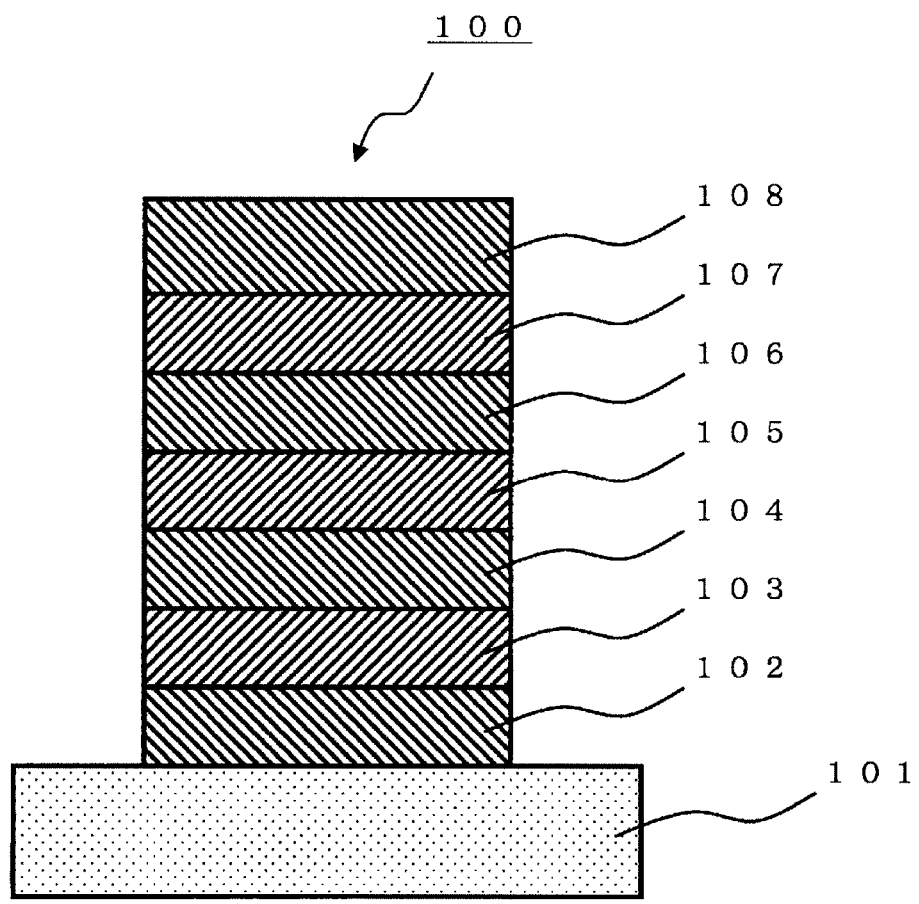

ANTHRACENE COMPOUND AND ORGANIC ELECTROLUMINESCENCE ELEMENT USING SAME

TECHNICAL FIELD

The present invention relates to a novel anthracene compound, a novel anthracene light emitting layer material, and an organic electroluminescence element suitable as a display element of a display device such as a color display. More specifically, it relates to an organic electroluminescence element having improved service life or the like by using a novel anthracene compound in a light emitting layer (hereinafter, it may be abbreviated as an "organic EL element" or simply as an "element").

BACKGROUND ART

An organic EL element is a self luminous type light emitting element and is expected as a light emitting element for display or lighting, and studies are made actively in recent years. To promote commercialization of an organic EL element, low power consumption and long service life of the element are an essential point, and they are especially a big issue in a blue light emitting element.

For such reasons, various consideration have been made with regard to an organic light emitting material, and for the purpose of improving light emission efficiency and service life of a blue light emitting element, improvement of styrylallene or anthracene derivatives has been made (for example, Non-Patent Document 1, and Patent Documents 1 and 2). Further, as development of a material for display is accelerated, a material having a constitution enabling obtainment of blue light emission with high color purity (short wavelength and narrow full width at half maximum in light emission spectrum) is in demand for the improvement of NTSC ratio.

Until now, as a light emitting layer material of a blue element, anthracene derivatives have been reported (Patent Documents 1 and 2 and Non-Patent Documents 1 to 5 described below). However, when a light emitting layer is formed by using a material with short emission wavelength for the purpose of having light emission with high color purity, it was difficult to improve a service life property of an organic EL element with high light emission efficiency.

CITATION LIST

Patent Literature

Patent Literature 1: Japanese Patent Application Laid-Open (JP-A) No 2005-139390
Patent Document 2: JP-A No. 2004-6222

Non-Patent Literature

Non-Patent Literature 1: Materials Science and Engineering: R: Reports Volume 39, Issues 5-6, Pages 143-222, 2002.
Non-Patent Literature 2: Appl. Phys. Lett. 91, 251111 (2007)
Non-Patent Literature 3: Appl. Phys. Lett. 89, 252903 (2006)
Non-Patent Literature 4: Appl. Phys. Lett. 90, 123506 (2007)
Non-Patent Literature 5: Appl. Phys. Lett. 91, 083515 (2007)

SUMMARY OF INVENTION

Technical Problem

Under the circumstances, the development of a blue light emitting element with high color purity and improved element service life or the like and a display device using it is needed.

Solution to Problem

Inventors of the present invention conducted intensive studies to solve the problems, and as a result, developed a novel anthracene compound represented by Formula (1), and found that an organic electroluminescence element having improved element service life or the like can be obtained by using the compound as a light emitting layer material used for light emitting layer of a blue light emitting element. The invention is completed accordingly.

Specifically, the invention provides a novel anthracene compound, a light emitting layer material, an organic electroluminescence element, and a display device and a lighting device including the organic electroluminescence element as described below.

[1] A compound represented by the following Formula (1).

[Formula 5]

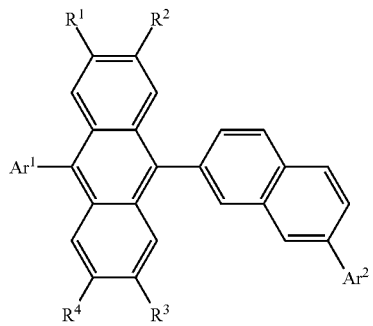

(1)

In formula (1),
$Ar^1$ is an aryl having 10-30 carbon atoms which may be substituted,
$Ar^2$ is an aryl having 6-30 carbon atoms which may be substituted,
$R^1$-$R^4$ are, each independently, a hydrogen or an alkyl having 1-4 carbon atoms, and
at least one hydrogen in the compound represented by the formula (1) may be substituted with deuterium.

[2] The compound described in the above [1], in which $Ar^1$ is naphthyl, biphenylyl, binaphthyl, terphenylyl, quaterphenylyl, naphthylphenyl, phenylnaphthyl, phenanthryl, phenanthrylphenyl, chrysenyl, pyrenylphenyl, or triphenylenyl, which may be substituted with alkyl having 1-12 carbon atoms, or cycloalkyl having 3-12 carbon atoms,
$Ar^2$ is phenyl, naphthyl, biphenylyl, binaphthyl, terphenylyl, quaterphenylyl, naphthylphenyl, phenylnaphthyl, phenanthryl, phenanthrylphenyl, chrysenyl, pyrenylphenyl, or triphenylenyl, which may be substituted with alkyl having 1-12 carbon atoms, or cycloalkyl having 3-12 carbon atoms,
$R^1$-$R^4$ are, each independently, hydrogen, methyl, isopropyl, or t-butyl, and
at least one hydrogen in compounds represented by the formula (1) may be substituted with deuterium.

[3] The compound described in the above [1] or [2], in which
Ar¹ is 1-naphthyl, 2-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl,
Ar² is phenyl, 1-naphthyl, 2-naphthyl, 2-biphenylyl, 3-biphenylyl, 4-biphenylyl, m-terphenyl-5'-yl, 4-(naphthalene-1-yl)phenyl, 4-(naphthalene-2-yl)phenyl, phenanthrene-9-yl or triphenylene-2-yl,
$R^1$-$R^4$ are hydrogen, and
at least one hydrogen in the compound represented by the formula (1) may be substituted with deuterium.

[4] The compound described in the above [3], in which Ar¹ is 1-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl, and
at least one hydrogen in Ar² may be substituted with deuterium.

[5] The compound represented by the following formula (1-2).

[Formula 6]

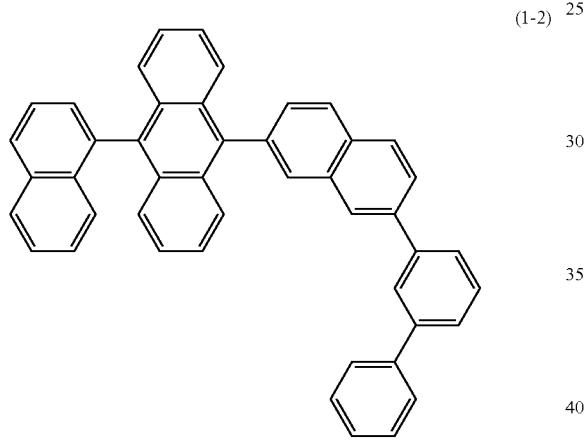

(1-2)

[6] Compounds represented by the following formula (1-1), formula (1-21), formula (1-34), formula (1-38), formula (1-117), or formula (1-129).

[Formula 7]

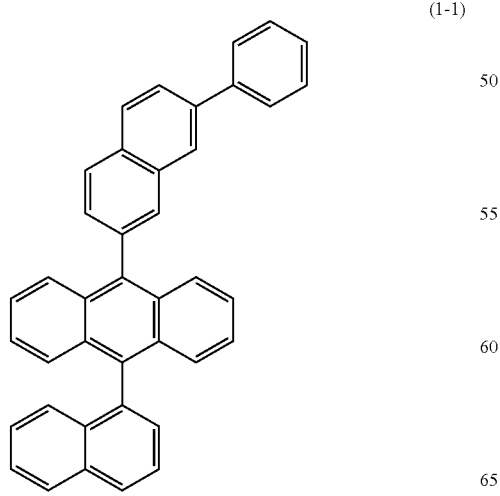

(1-1)

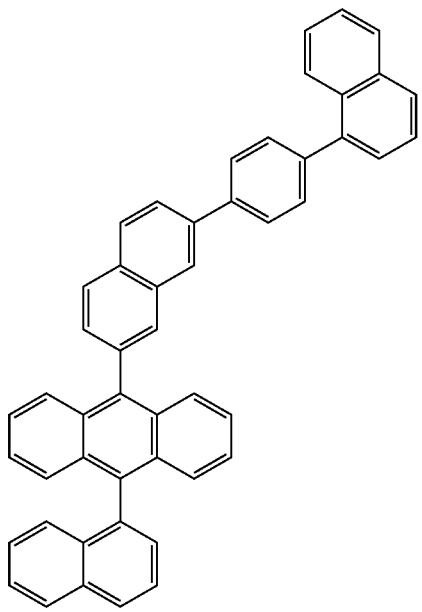

(1-21)

-continued

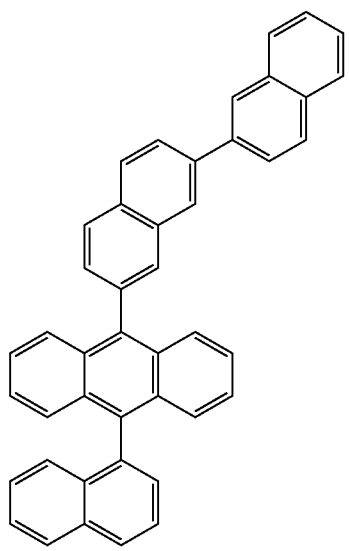

(1-34)

(1-38)
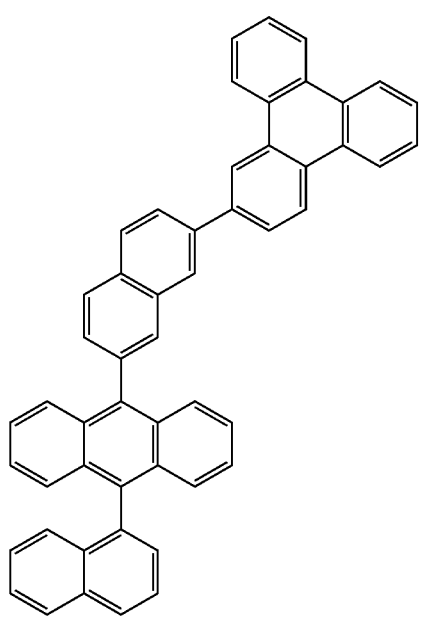
(1-129)
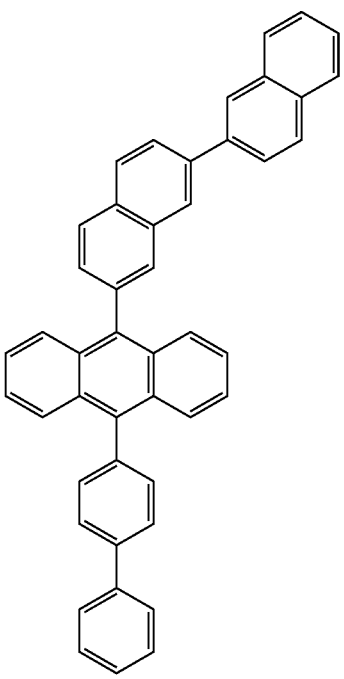
[7] Compounds represented by the following formula (1-160), formula (1-162), formula (1-164), formula (1-166), formula (1-172), or the formula (1-184).
[Formula 8]
(1-117)
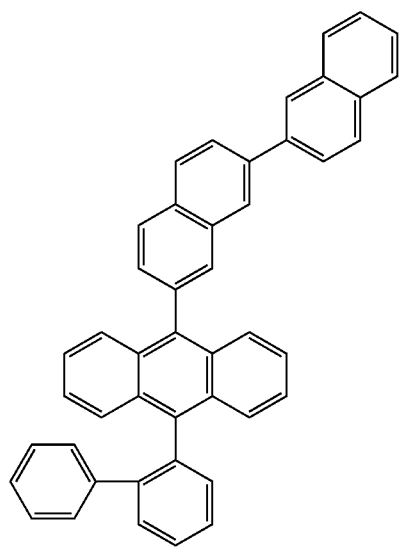
(1-160)
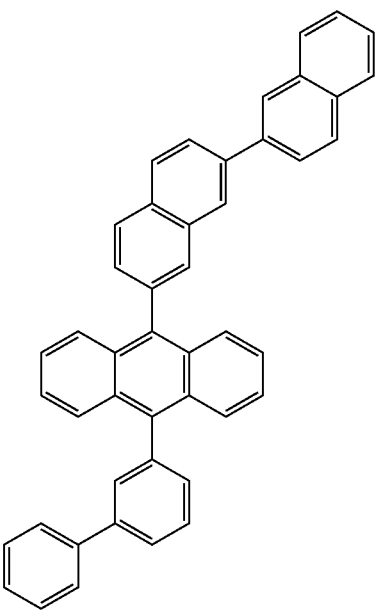

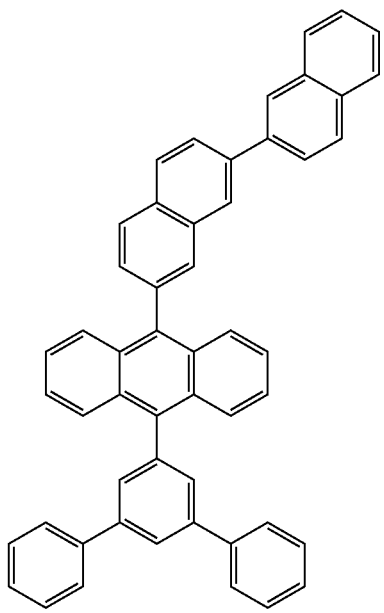
(1-162)
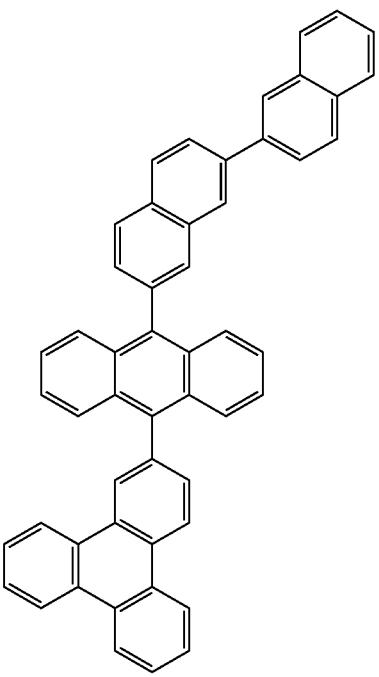
(1-166)
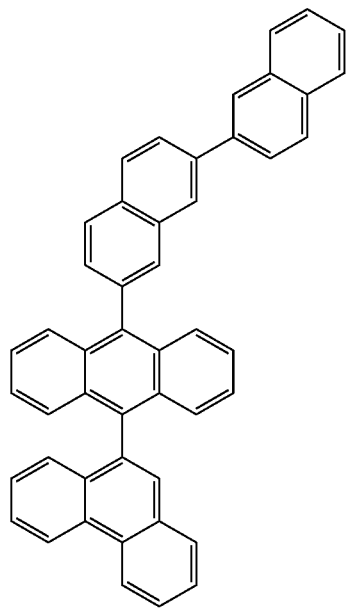
(1-164)
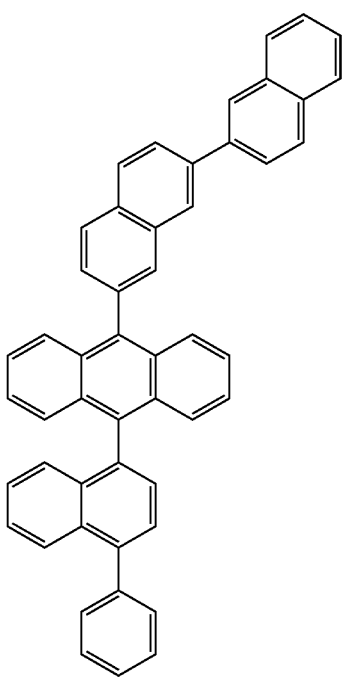
(1-172)

(1-184)

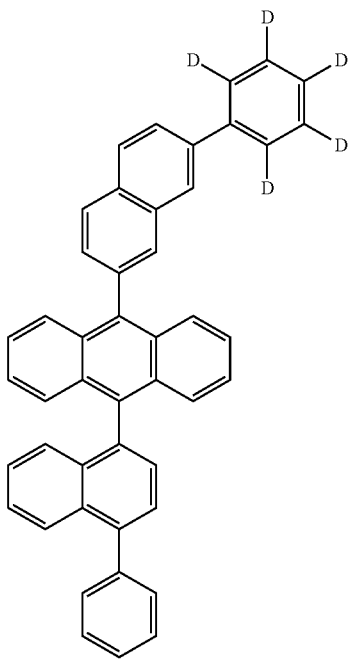

[8] A light emitting layer material represented by the compound described in any one of the above [1] to [7].

[9] An organic electroluminescence element having a pair of electrodes consisting of a positive electrode and a negative electrode and a light emitting layer containing the light emitting layer material described in the above [8] as disposed between the pair of electrodes.

[10] The organic electroluminescence element described in the above [9], which has in the light emitting layer at least one selected from the group consisting of amine with a stilbene structure, an aromatic amine derivative, and a coumarin derivative.

[11] The organic electroluminescence element described in the above [9] or [10], which has an electron transport layer and/or an electron injection layer disposed between the negative electrode and the light emitting layer, in which at least one of the electron transport layer and the electron injection layer contains at least one selected from the group consisting of a quinolinol-based metal complex, a pyridine derivative, a phenanthroline derivative, a borane derivative, and a benzimidazole derivative.

[12] The organic electroluminescence element described in the above [11], in which at least one of the electron transport layer and the electron injection layer also contains at least one selected from the group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal.

[13] A display device having the organic electroluminescence element described in any one of the above [9] to [12].

[14] A lighting device having the organic electroluminescence element described in any one of the above [9] to [12].

Advantageous Effects of Invention

According to a preferred embodiment of the invention, an organic electroluminescence element having long element service life can be provided. In particular, as a blue light emitting element with high color purity, it can solve the problems of related art. Further, a display device, a lighting device, or the like which has the effective organic electroluminescence element can be provided.

BRIEF DESCRIPTION OF DRAWING

FIG. 1 is a schematic cross-sectional view illustrating an organic electroluminescence element according to the present embodiment.

DESCRIPTION OF EMBODIMENTS

1. Anthracene Compound Represented by Formula (1)

First, an anthracene compound represented by Formula (1) will be described in detail. The compound of the invention is an anthracene compound in which an aryl having 10 or more carbon atoms is bonded to the 9-position and a naphthyl group is bonded to the 10-position, in which a specific aryl is substituted, in particular, at the 7-position of the naphthyl group (which is bonded at the 2-position thereof to the anthracene), and by selecting such substitution position and aryl structure, it becomes a compound having excellent element service life as a light emitting layer material.

As "aryl having 10-30 carbon atoms" in $Ar^1$ of the formula (1), aryl having 10-18 carbon atoms is preferable. As "aryl having 6-30 carbon atoms" in $Ar^2$, aryl having 6-20 carbon atoms is preferable.

Specific examples of "aryl" include: monocyclic aryl, that is, phenyl; bicyclic aryl, that is, (2-,3-,4-)biphenylyl; condensed bicyclic aryl, that is, (1-,2-)naphthyl; tricyclic aryl, that is, terphenylyl(m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, and p-terphenyl-4-yl); condensed tricyclic aryl, that is, acenaphthylene(1-,3-,4-,5-)yl, fluorene-(1-,2-,3-,4-,9-)yl, phenalene-(1-,2-)yl, and (1-,2-,3-,4-,9-)phenanthryl; tetracyclic aryl, that is, quaterphenylyl(5'-phenyl-m-terphenyl-2-yl, 5'-phenyl-m-terphenyl-3-yl, 5'-phenyl-m-terphenyl-4-yl, and m-quaterphenyl); condensed tetracyclic aryl, that is, triphenylene-(1-,2-)yl, pyrene-(1-,2-,4-)yl, and naphthacene(1-,2-,5-)yl; condensed pentacyclic aryl, that is, perylene(1-,2-,3-)yl, pentacene-(1-,2-,5-,6-)yl and 4-(naphthalene-1-,-2-yl)phenyl, 3-(naphthalene-1-,-2-yl)phenyl, 4-phenylnaphthalene-1-yl, 1,1'-binaphthalene-4-yl, 4-(phenanthrene-9-yl)phenyl, and the like, which are obtained from combination of those aryls. However, phenyl is not chosen as $Ar^1$.

Among the examples indicated above, as $Ar^1$, 1-naphthyl, 2-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl is preferable, and 1-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl is particularly preferable. As $Ar^2$, phenyl, 1-naphthyl, 2-naphthyl, 2-biphenylyl, 3-biphenylyl, 4-biphenylyl, m-terphenyl-5'-yl, 4-(naphthalene-1-yl)phenyl, 4-(naphthalene-2-yl)phenyl, and phenanthrene-9-yl or triphenylene-2-yl is preferable.

The substituent of the "aryl" is not particularly limited if high light emission efficiency and excellent element service life are obtained. Preferred examples thereof include alkyl having 1 to 12 carbon atoms, cycloalkyl having 3 to 12 carbon atoms, or fluorine.

The "alkyl having 1-12 carbon atoms" as a substituent is either a straight chain or a branched chain. That is, the alkyl is a straight chain alkyl having 1-12 carbon atoms, or a branched chain alkyl having 3-12 carbon atoms. More preferably, the alkyl is alkyl having 1-6 carbon atoms (branched chain alkyl having 3-6 carbon atoms), and still more preferably, alkyl having 1-4 carbon atoms (branched chain alkyl having 3-4 carbon atoms). Specific examples of the alkyl includes methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, or 2-ethylbutyl, preferably, methyl, ethyl, n-propyl, isopropyl, n-butyl, isobutyl, s-butyl, or t-butyl, and more preferably, methyl, isopropyl, or t-butyl.

Specific examples of the "cycloalkyl having 3-12 carbon atoms" as a substituent include cyclopropyl, cyclobutyl, cyclopentyl, cyclohexyl, methyl cyclopentyl, cycloheptyl, methylcyclohexyl, cyclooctyl, or dimethylcyclohexyl.

As for the substituent of the "aryl", it is preferably non-substituted. However, if a substituent is present, the number of the substituent is a number falling within the maximum substitutable number, for example, and it is preferably 1 to 3, more preferably 1 to 2, and still more preferably 1.

As for the "alkyl having 1 to 4 carbon atoms" for $R^1$ to $R^4$ in Formula (1), descriptions of the alkyl as a substituent for aryl described above can be cited. It is preferable that $R^1$ to $R^4$ be each independently hydrogen, methyl, isopropyl, or t-butyl. Hydrogen is more preferable.

Further, part or all of the hydrogen atoms of the anthracene skeleton for constituting the compound represented by Formula (1), the hydrogen atoms of $Ar^1$ or the naphthyl group substituted at the 9-position or the 10-position of anthracene, or the hydrogen atoms of $Ar^2$ or $R^1$ to $R^4$ may be a deuterium.

Specific examples of compounds represented by the above-mentioned formula (1) include compounds represented by the following formulae (1-1) to (1-159) and compounds represented by the following formulae (1-160) to (1-184). Among the following compounds, those represented by the following formulae (1-1) to (1-4), formula (1-19), formula (1-21), formula (1-26), formula (1-27), formula (1-30), formula (1-34), formula (1-37), formula (1-38), formulae (1-40) to (1-43), formula (1-46), formula (1-47), formulae (1-50) to (1-53), formulae (1-55) to (1-58), formula (1-61), formula (1-62), formulae (1-65) to (1-68), formulae (1-70) to (1-73), formula (1-76), formula (1-77), formulae (1-80) to (1-83), formulae (1-85) to (1-88), formula (1-91), formula (1-92), and formulae (1-95) to (1-98) is preferable. Compounds represented by the formula (1-112), the formula (1-113), the formula (1-116), the formula (1-117), the formula (1-119), the formula (1-122), the formula (1-124), the formula (1-125), the formula (1-128), the formula (1-129), the formula (1-131), the formula (1-134), the formula (1-160), the formula (1-162), the formula (1-164), the formula (1-166), the formula (1-168), the formula (1-169), the formulae (1-172) to (1-174), and the formulae (1-176) to (1-184) are preferable.

[Formula 9]

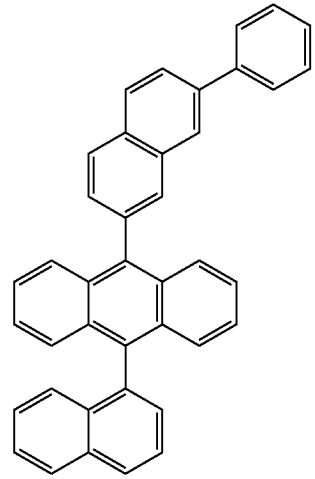

(1-1)

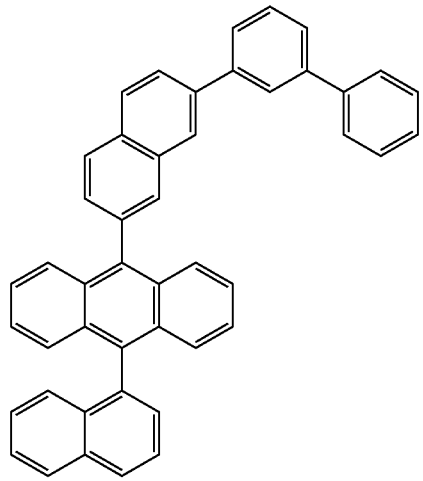

(1-2)

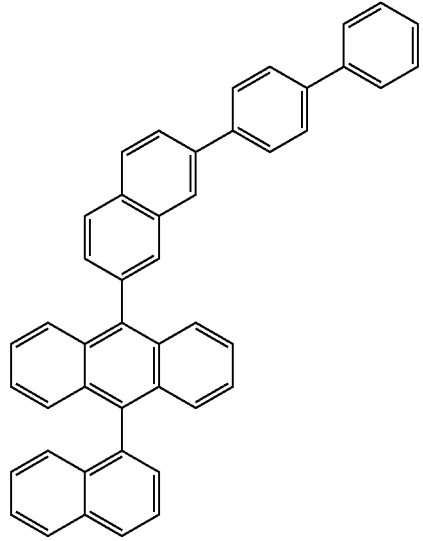

(1-3)

(1-4)
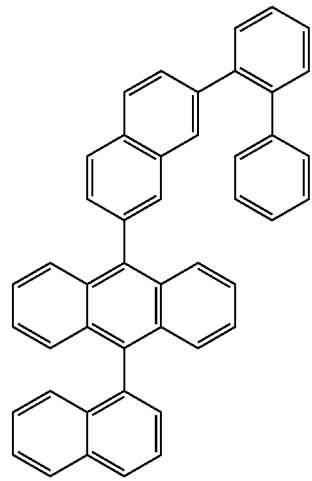
(1-6)
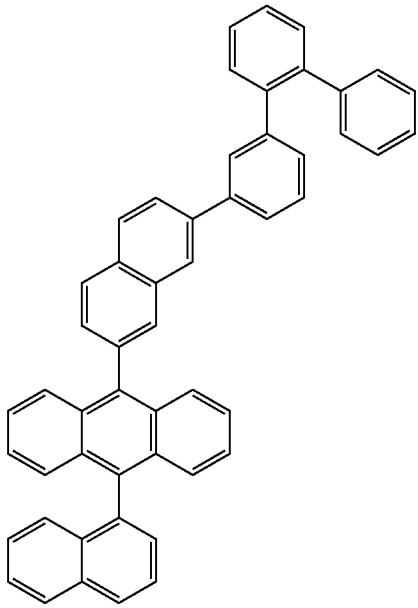
(1-5)
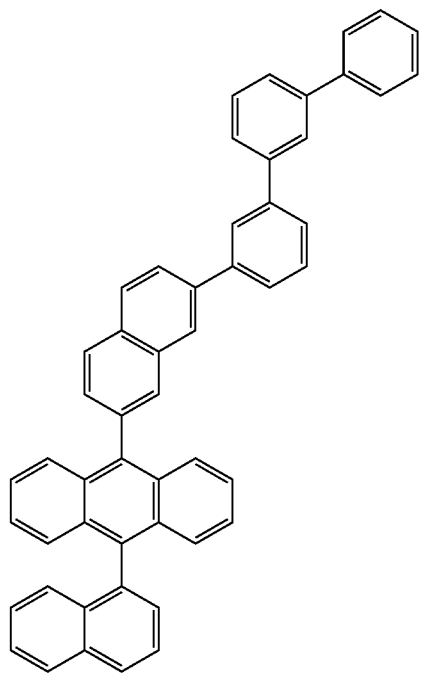
(1-7)
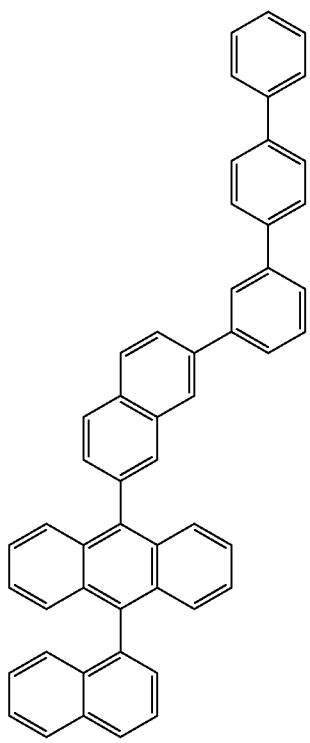

[Formula 10]
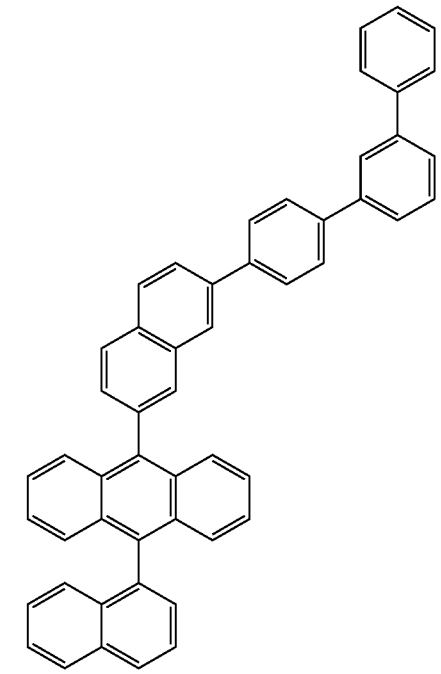
(1-8)
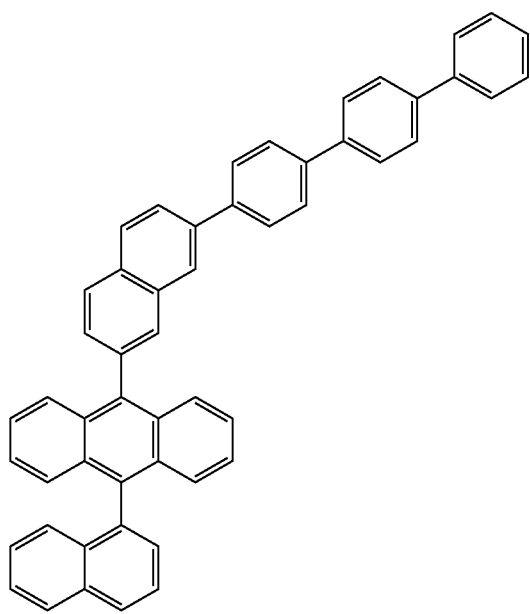
(1-9)
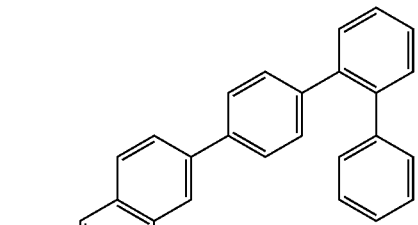
(1-10)
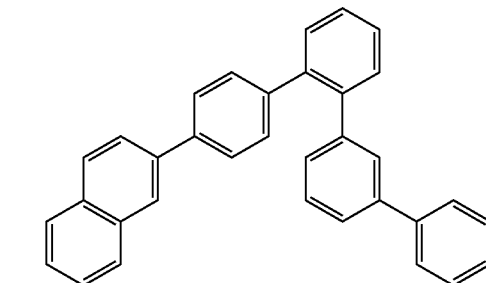
(1-11)
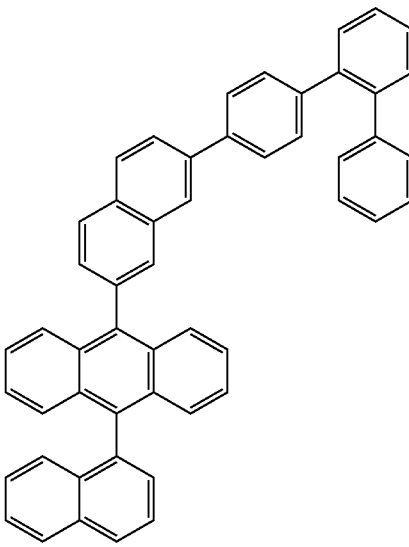
(1-12)

(1-13)
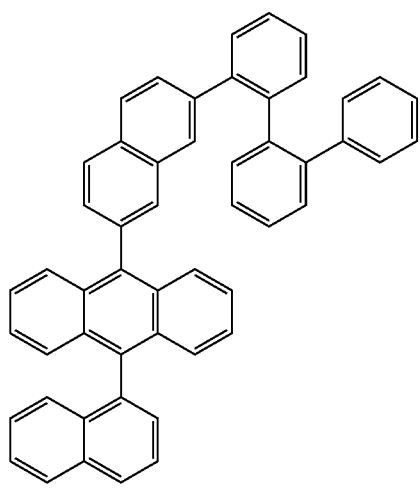
(1-14)
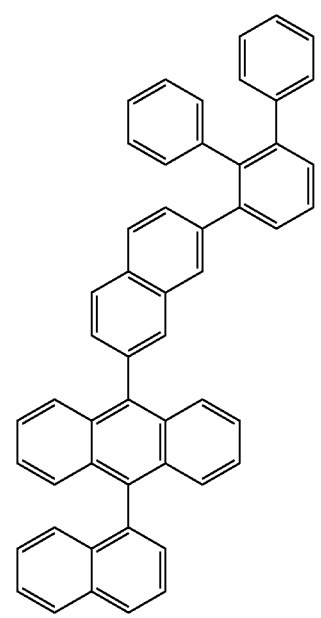
(1-16)
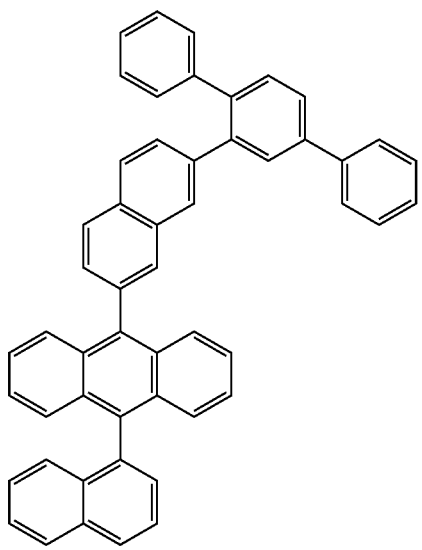
(1-15)
(1-17)
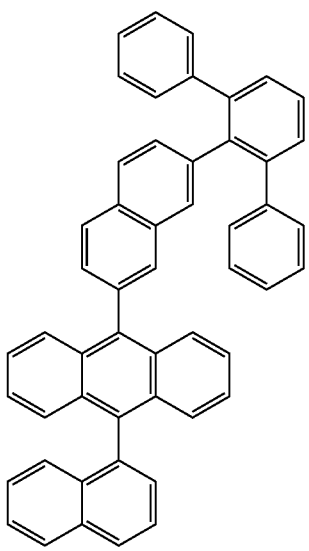

(1-18)
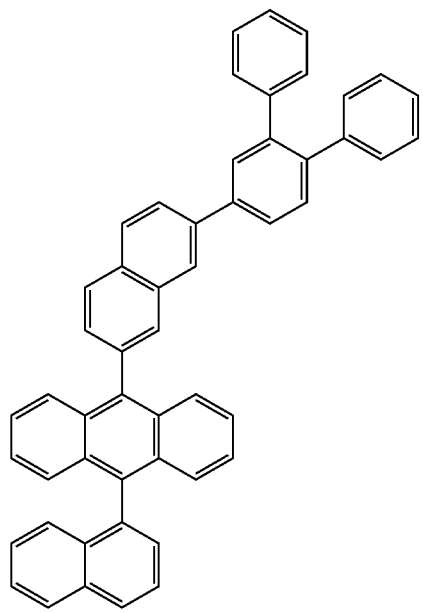
(1-20)
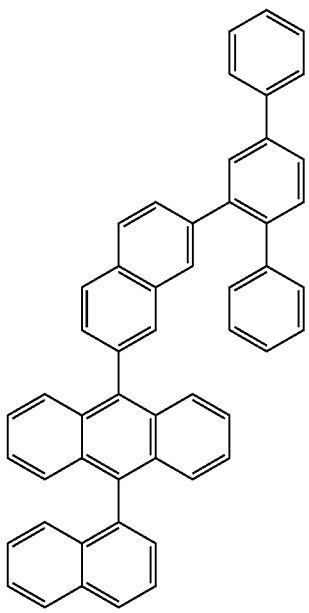
[Formula 11]
(1-19)
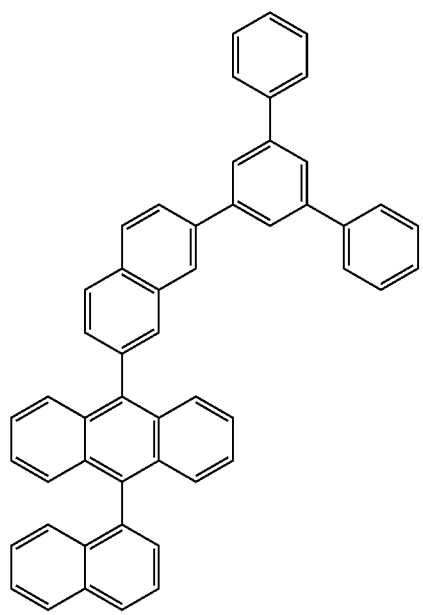
(1-21)
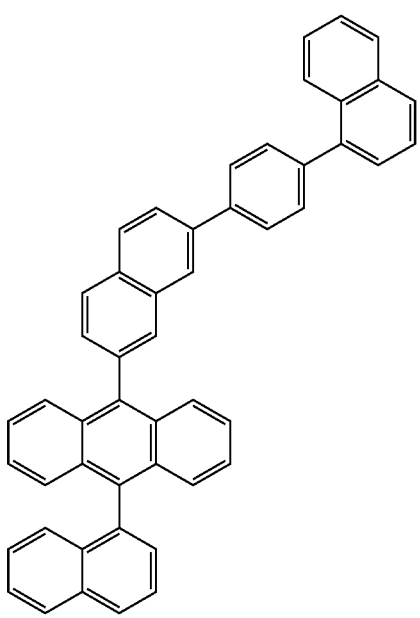

-continued
(1-22)
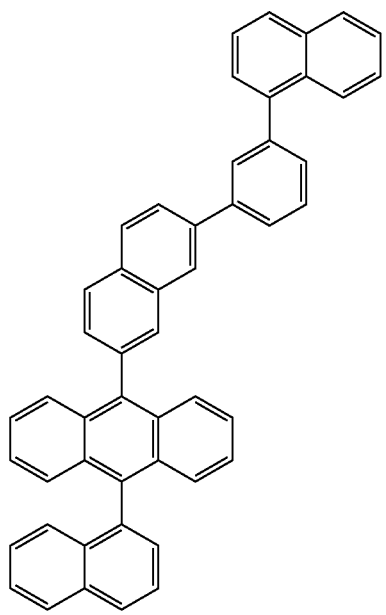
(1-24)
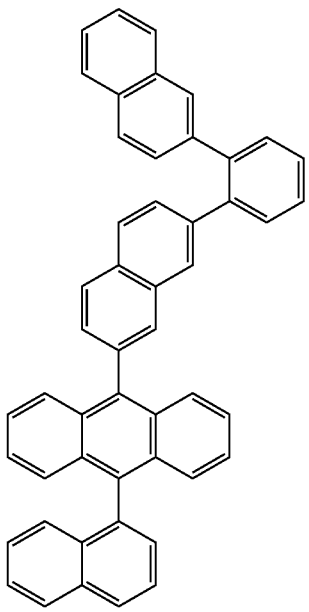
(1-23)
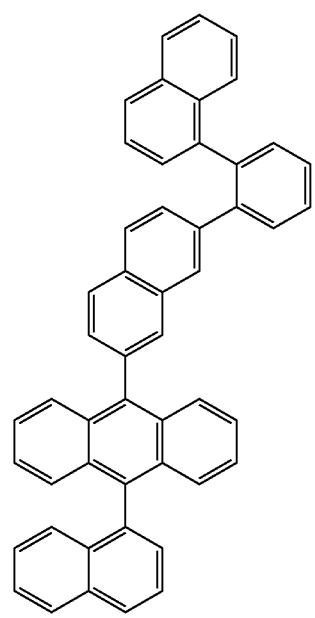
(1-25)
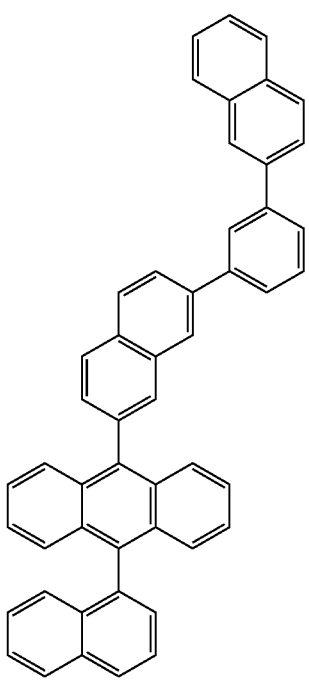

[Formula 12]

(1-26)

(1-27)

(1-28)

(1-29)

(1-30)
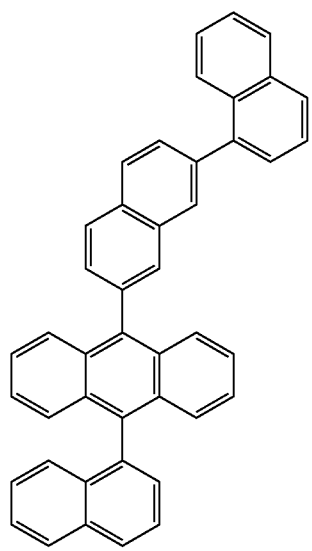
(1-32)
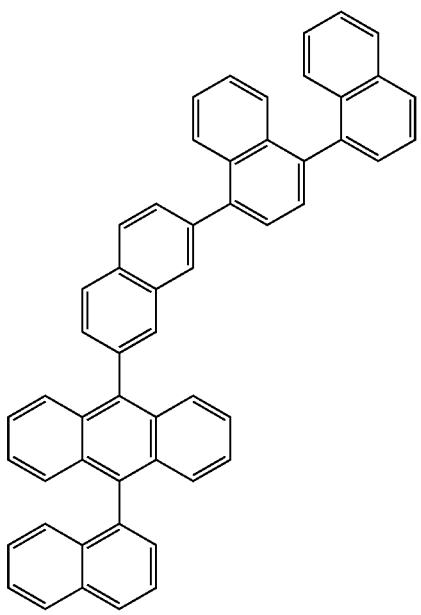
(1-31)
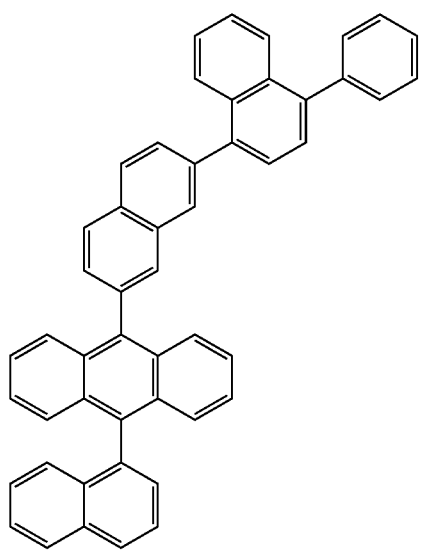
(1-33)
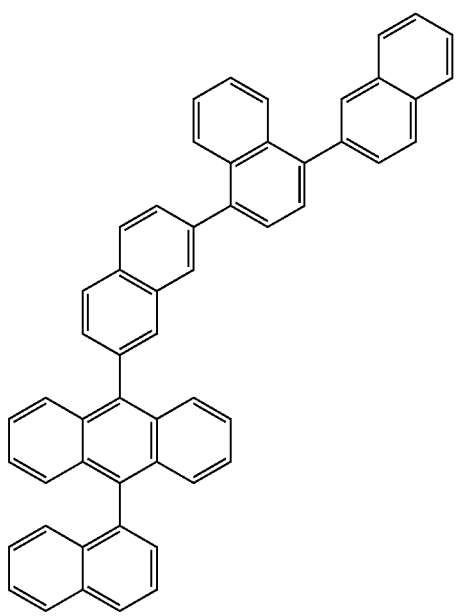

(1-34)
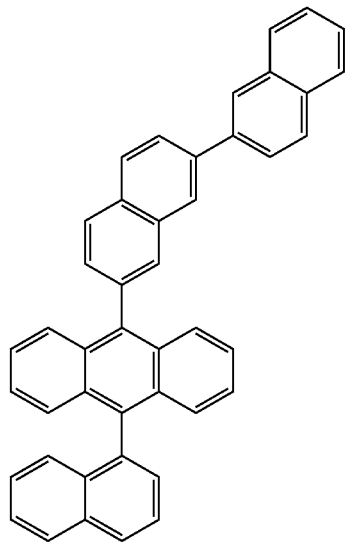
(1-35)
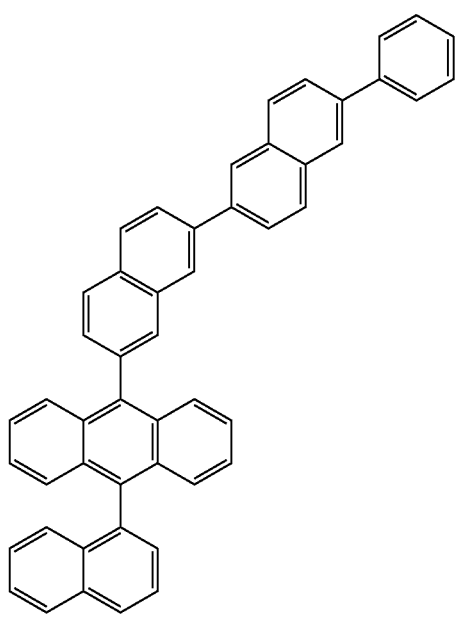
(1-36)
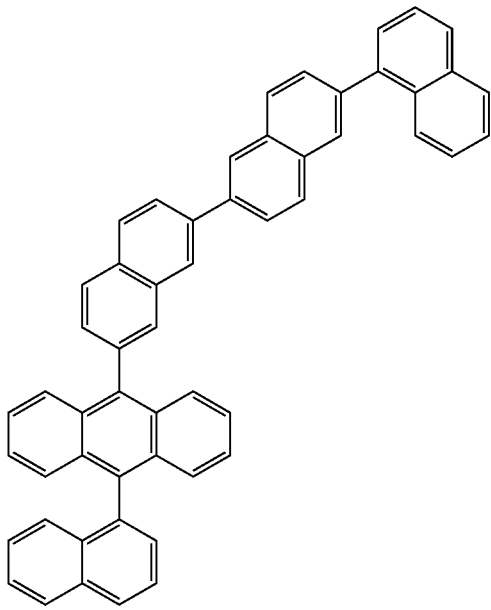
[Formula 13]
(1-37)
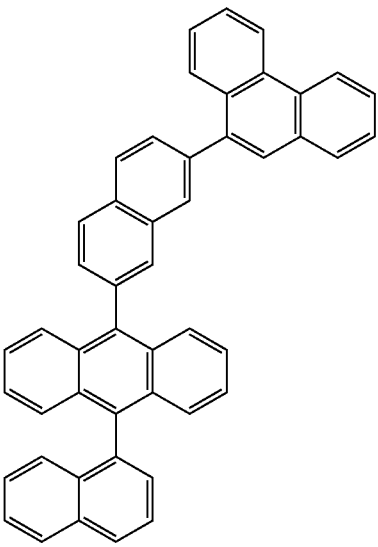

(1-38)
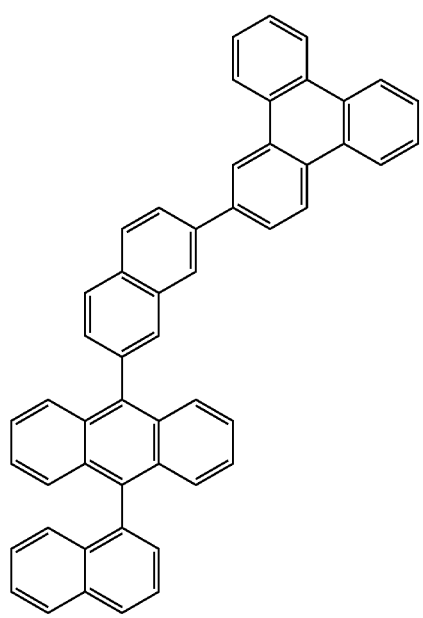
(1-40)
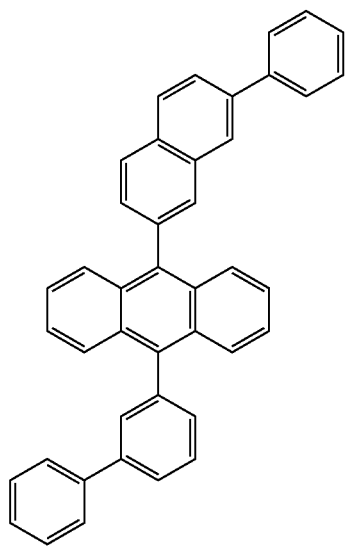
(1-39)
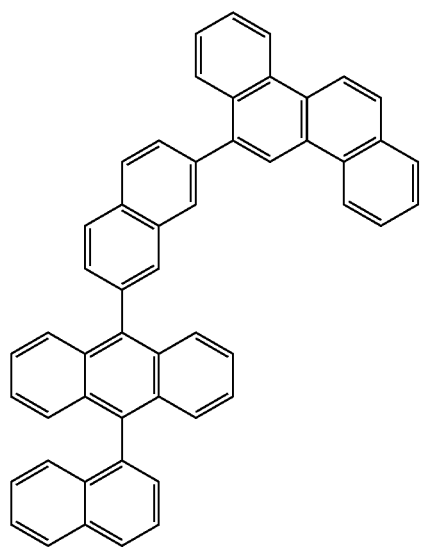
(1-41)
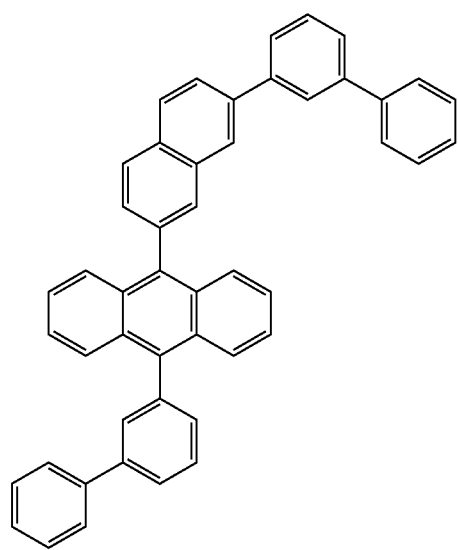

(1-42)
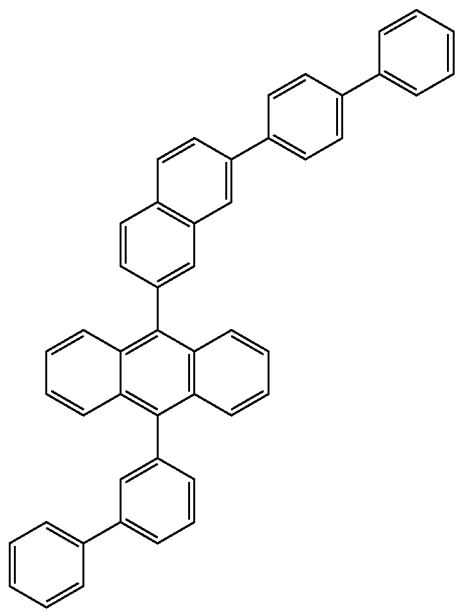
(1-43)
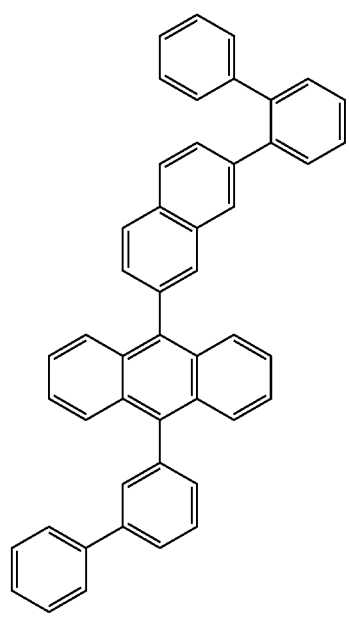
(1-44)
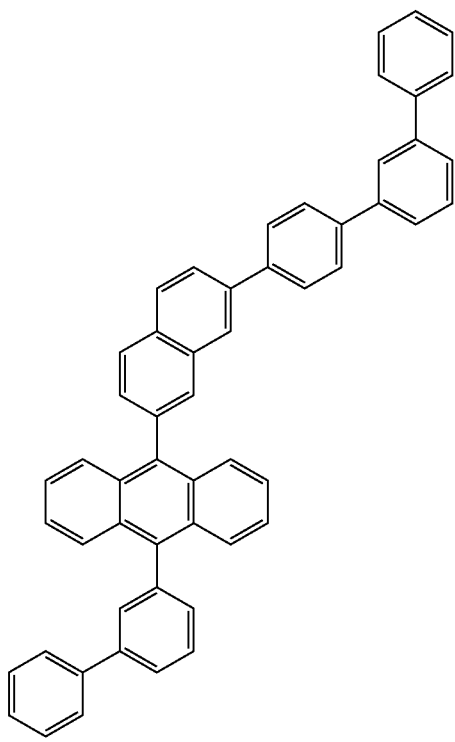
(1-45)
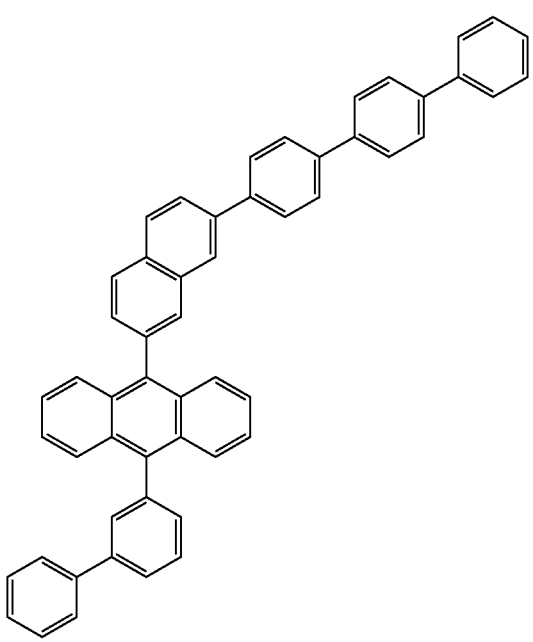

[Formula 14]
(1-46)
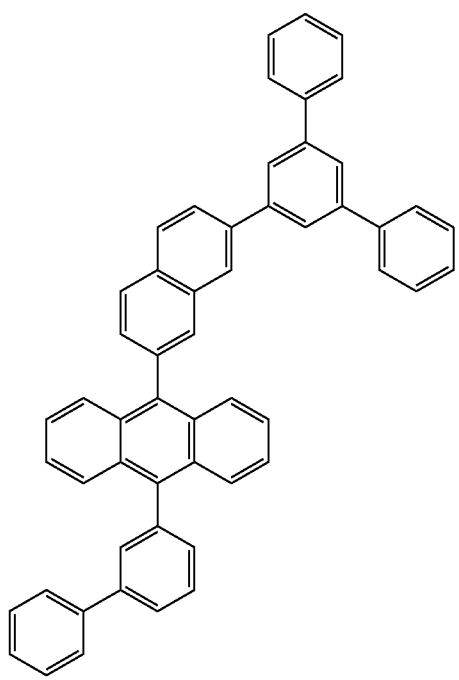
(1-48)
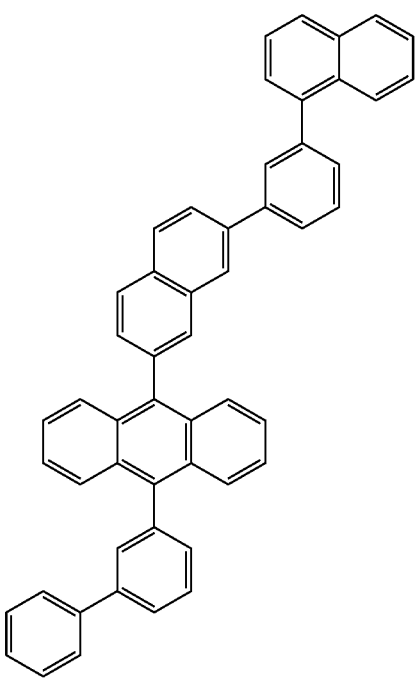
(1-47)
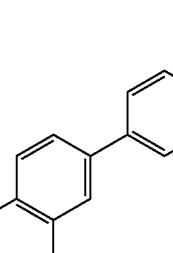
(1-49)

(1-50)
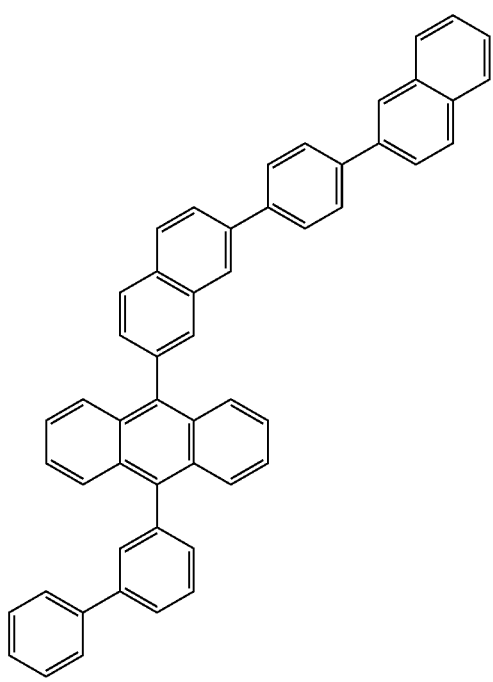
(1-52)
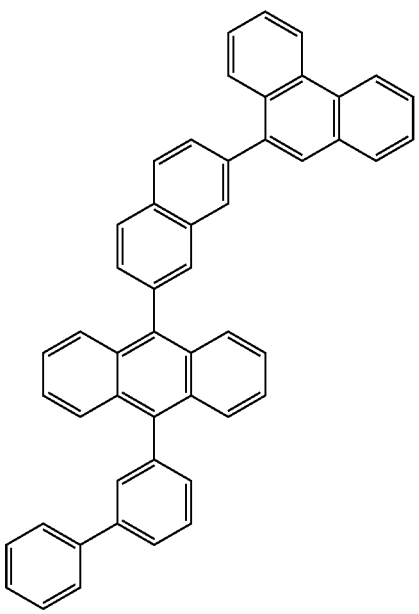
(1-51)
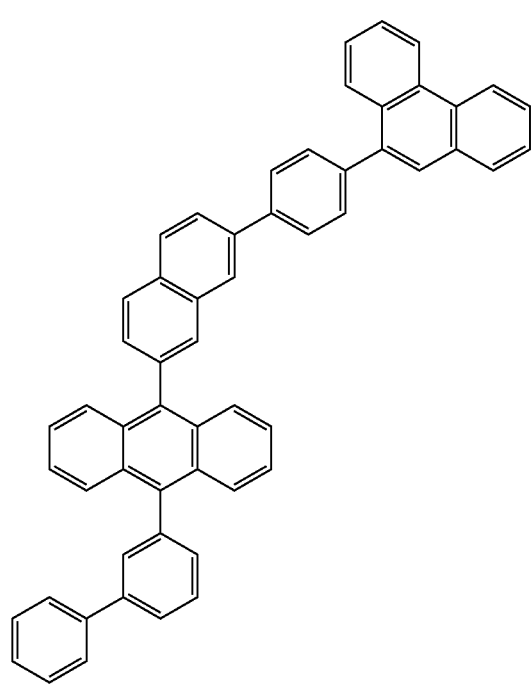
(1-53)
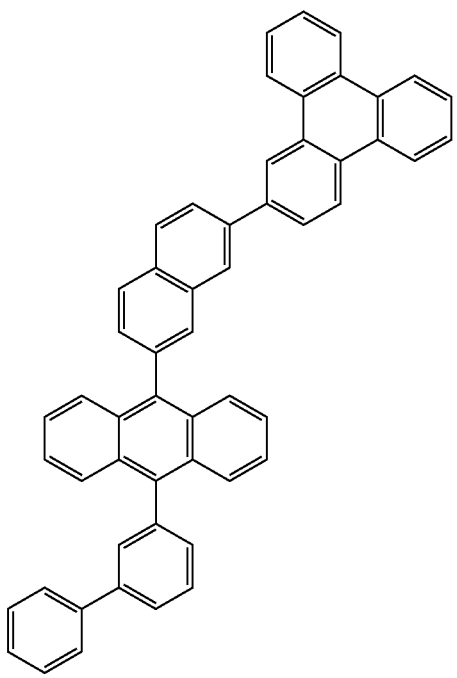

(1-54)
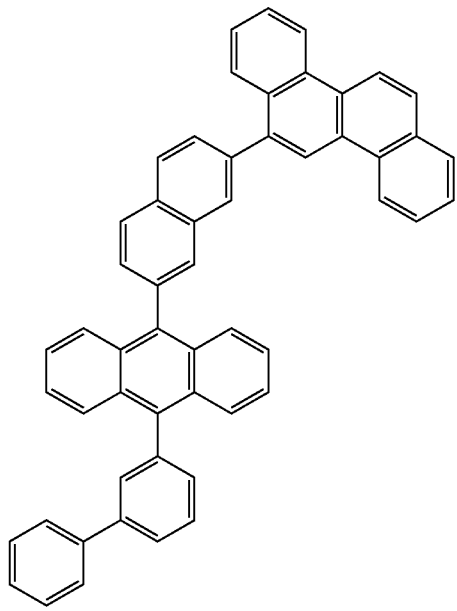
[Formula 15]
(1-55)
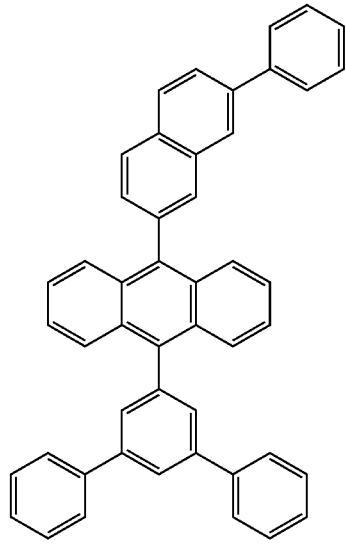
(1-56)
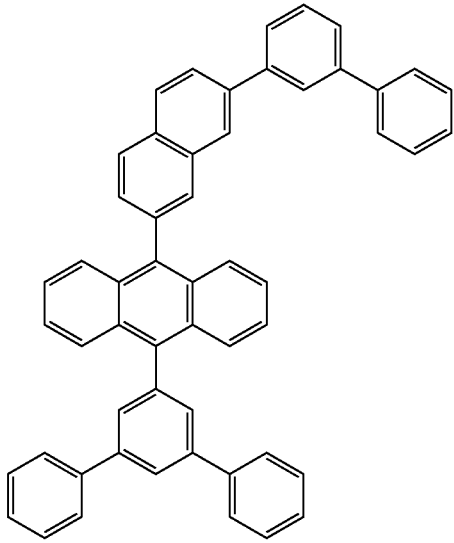
(1-57)
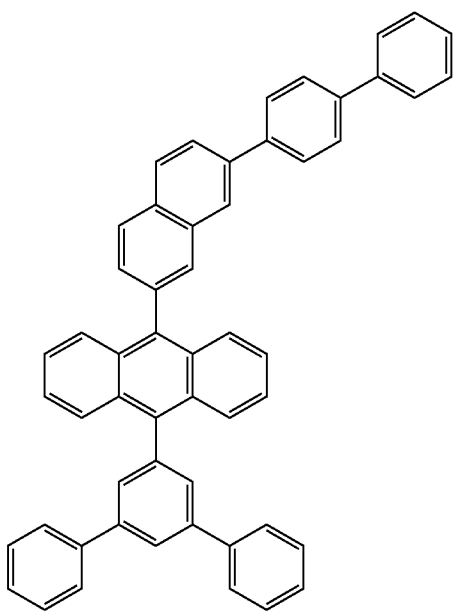

(1-58)
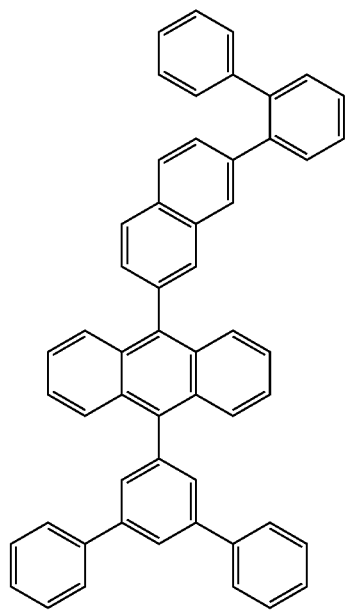
(1-59)
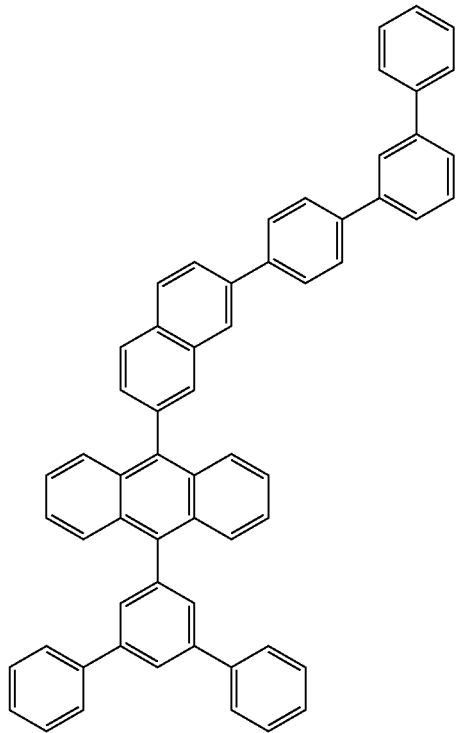
(1-60)
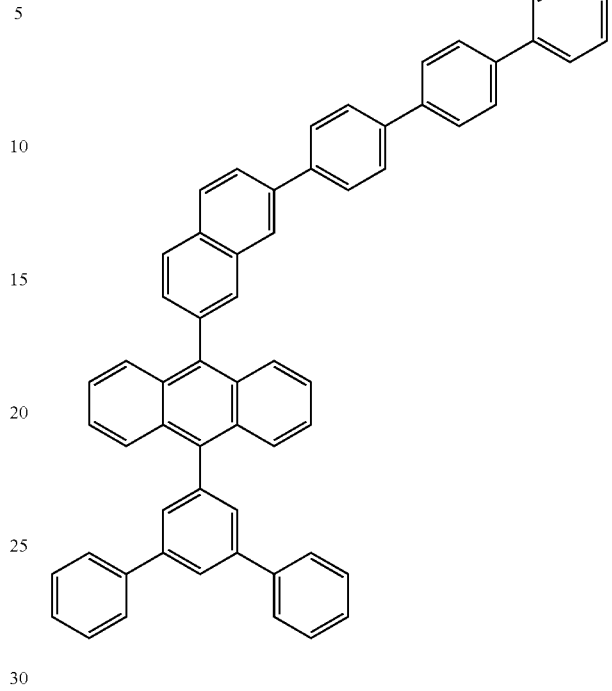
(1-61)
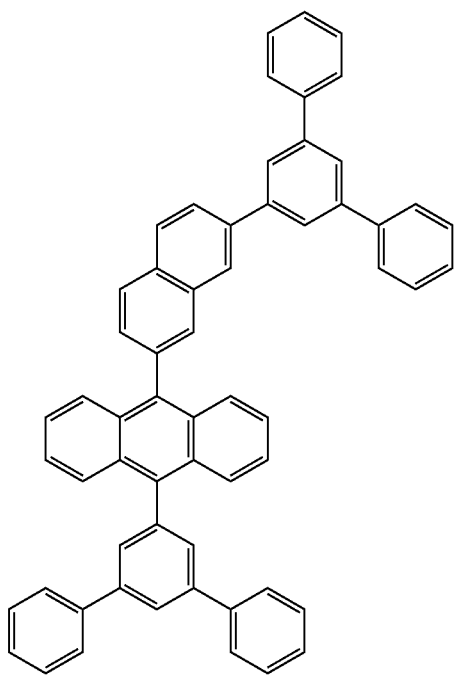

(1-62)
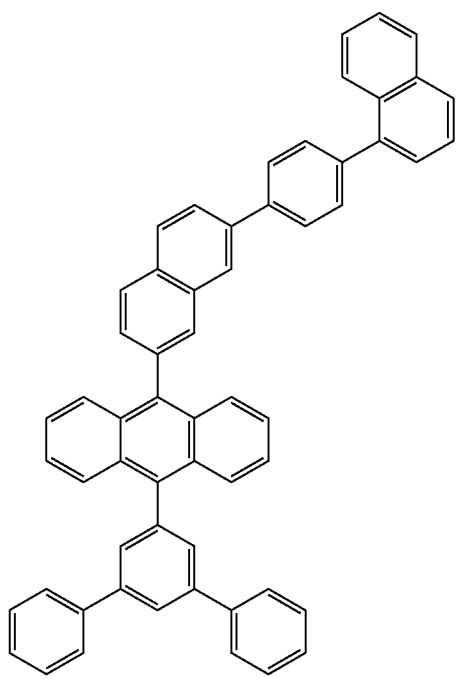
[Formula 16]
(1-64)
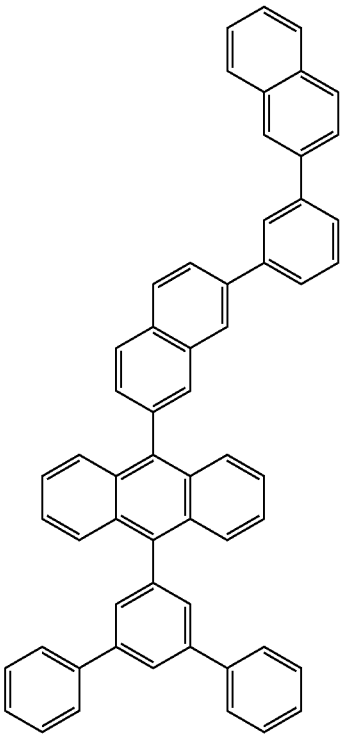
(1-63)
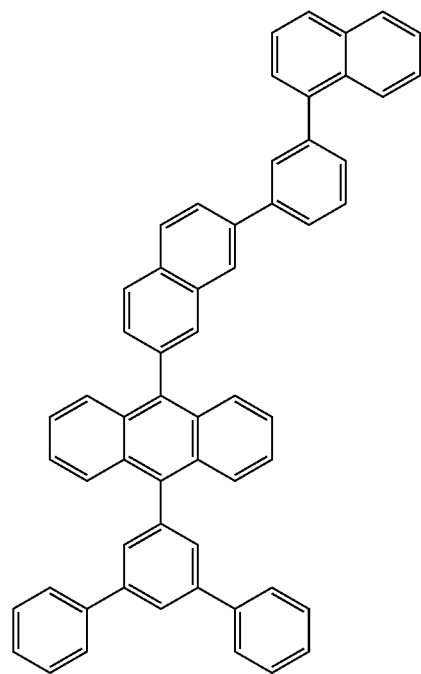
(1-65)
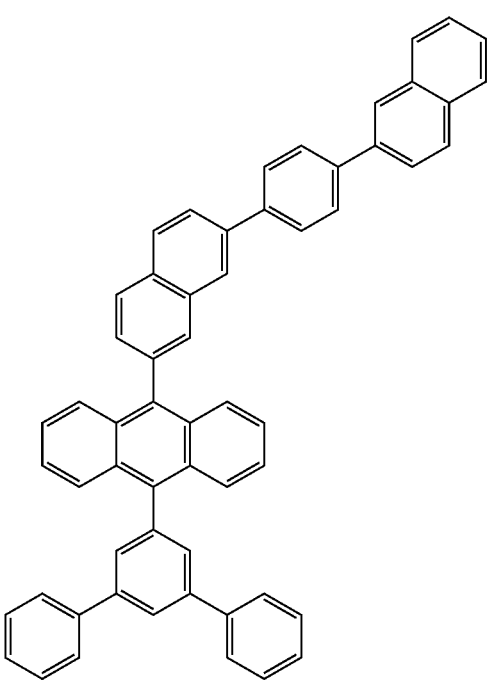

(1-66)
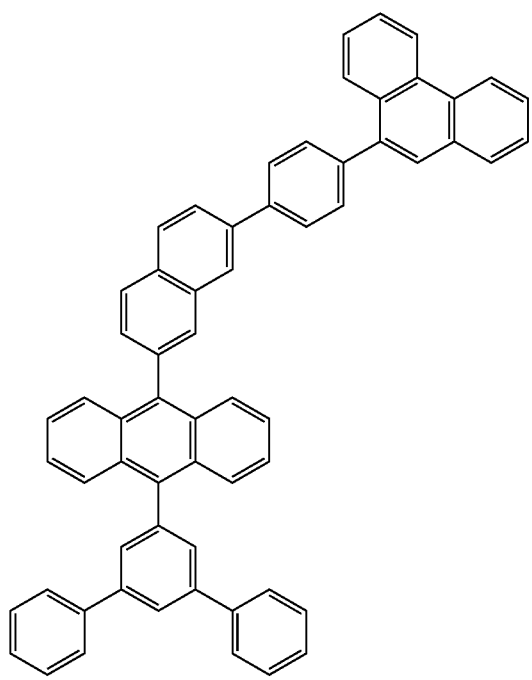
(1-68)
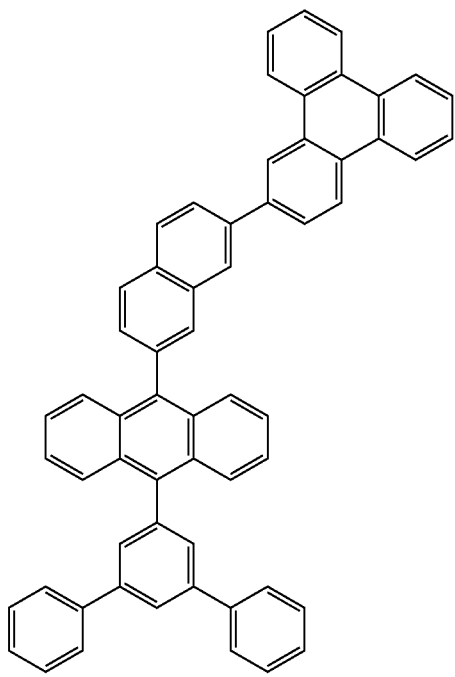
(1-67)
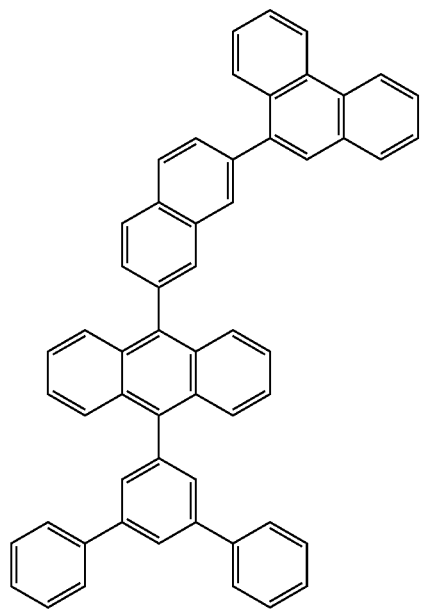
(1-69)
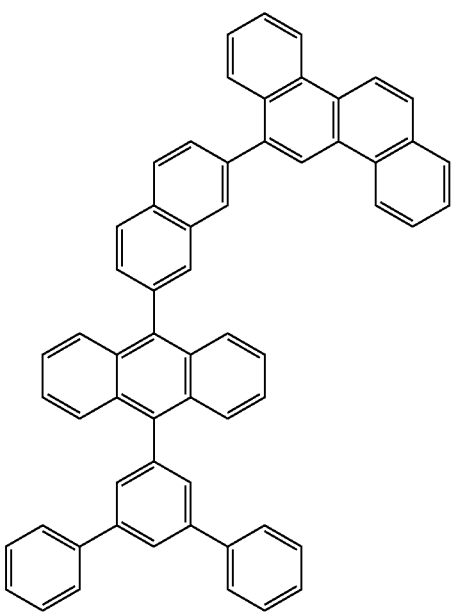

(1-70)
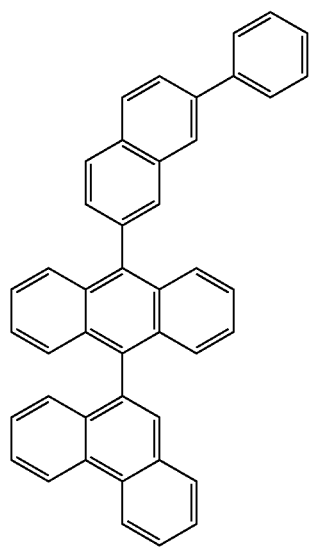
(1-72)
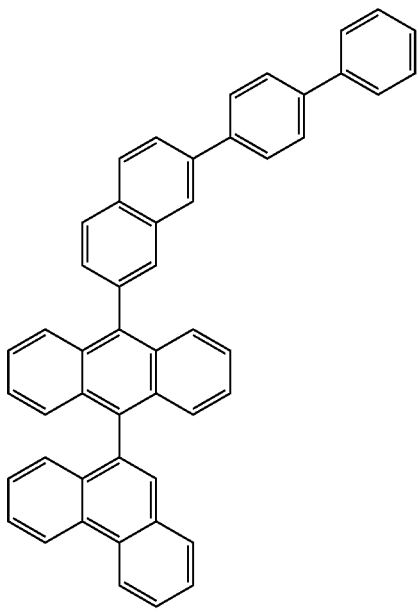
[Formula 17]
(1-71)
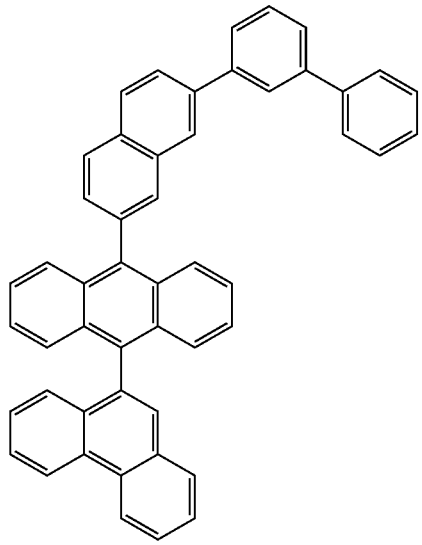
(1-73)
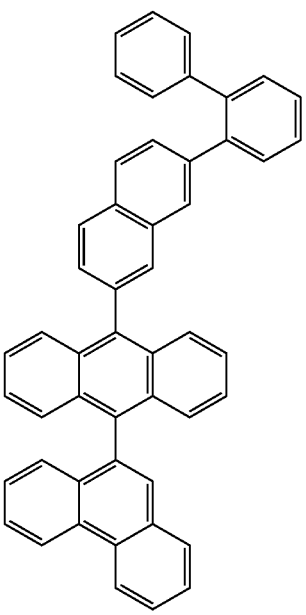

(1-74)
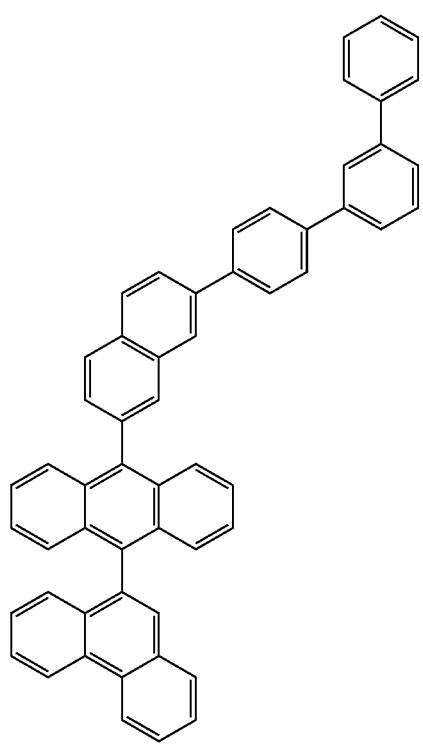
(1-76)
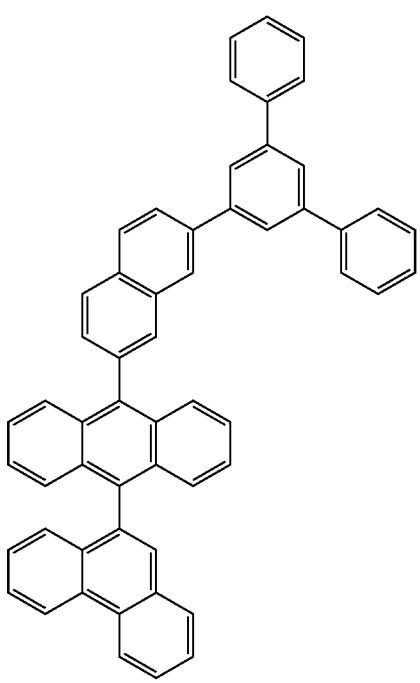
(1-75)
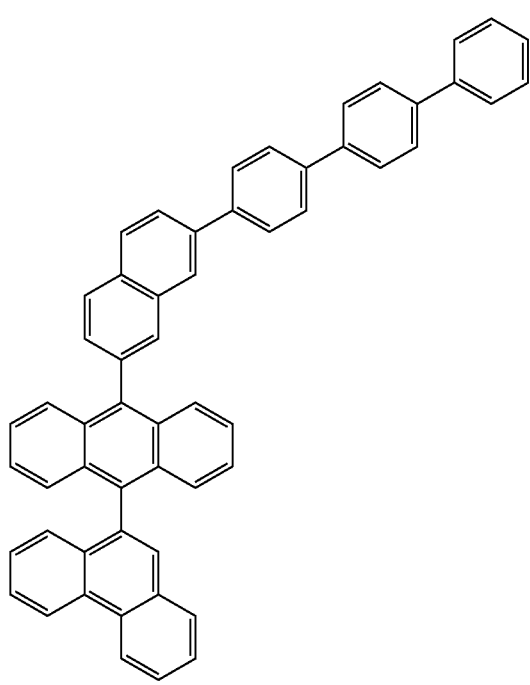
(1-77)
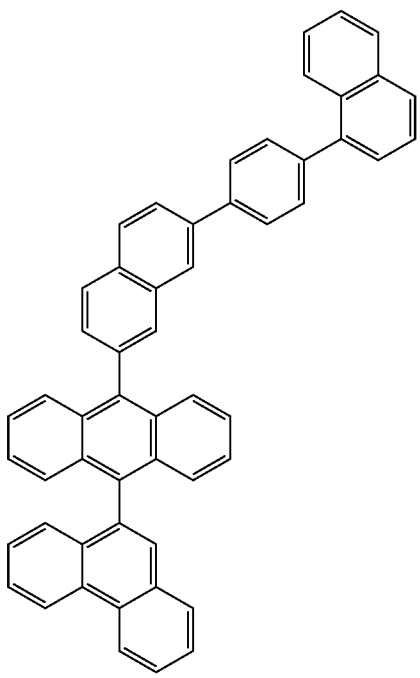

-continued
(1-78)
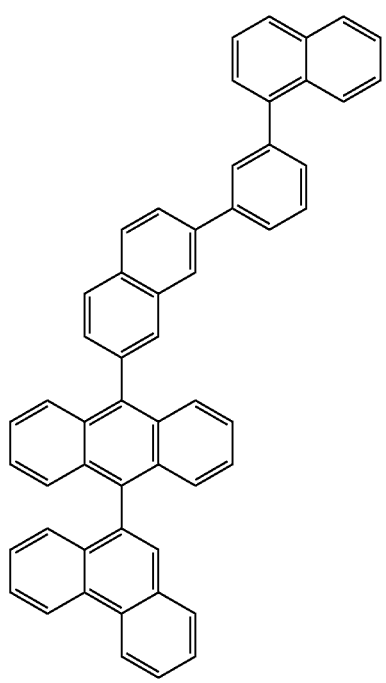
(1-79)
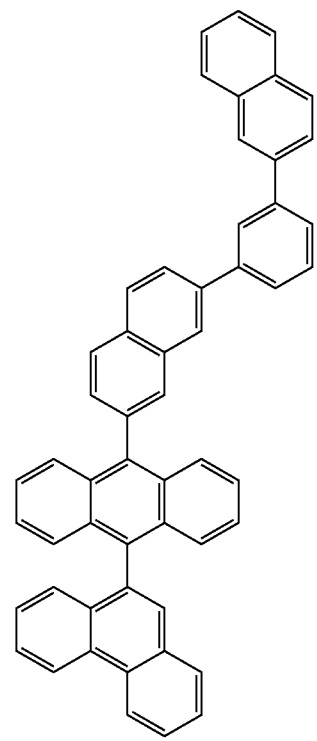
-continued
(1-80)
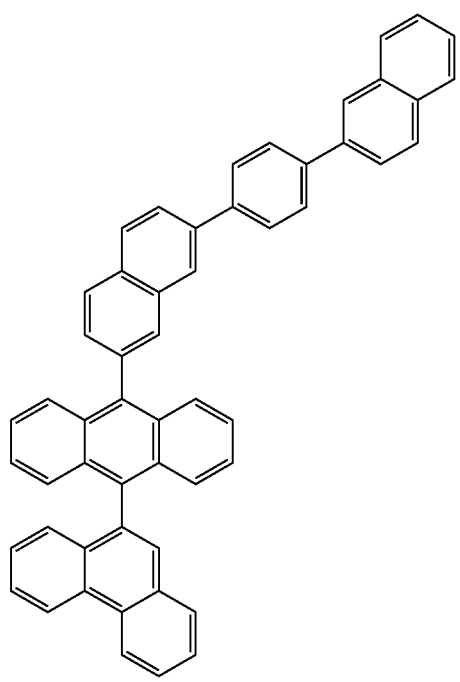
(1-81)
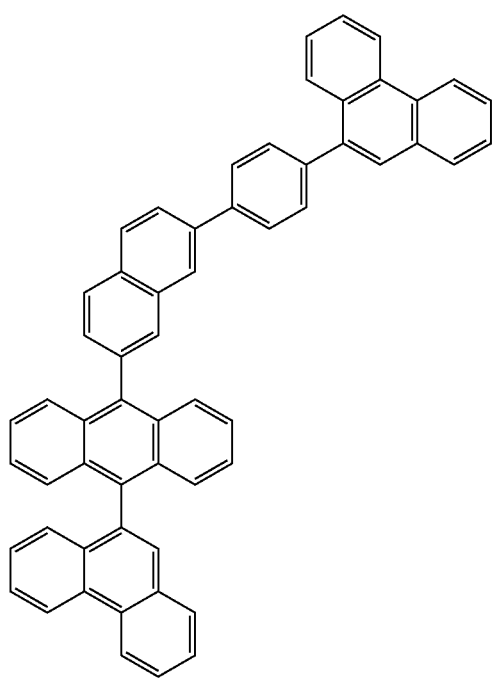

[Formula 18]
(1-82)
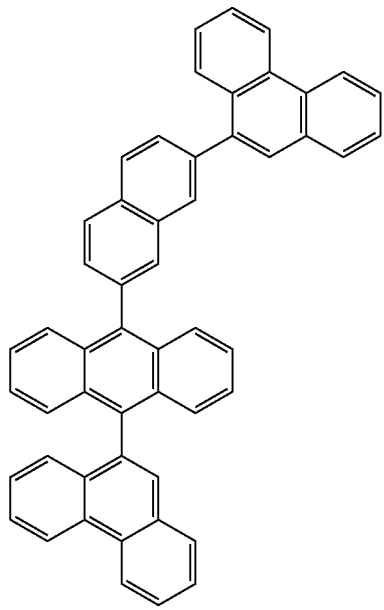
(1-83)
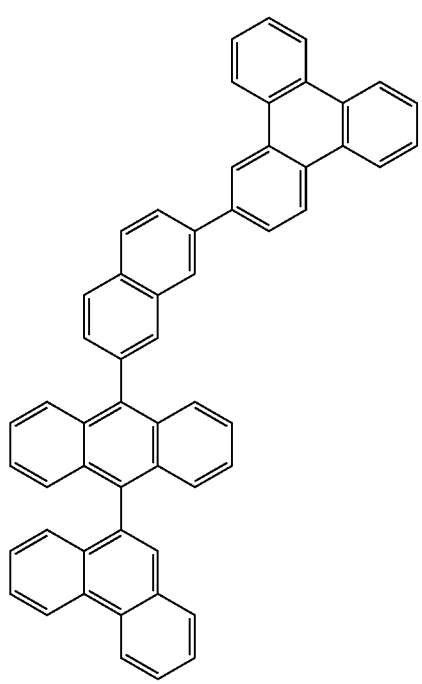
(1-84)
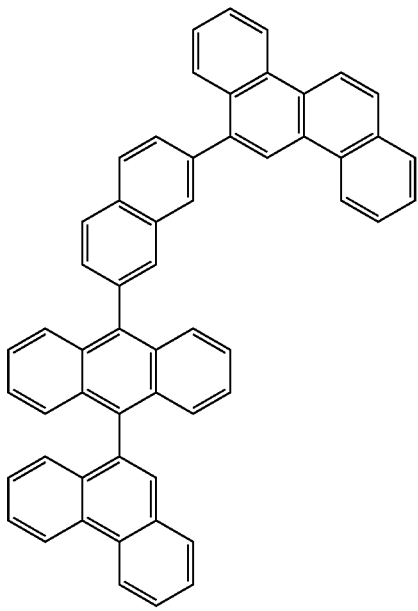
(1-85)
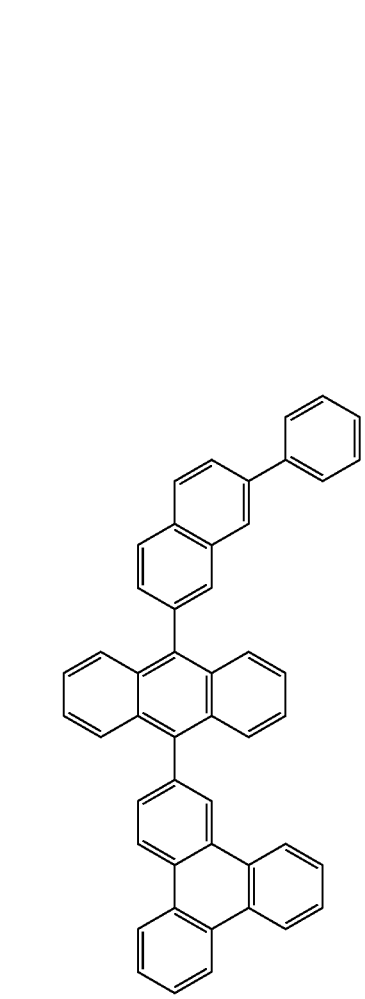

(1-86)
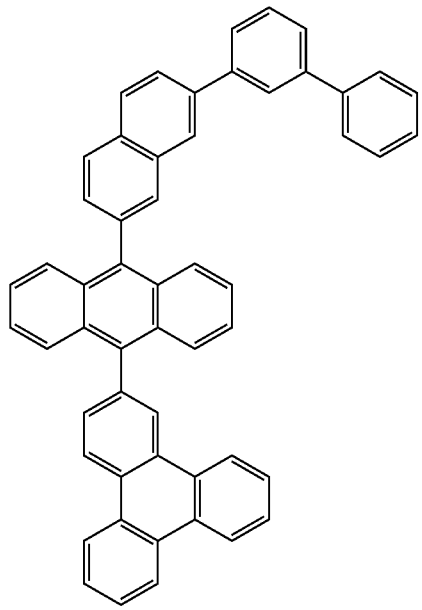
(1-88)
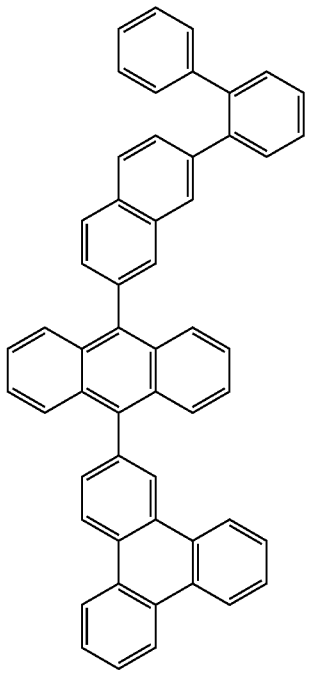
(1-87)
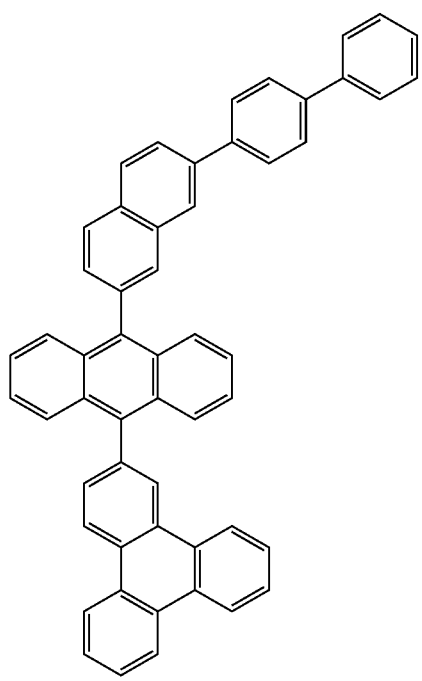
(1-89)
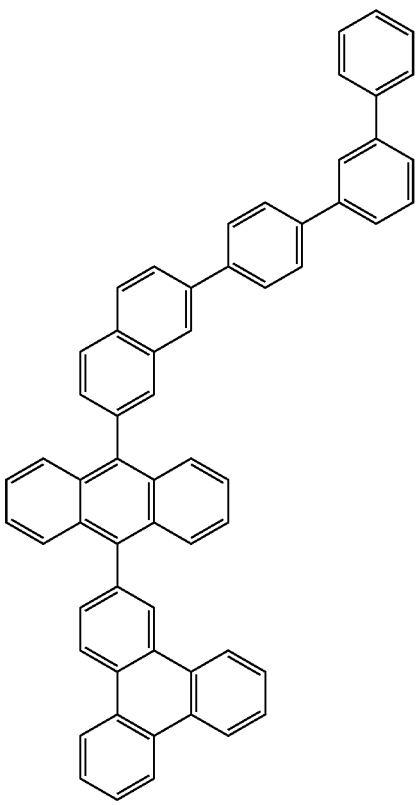

(1-90)
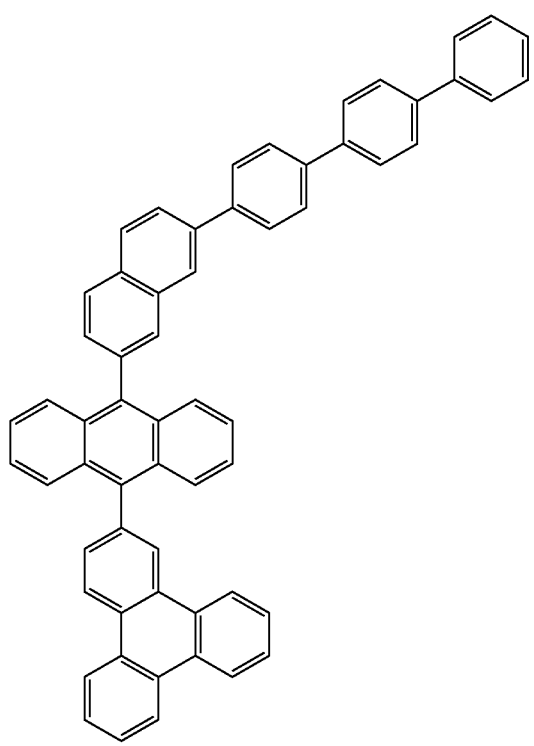
(1-92)
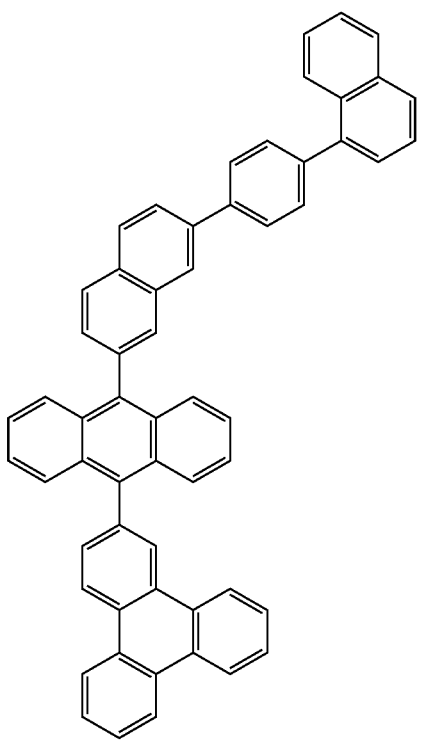
[Formula 19]
(1-91)
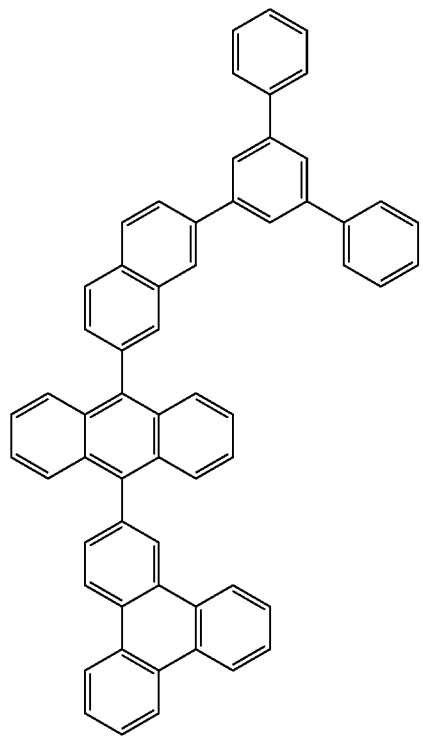
(1-93)
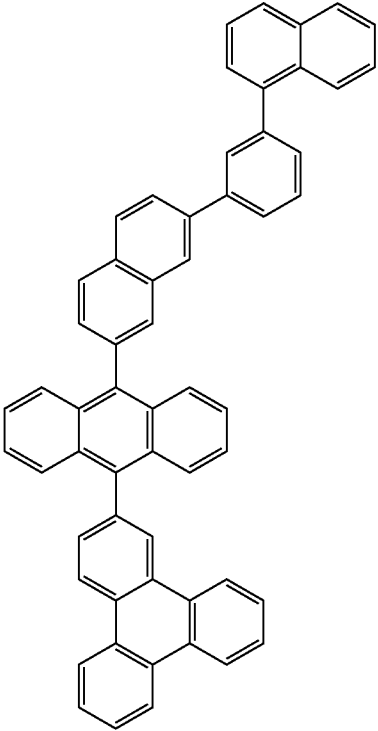

(1-94)
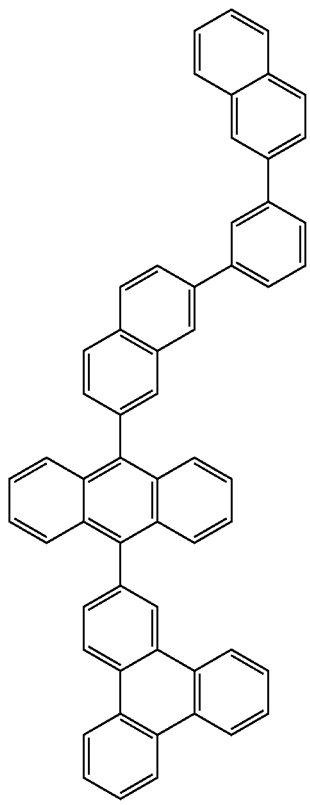
(1-96)
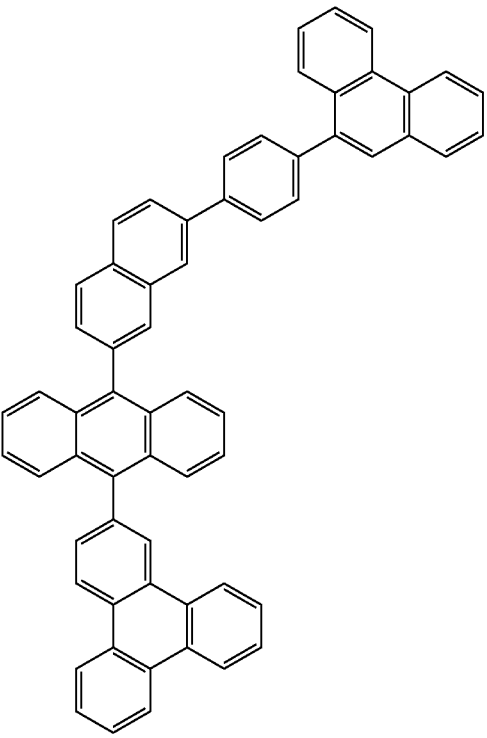
(1-95)
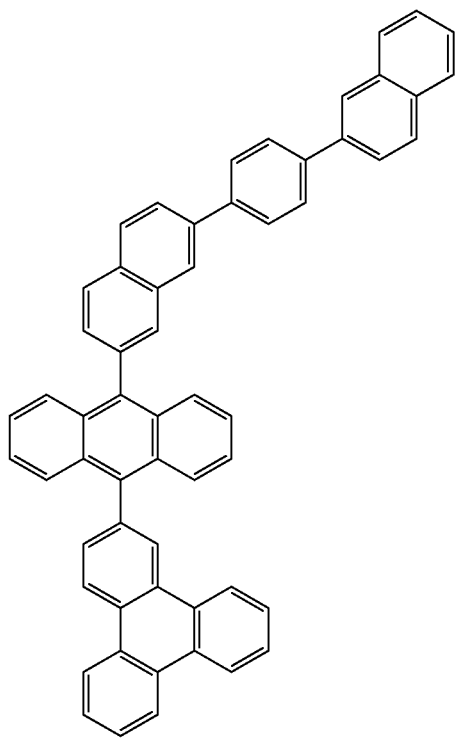
(1-97)

(1-98)
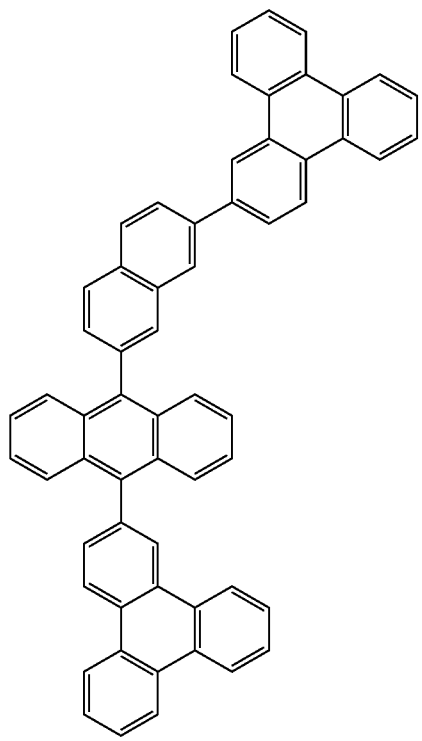
(1-99)
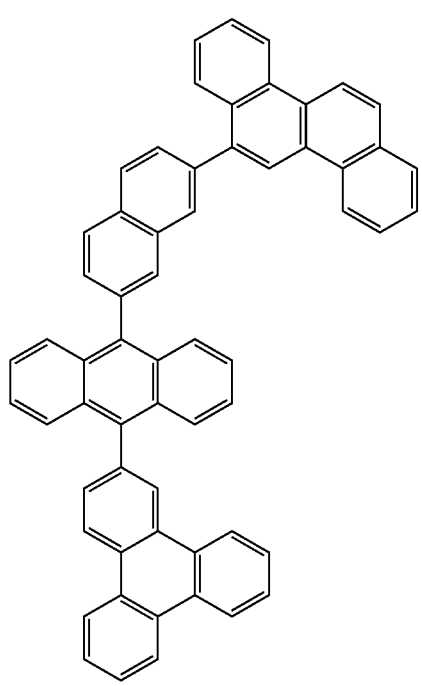
[Formula 20]
(1-100)
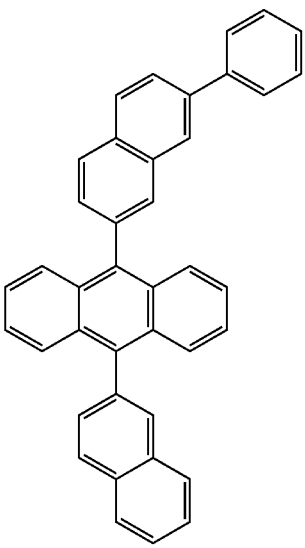
(1-101)
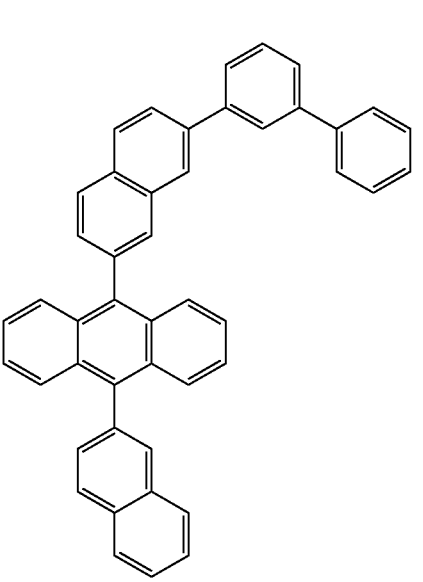

(1-102)
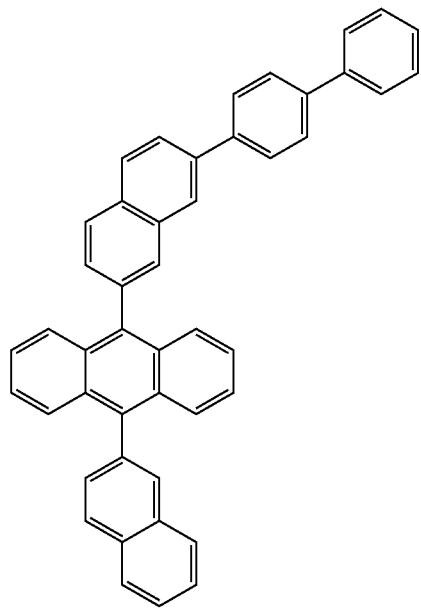
(1-104)
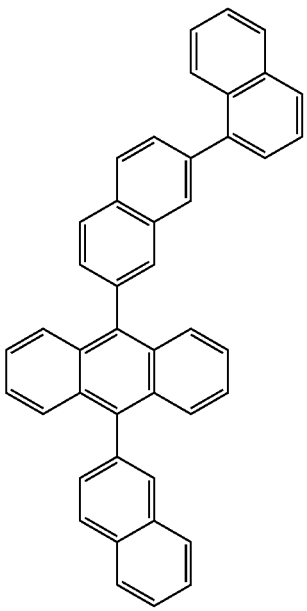
(1-103)
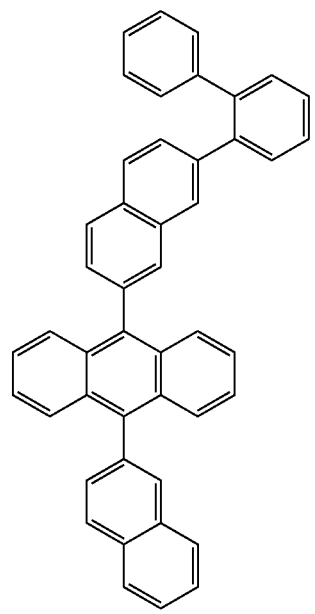
(1-105)
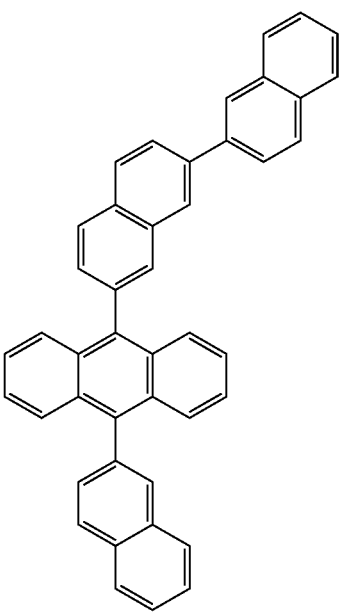

(1-106)
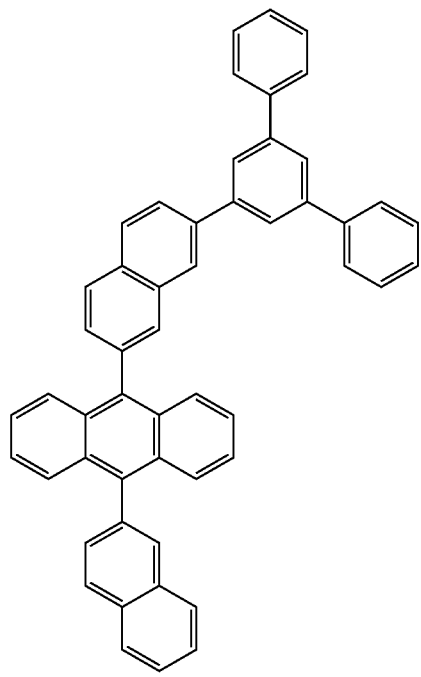
(1-108)
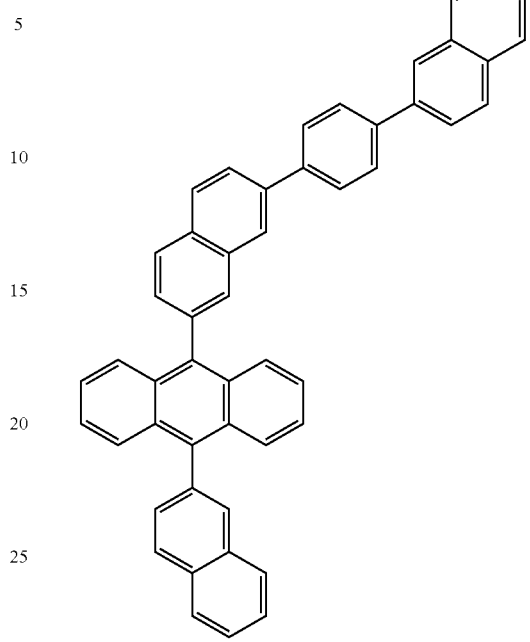
(1-107)
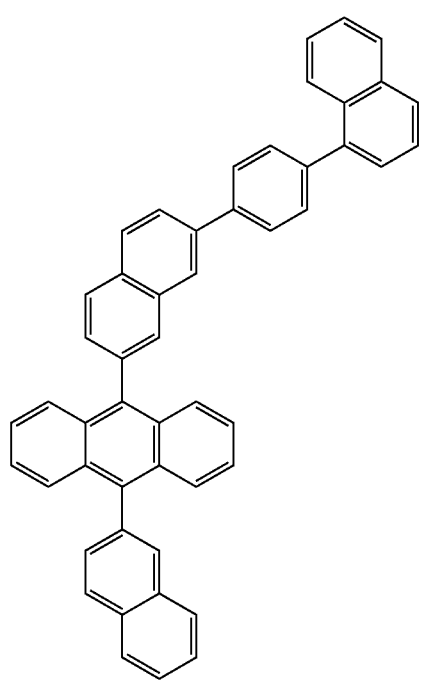
[Formula 21]
(1-109)
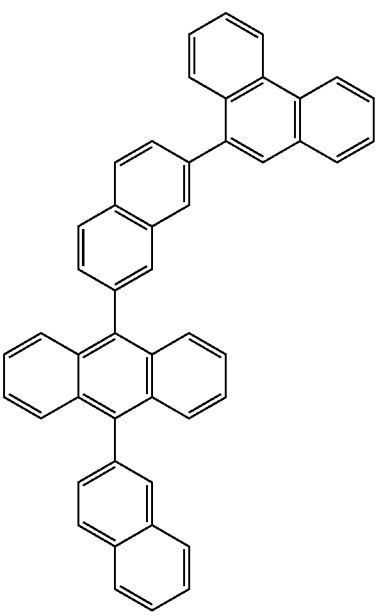

(1-110)
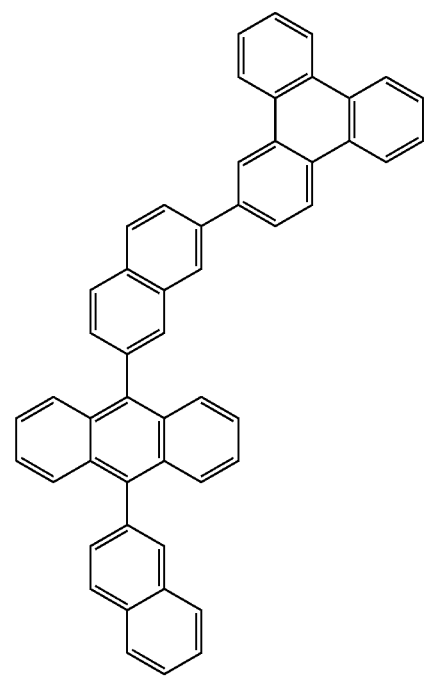
(1-111)
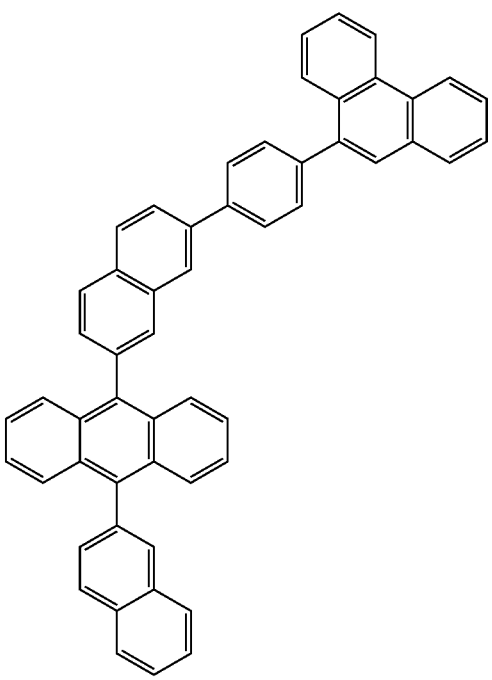
(1-112)
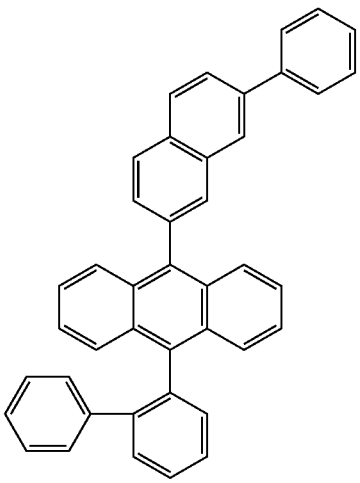
(1-113)
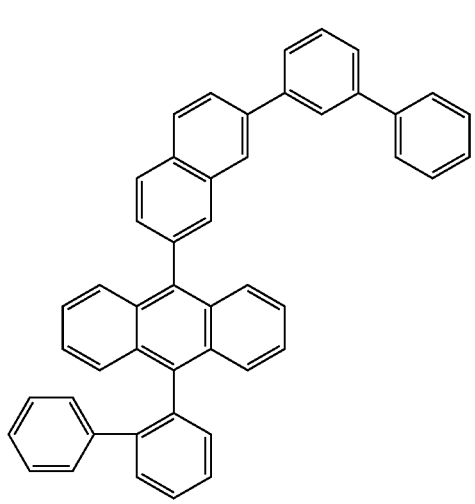
(1-114)
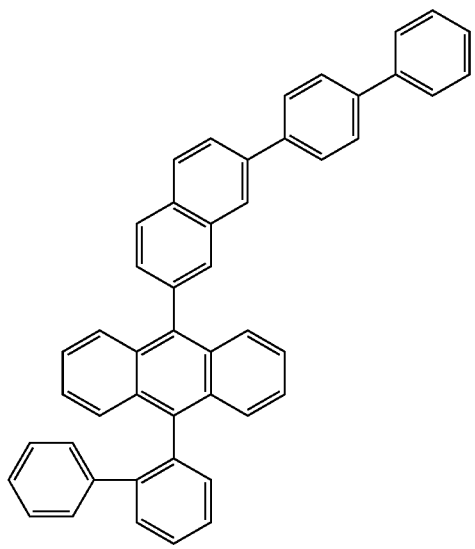

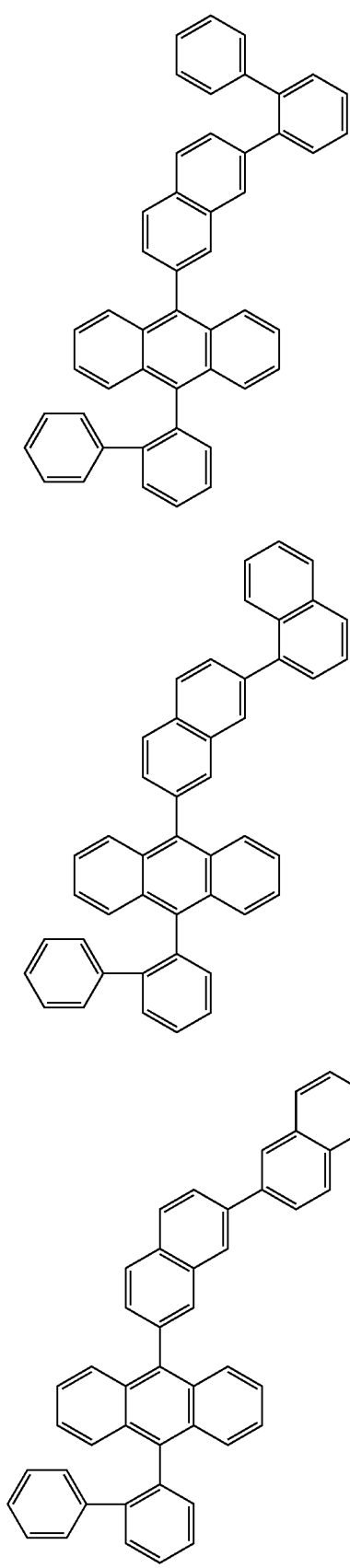
(1-115)
(1-116)
(1-117)
[Formula 22]
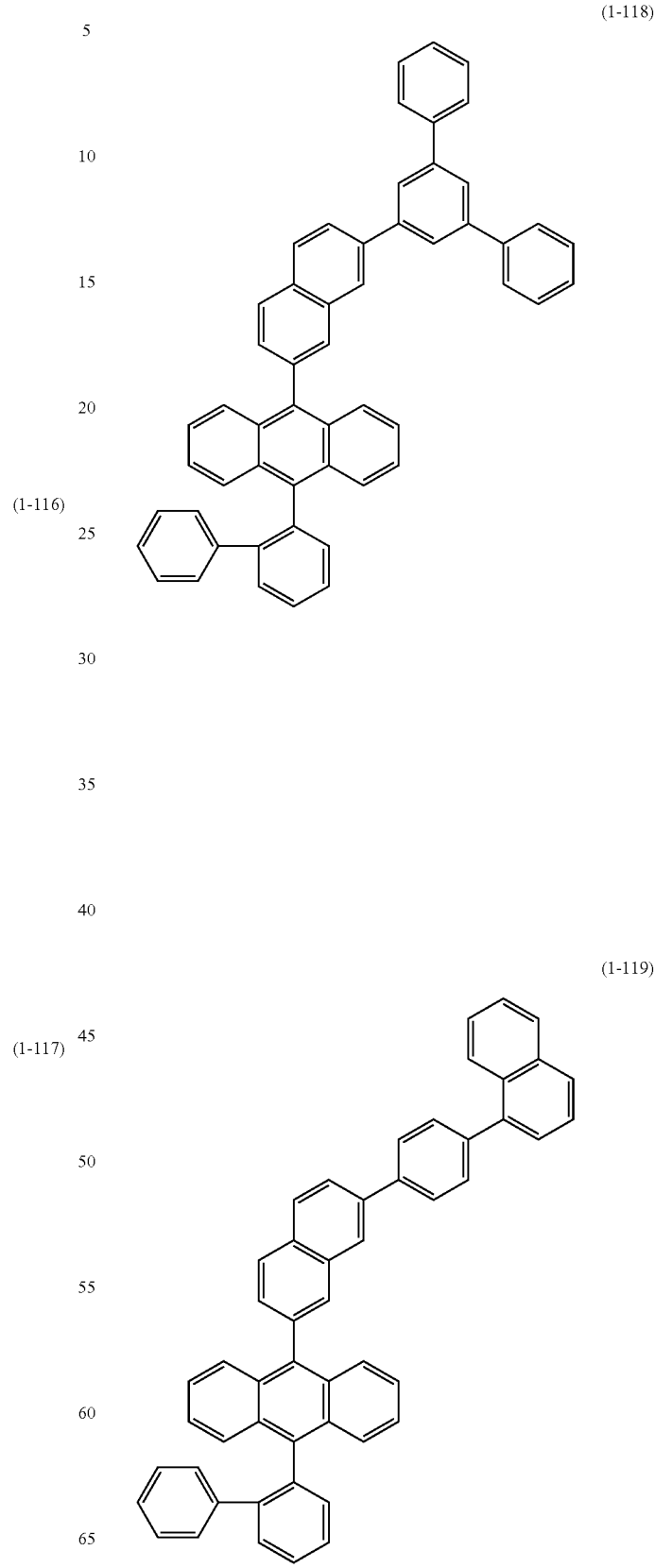
(1-118)
(1-119)

(1-120)
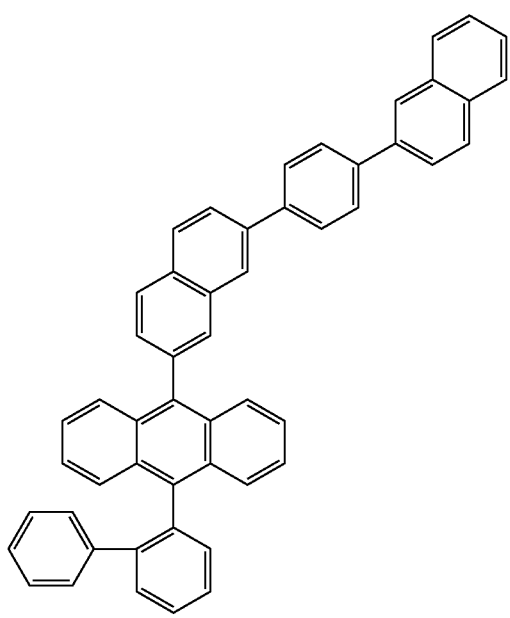
(1-122)
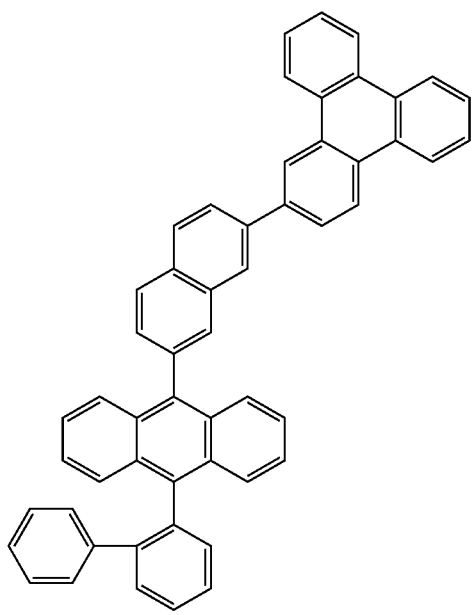
(1-121)
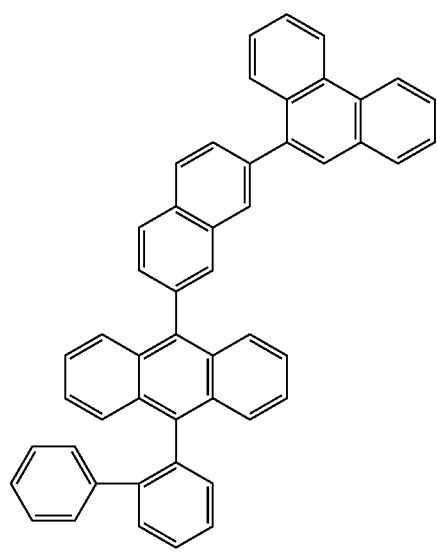
(1-123)
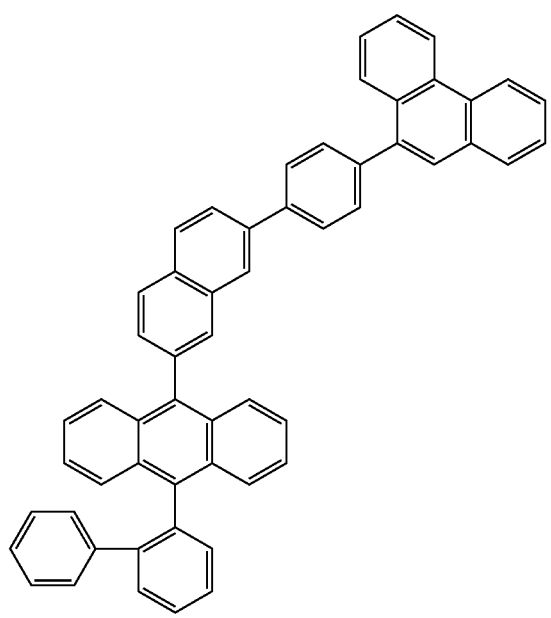

(1-124)
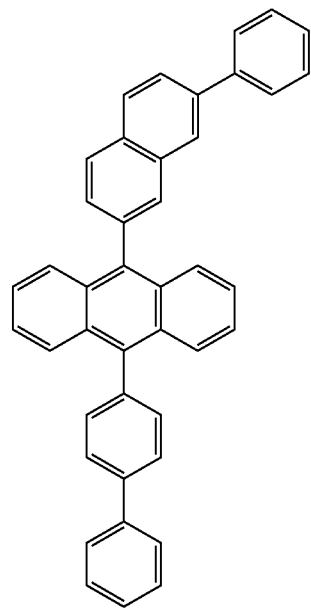
(1-126)
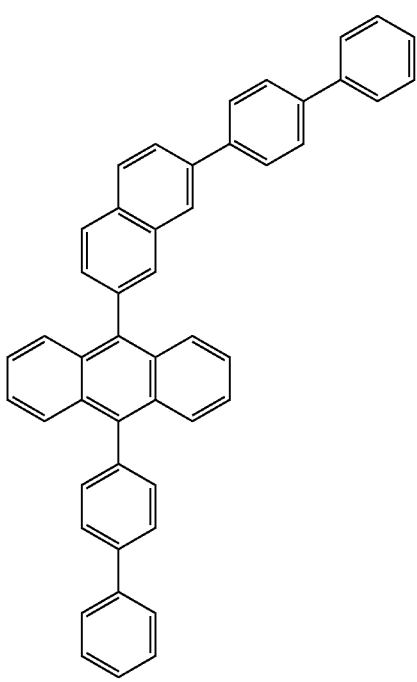
[Formula 23]
(1-125)
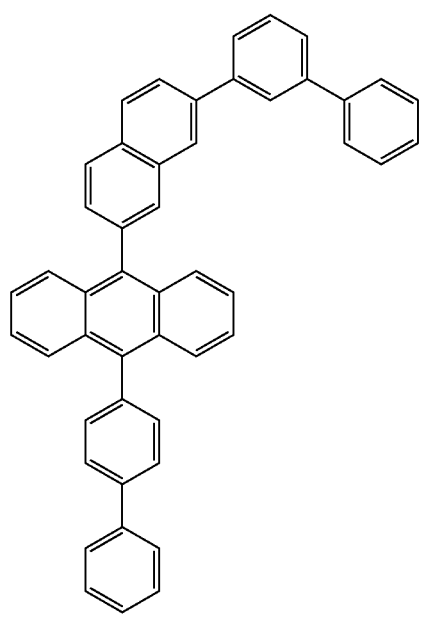
(1-127)
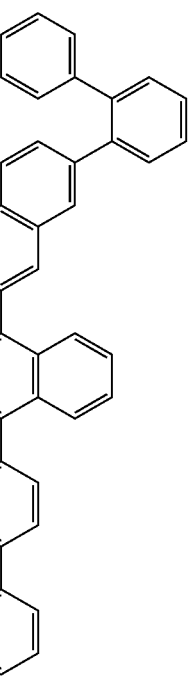

(1-128)
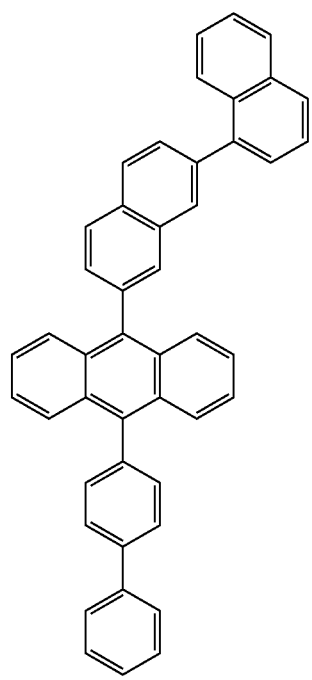
(1-129)
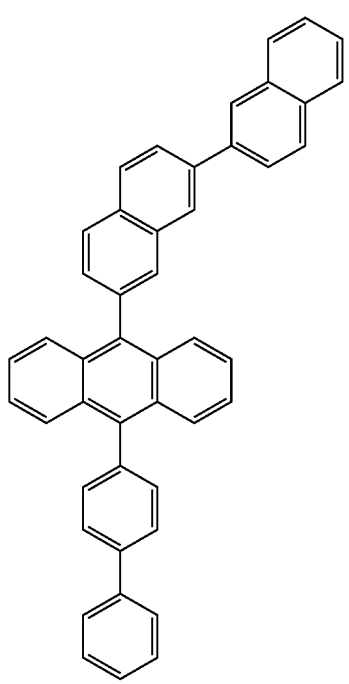
(1-130)
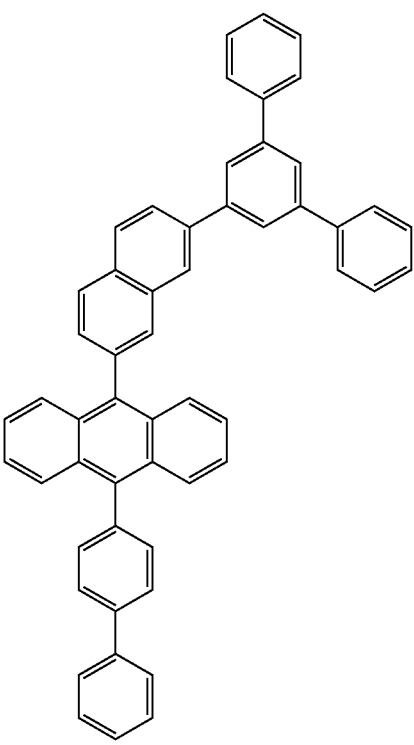
(1-131)
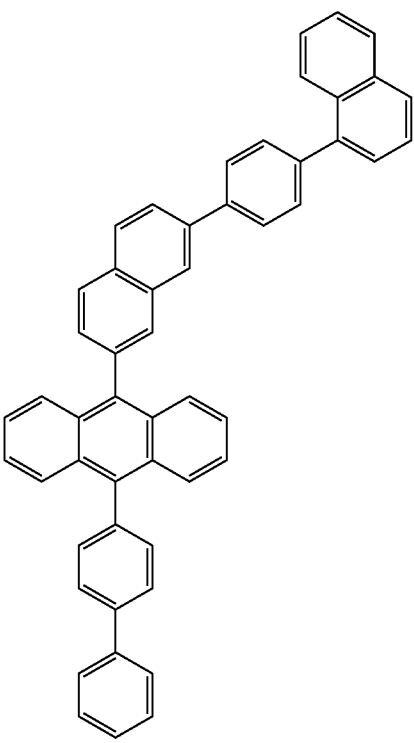

(1-132)
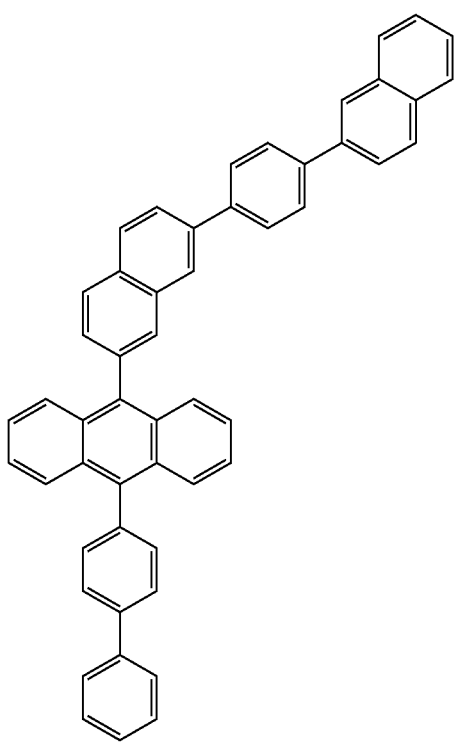
(1-134)
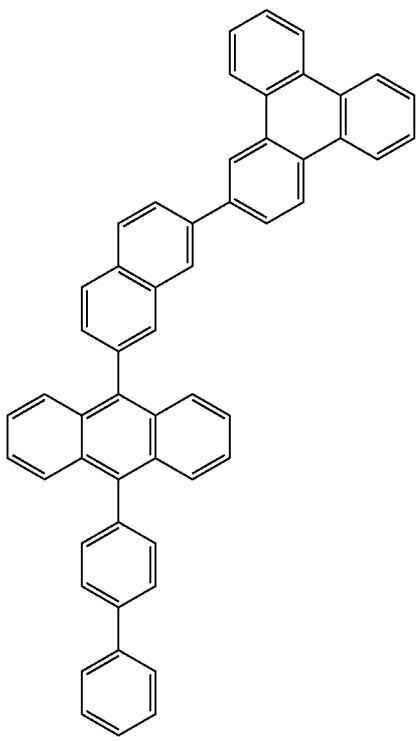
(1-133)
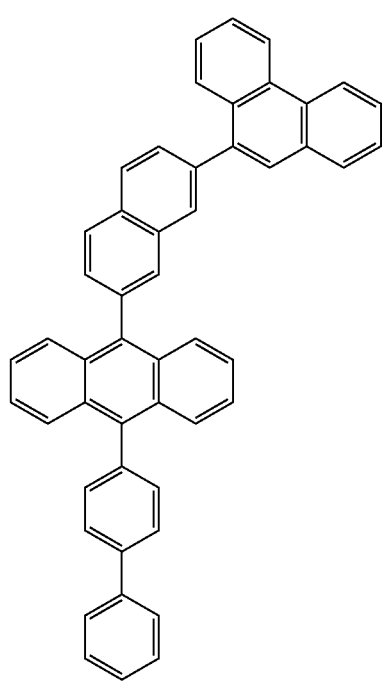
(1-135)
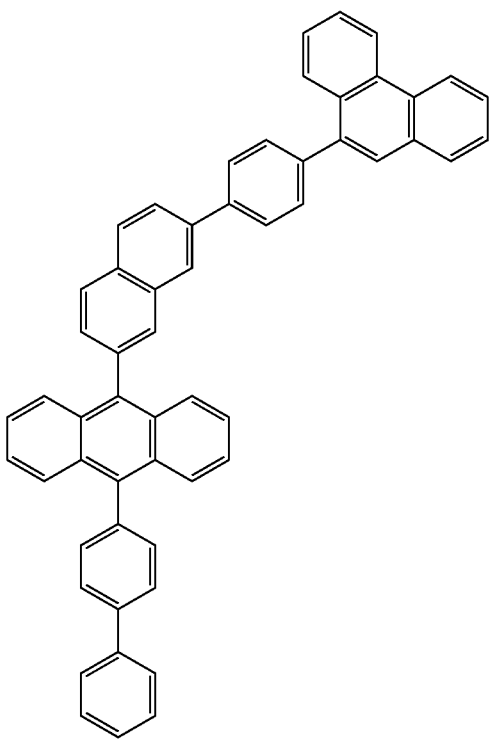

[Formula 24]
(1-136)
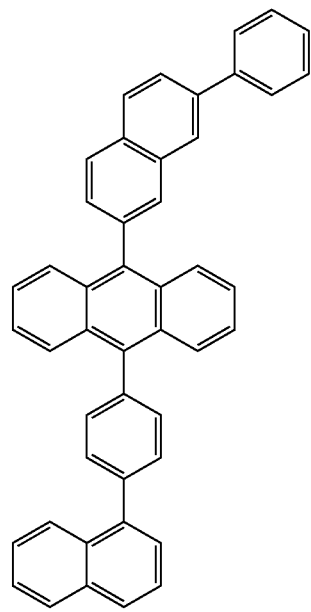
(1-137)
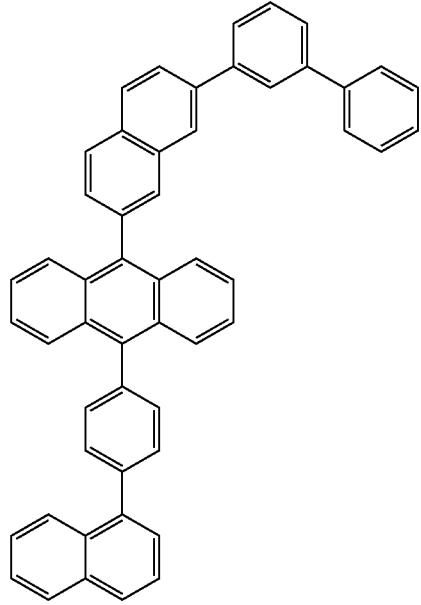
(1-138)
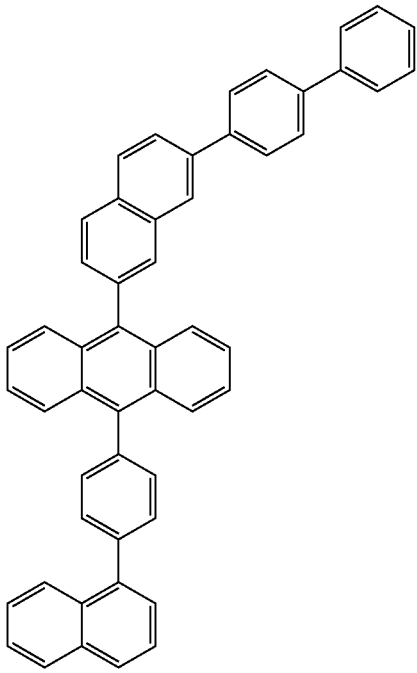
(1-139)
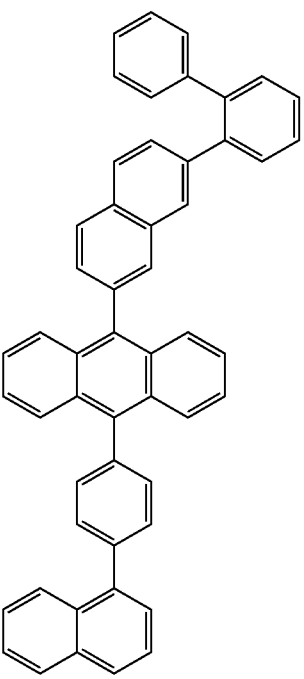

(1-140)
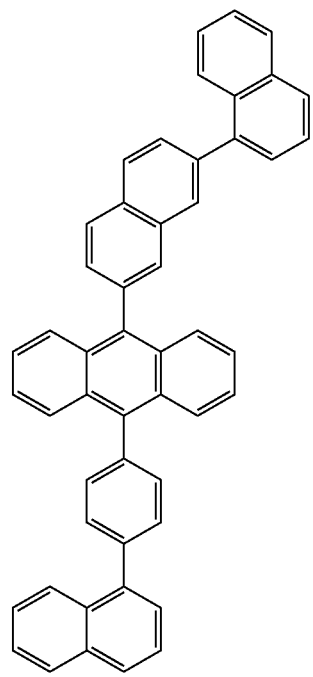
(1-142)
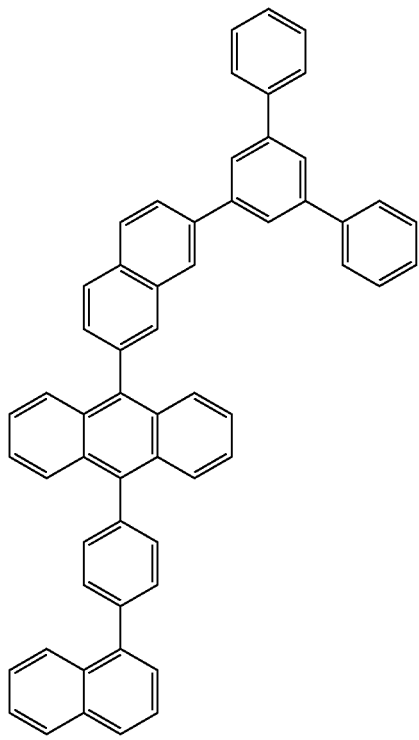
(1-141)
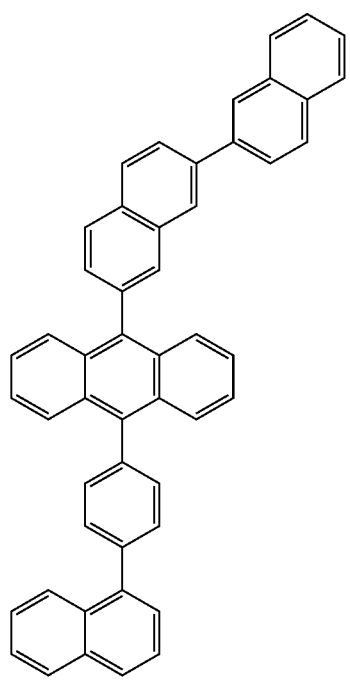
(1-143)
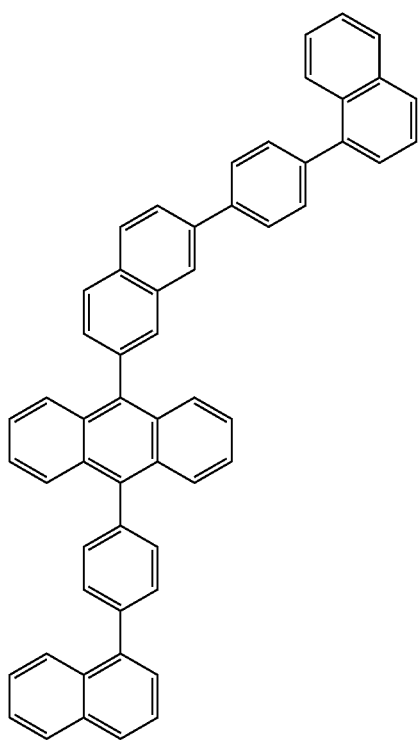

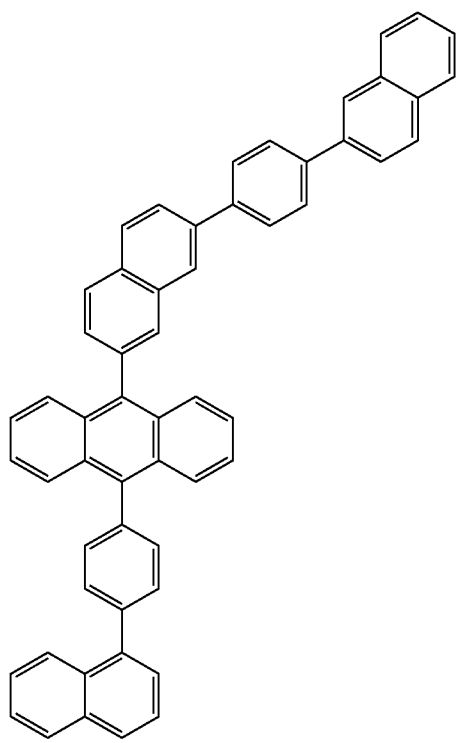
(1-144)
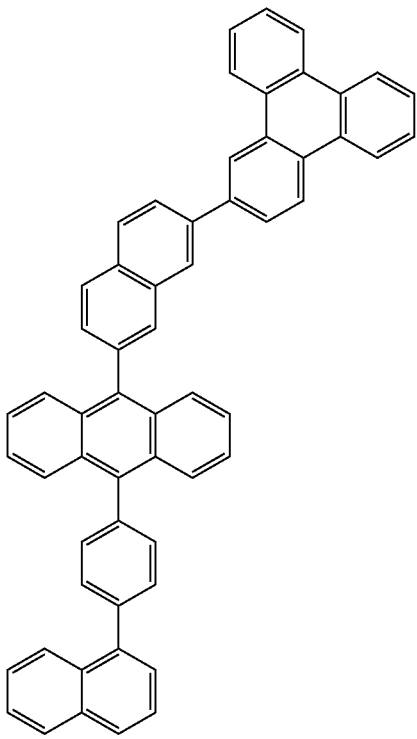
(1-146)
[Formula 25]
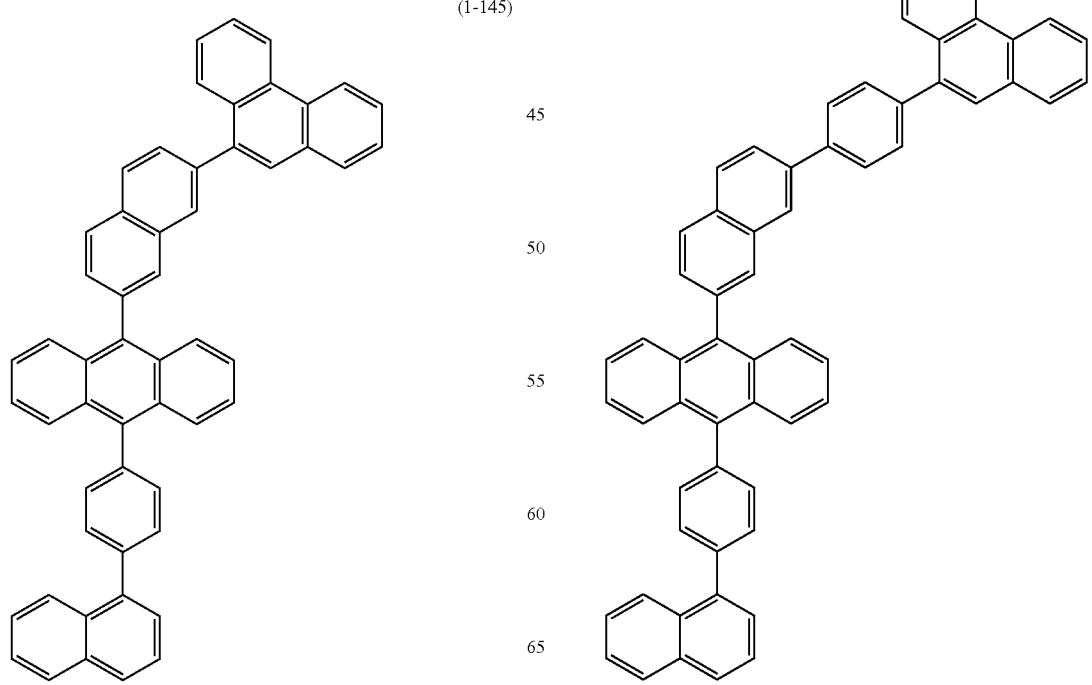
(1-145)
(1-147)

(1-148)
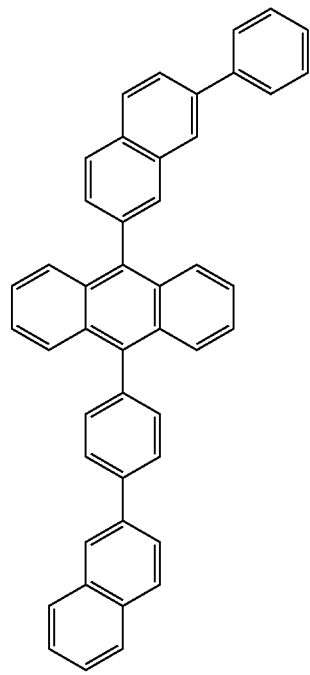
(1-150)
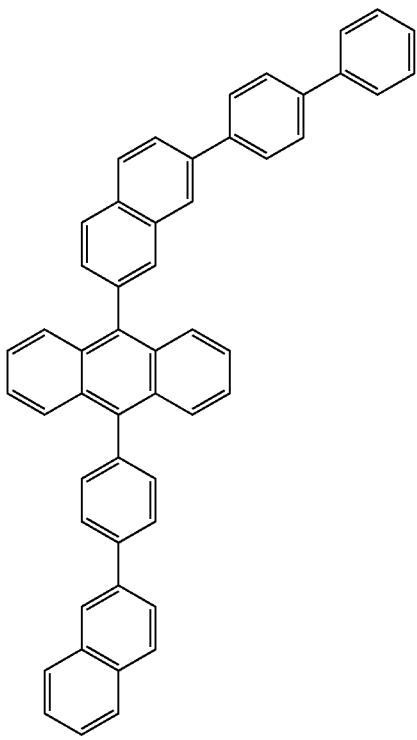
(1-149)
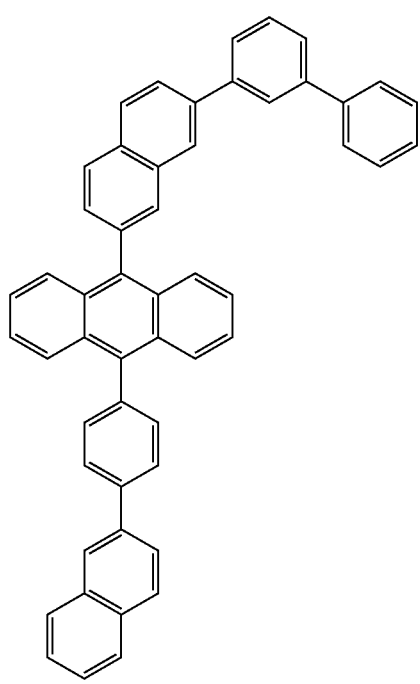
(1-151)
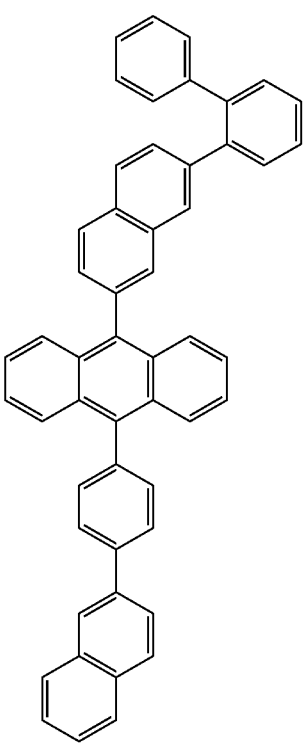

(1-152)
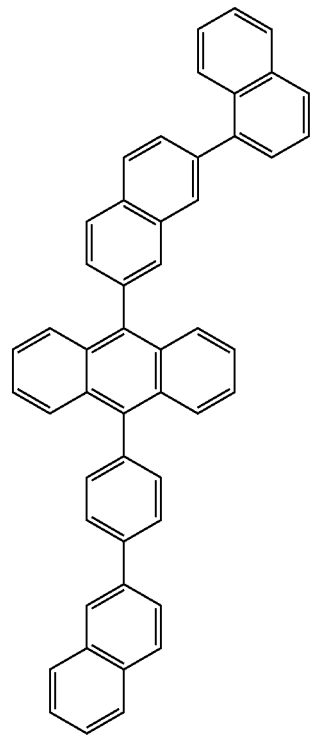
[Formula 26]
(1-154)
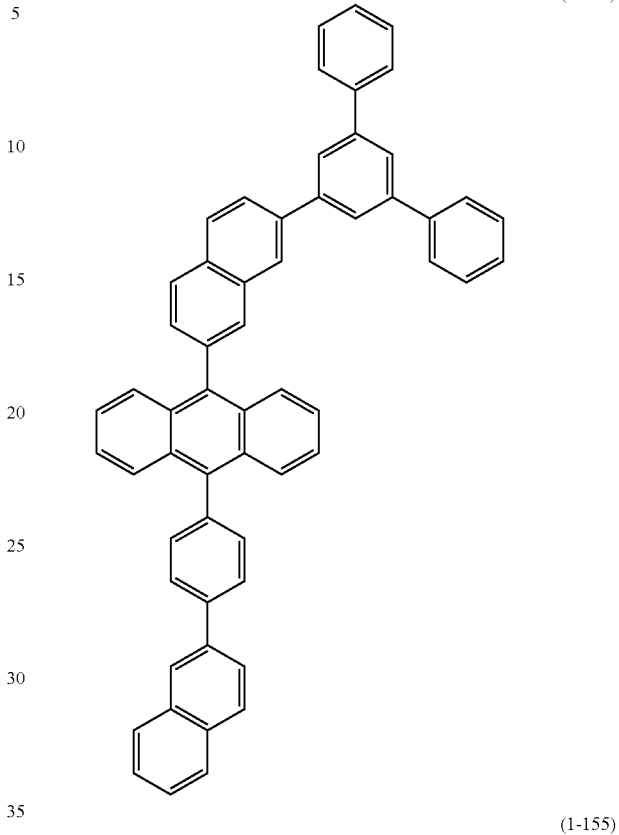
(1-153)
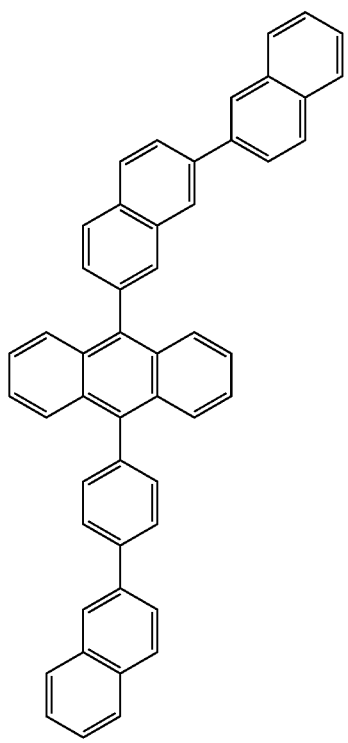
(1-155)
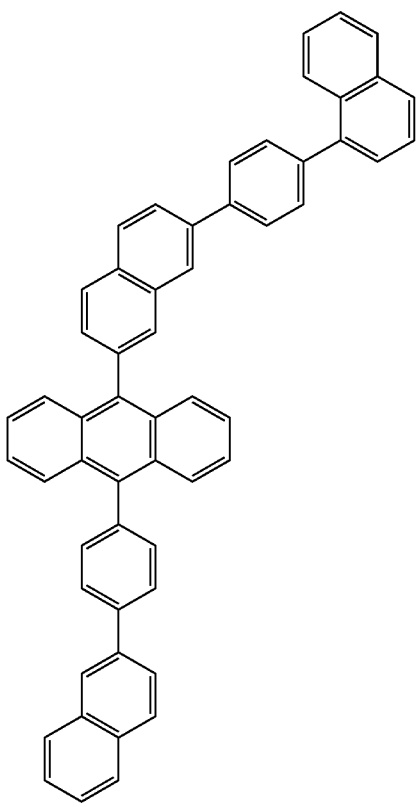

(1-156)
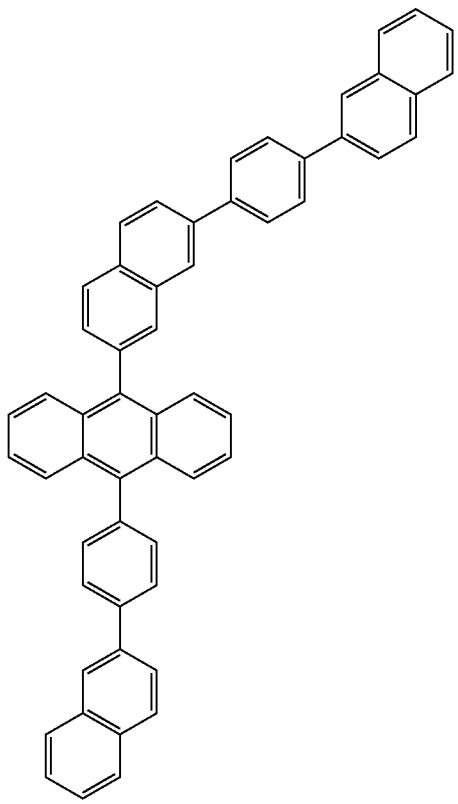
(1-158)
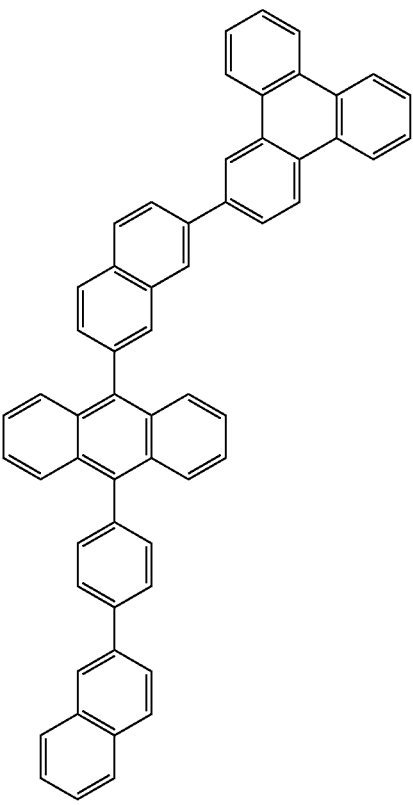
(1-157)
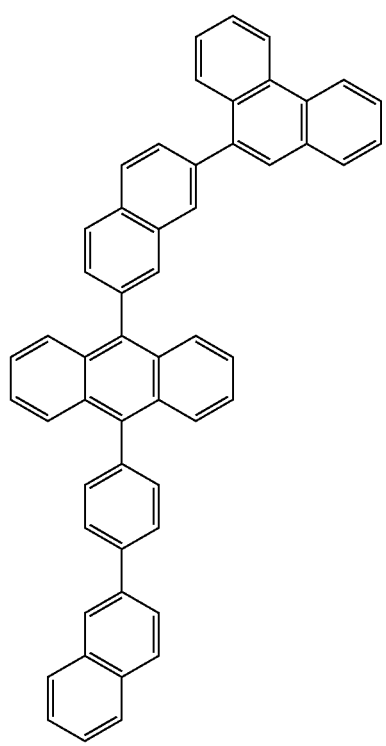
(1-159)
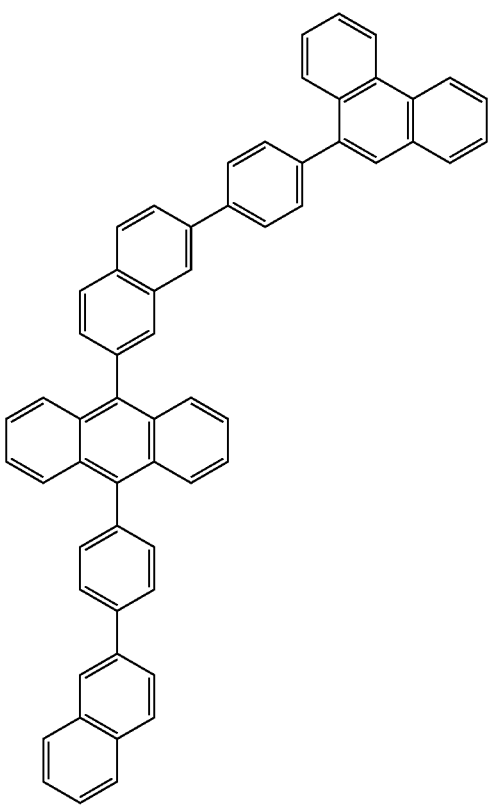

[Formula 27]
(1-160)
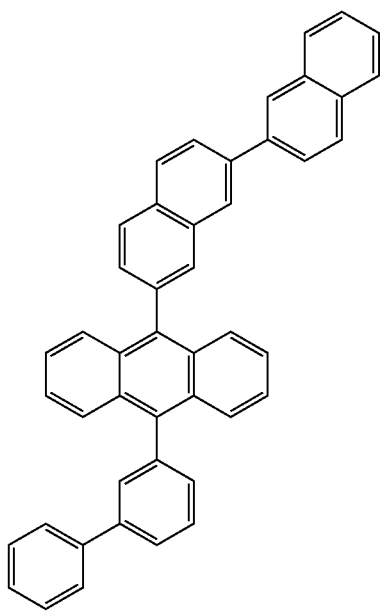
(1-161)
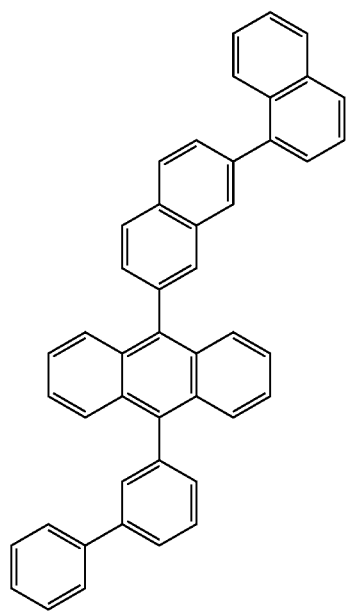
(1-162)
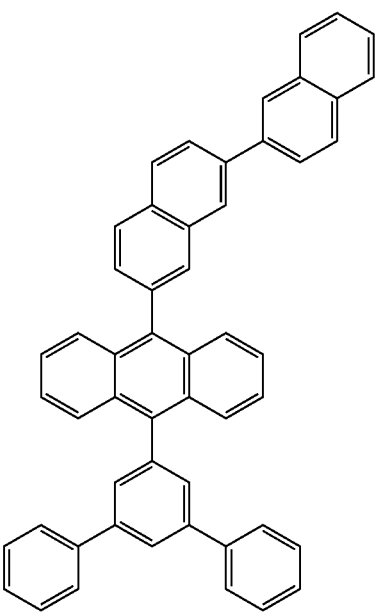
(1-163)
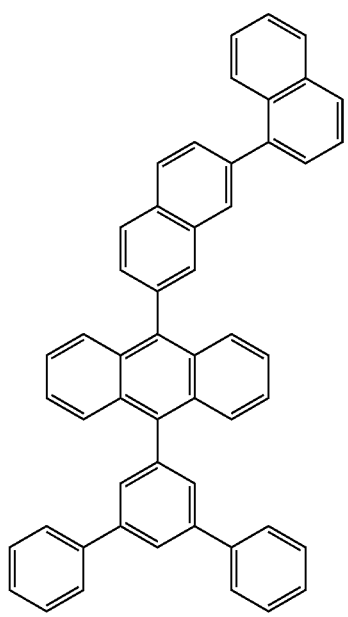

(1-164)
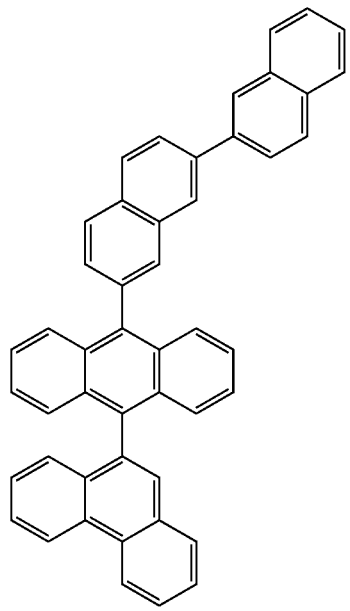
(1-166)
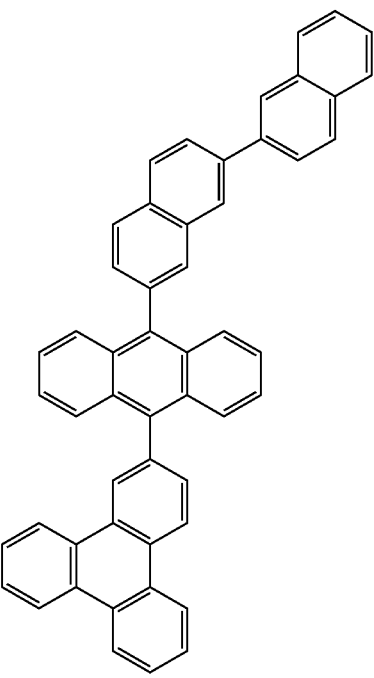
(1-165)
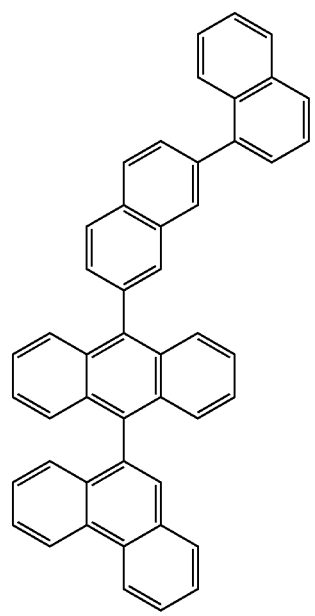
(1-167)
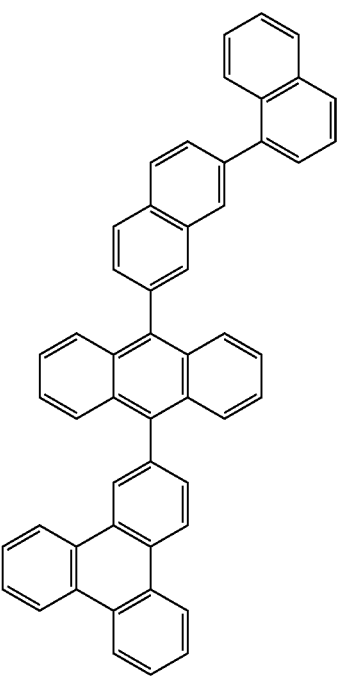

[Formula 28]
(1-168)
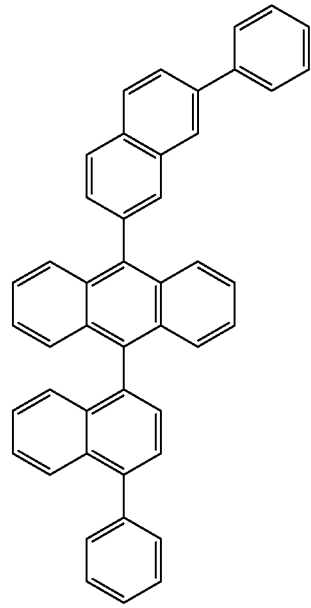
(1-169)
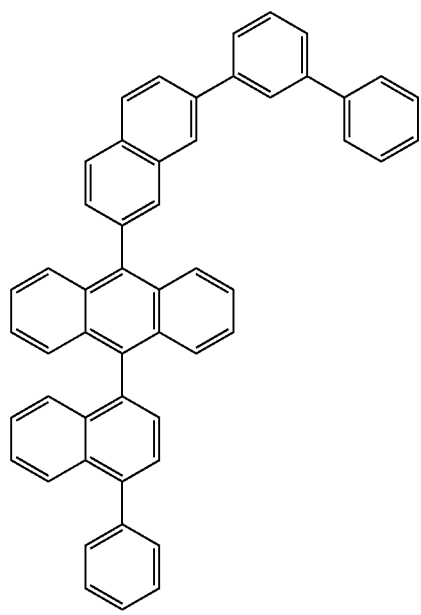
(1-170)
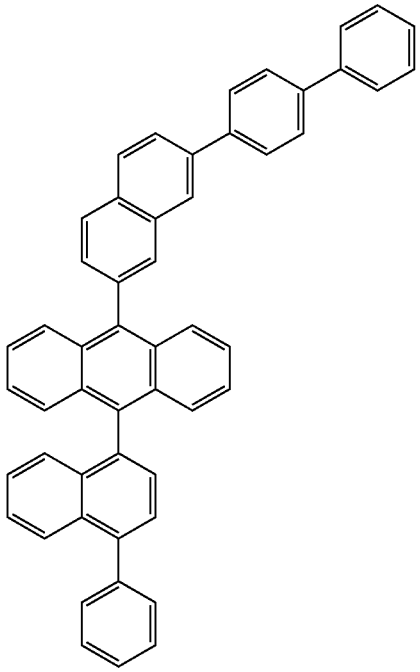
(1-171)
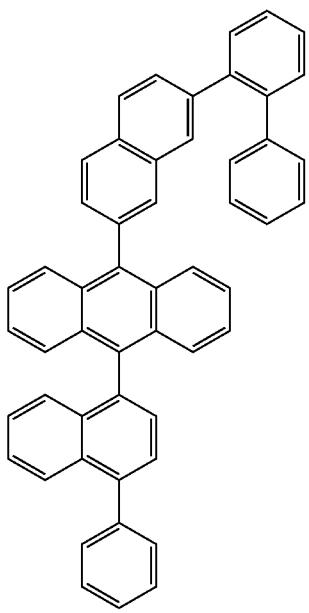

(1-172)
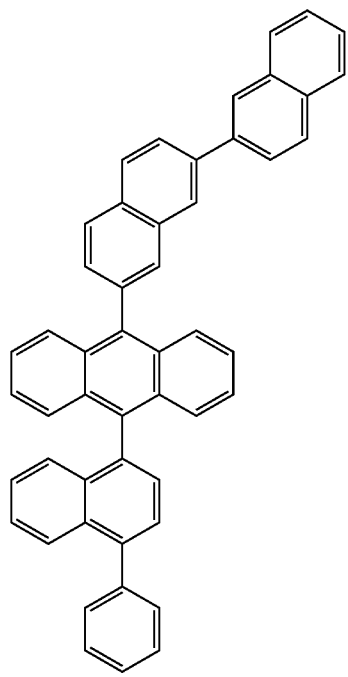
(1-173)
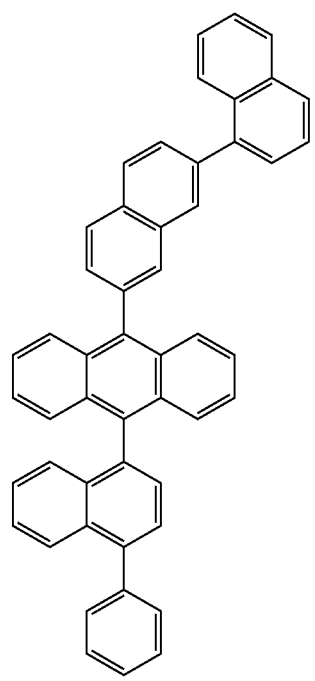
(1-174)
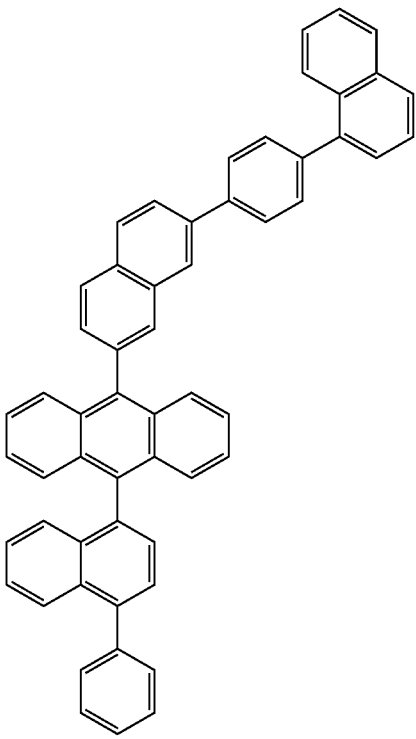
(1-175)
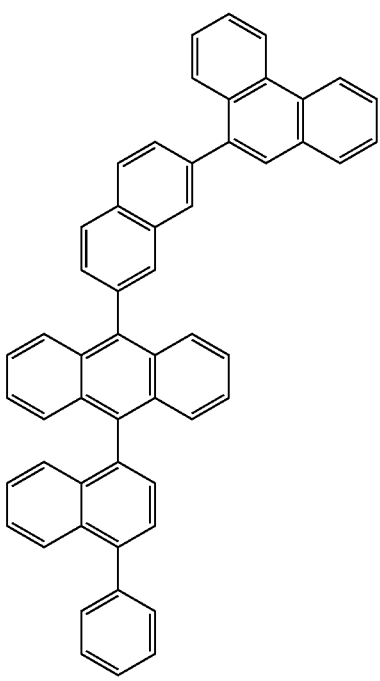

(1-176)
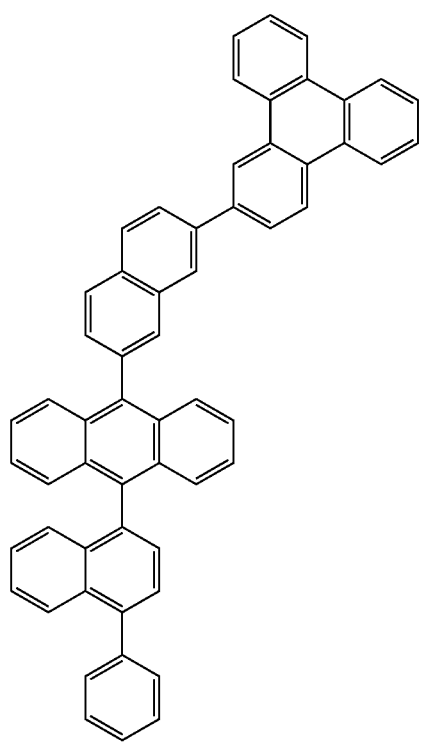
(1-178)
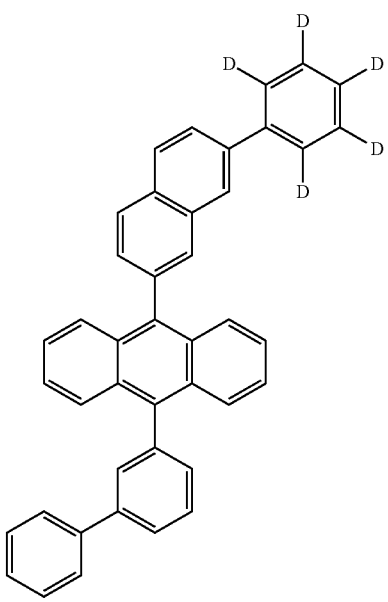
[Formula 29]
(1-177)
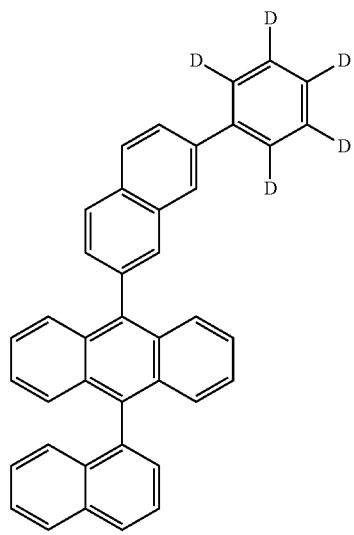
(1-179)
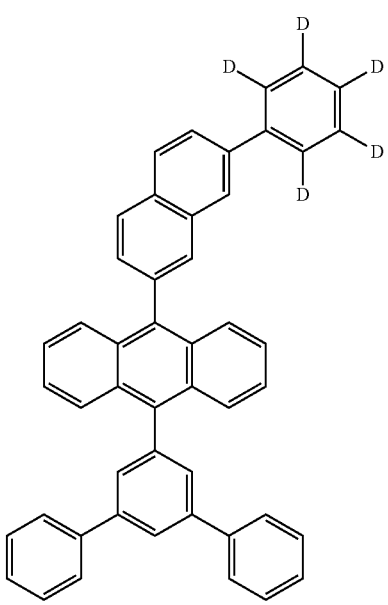

(1-180)
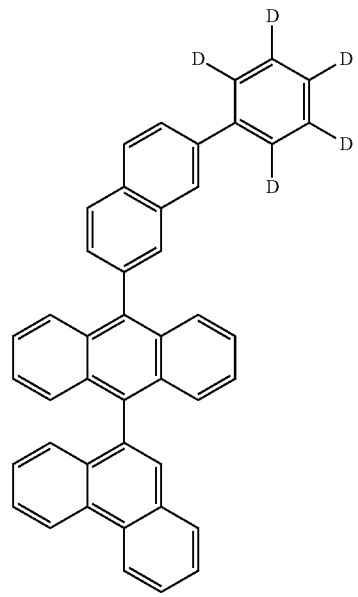
(1-181)
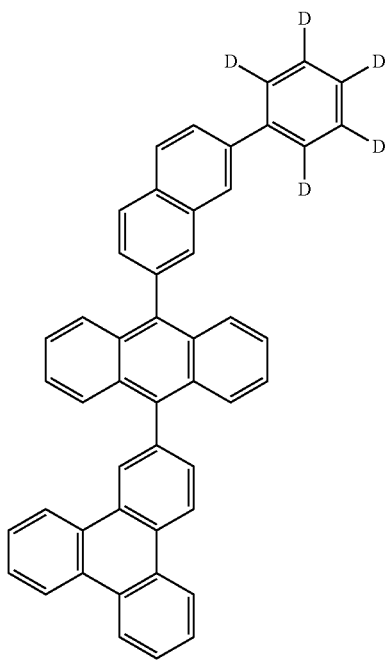
(1-182)
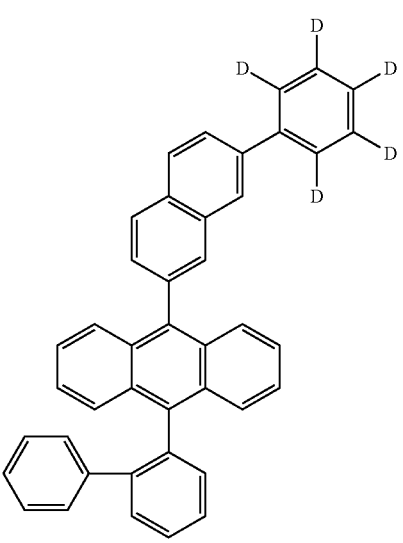
(1-183)
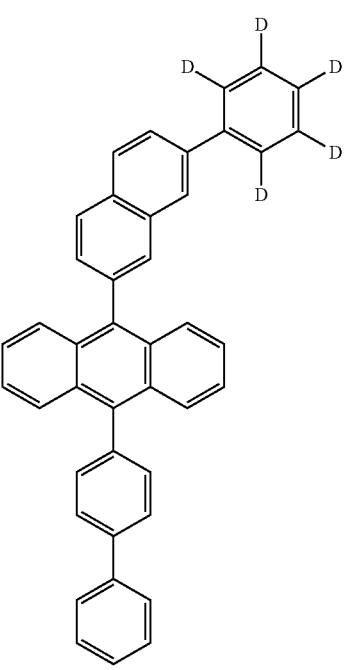

(1-184)

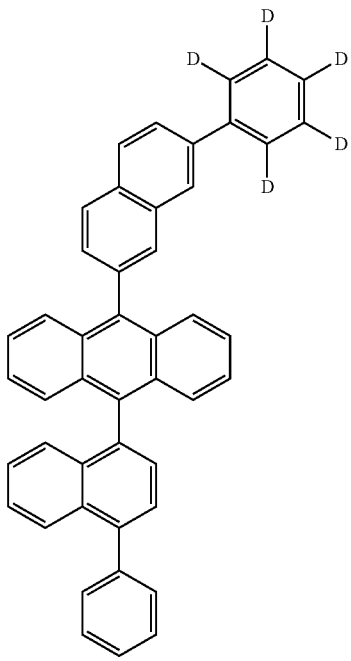

2. Method for Producing Anthracene Compound Represented by Formula (1)

The anthracene compound represented by Formula (1) can be produced by a known synthesis method. For example, it may be synthesized according to the pathway represented by the following reactions (A-1) to (A-3). It may be also synthesized according to the pathway represented by the following reactions (B-1) to (B-5).

First, the pathway represented by the reactions (A-1) to (A-3) will be described. First, according to the reaction (A-1), 2,7-naphthalene diol is reacted with trifluoromethane sulfonic acid anhydride in the presence of a base to synthesize naphthalene-2,7-diyl bis(trifluoromethane sulfonate).

Reaction (A-1)

[Formula 30]

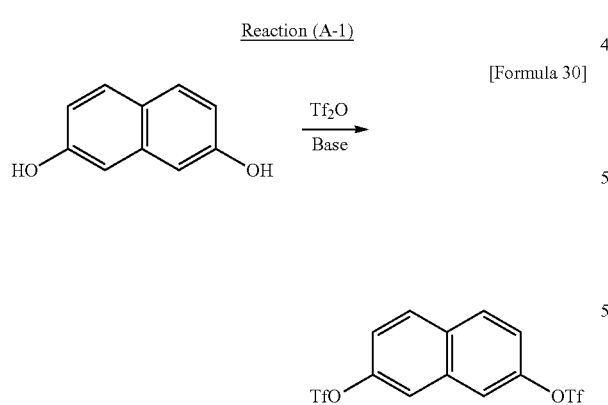

Next, according to the reaction (A-2), Suzuki coupling reaction of naphthalene-2,7-diyl bis(trifluoromethane sulfonate) with 1 eqv. of aryl boronic acid ($Ar^2B(OH)_2$) using a palladium catalyst is performed in the presence of a base to synthesize naphthalene triflate having aryl ($Ar^2$). Further, the aryl ($Ar^2$) in arylboronic acid is the same as $Ar^2$ in Formula (1).

Reaction (A-2)

[Formula 31]

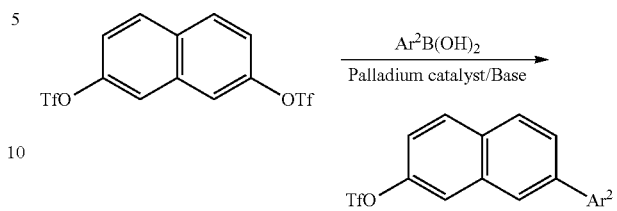

Finally, according to the reaction (A-3), Suzuki coupling reaction of naphthalene triflate having aryl with an anthracene boronic acid derivative substituted with $Ar^1$ using a palladium catalyst is performed in the presence of a base to synthesize the anthracene compound represented by Formula (1) of the invention. In addition, the anthracene boronic acid derivative substituted with $Ar^1$ can be obtained by a known reaction by using bromoanthracene substituted with $Ar^1$, which is obtained by various coupling reactions of 9,10-dibromoanthracne and a Grignard reagent and zinc complex synthesized from various aryl boronic acids and aryl halide. In addition, $Ar^1$ and the substituents ($R^1$ to $R^4$) are the same as $Ar^1$ and $R^1$ to $R^4$ in Formula (1).

Reaction (A-3)

[Formula 32]

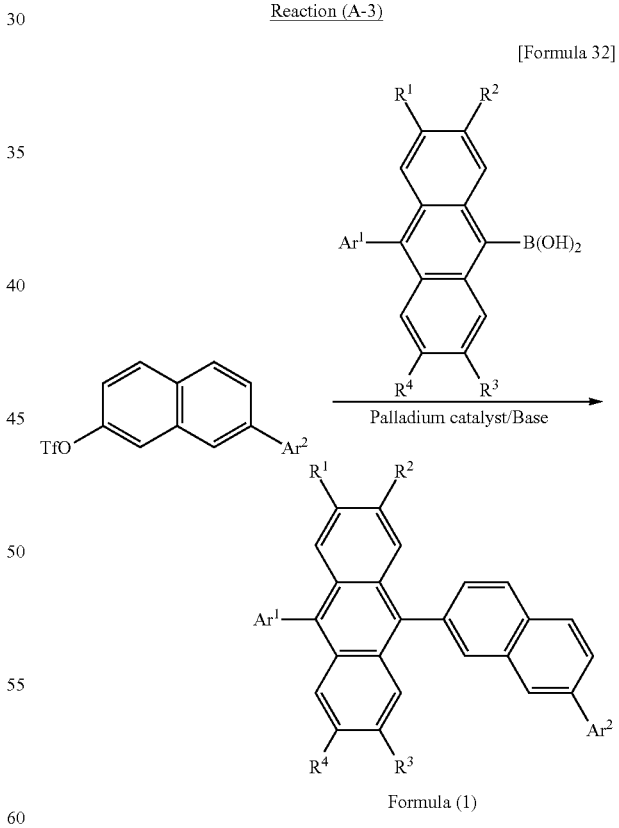

Formula (1)

Herein, in the reaction (A-3) step described above, it is possible to synthesize the anthracene compound represented by Formula (1) according to synthesis of an intermediate having no substitution at the 9-(10-) position by using 9-anthracene boronic acid instead of an anthracene boronic acid derivative substituted with $Ar^1$, bromination of the intermediate during the reaction (A-3') step, and Suzuki coupling with various aryl boronic acids during the reaction (A-3") step.

[Formula 33]

Reaction (A-3')

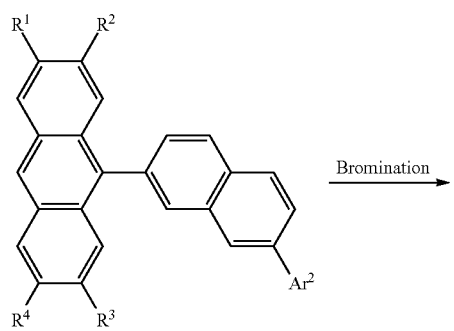

Bromination →

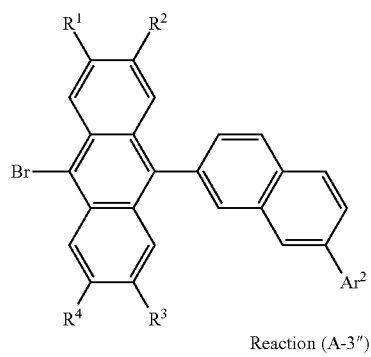

Reaction (A-3")

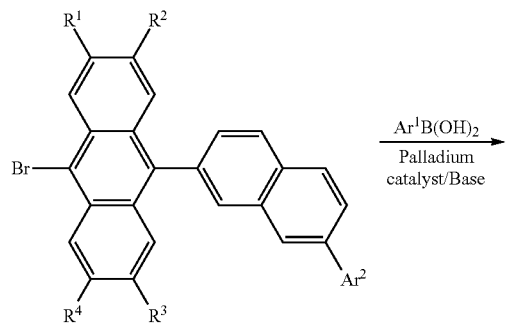

Ar¹B(OH)₂
Palladium catalyst/Base →

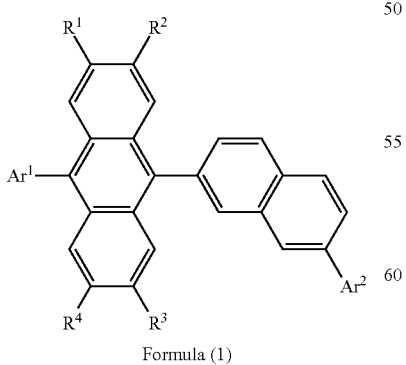

Formula (1)

Next, pathways represented by the reactions (B-1) to (B-5) will be described. First, according to the reaction (B-1), 7-methoxynaphthalen-2-yl trifluoromethane sulfonate can be synthesized by reacting 7-methoxy-2-naphthol with trifluoromethane sulfonic acid anhydride in the presence of base.

Reaction (B-1)

[Formula 34]

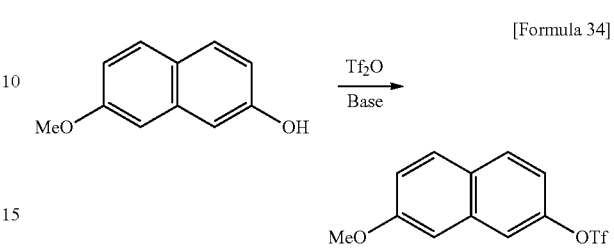

Next, according to the reaction (B-2), with Suzuki coupling reaction of 7-methoxynaphthalen-2-yl trifluoromethane sulfonate with an anthracene boronic acid derivative substituted with Ar¹ by using a palladium catalyst in the presence of a base, 9-(7-methoxynaphthalen-2-yl) anthracene derivative having the 10-position substituted with Ar¹ can be synthesized. Further, Ar¹ and the substituents ($R^1$ to $R^4$) are the same as Ar¹ and $R^1$ to $R^4$ in Formula (1).

Reaction (B-2)

[Formula 35]

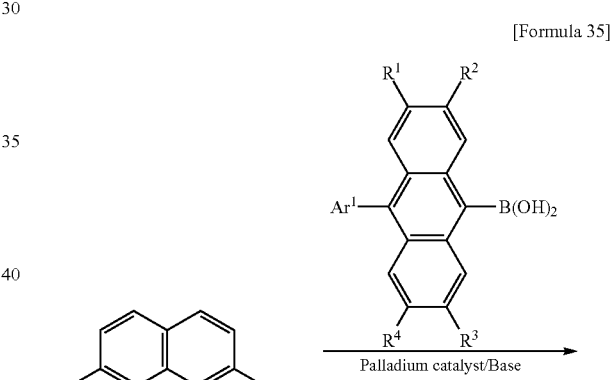

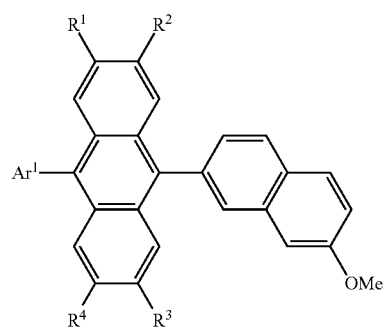

Next, according to the reaction (B-3), by reacting 9-(7-methoxynaphthalen-2-yl)anthracene derivative having the 10-position substituted with Ar¹ with pyridine hydrochloride and performing demethylation, a naphthol derivative can be synthesized. At that time, NMP or the like may be used as a solvent.

Reaction (B-3)

[Formula 36]

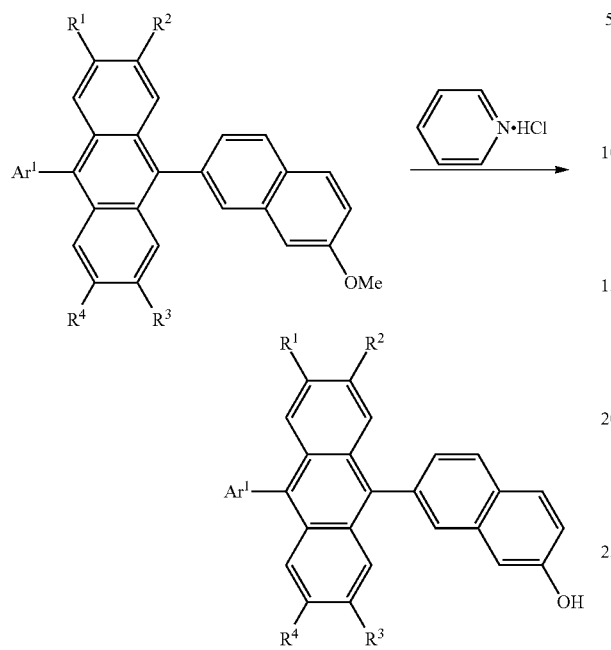

Further, according to the reaction (B-4), by reacting the naphthol derivative obtained by the reaction (B-3) with trifluoromethane sulfonic acid anhydride, naphthalene triflate having an anthracene derivative substituted with $Ar^1$ can be synthesized.

Reaction (B-4)

[Formula 37]

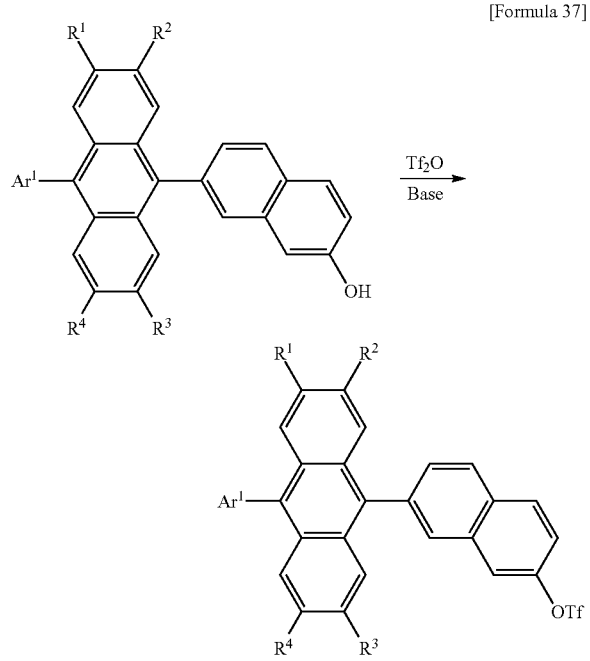

Finally, in the reaction (B-5), by Suzuki coupling reaction of naphthalene triflate having an anthracene derivative substituted with $Ar^1$, which is obtained according to the reaction (B-4), with aryl boronic acid ($Ar^2B(OH)_2$) by using a palladium catalyst in the presence of a base, the anthracene compound represented by Formula (1) of the invention can be synthesized. In addition, aryl ($Ar^2$) in the aryl boronic acid is the same as $Ar^2$ in Formula (1).

Reaction (B-5)

[Formula 38]

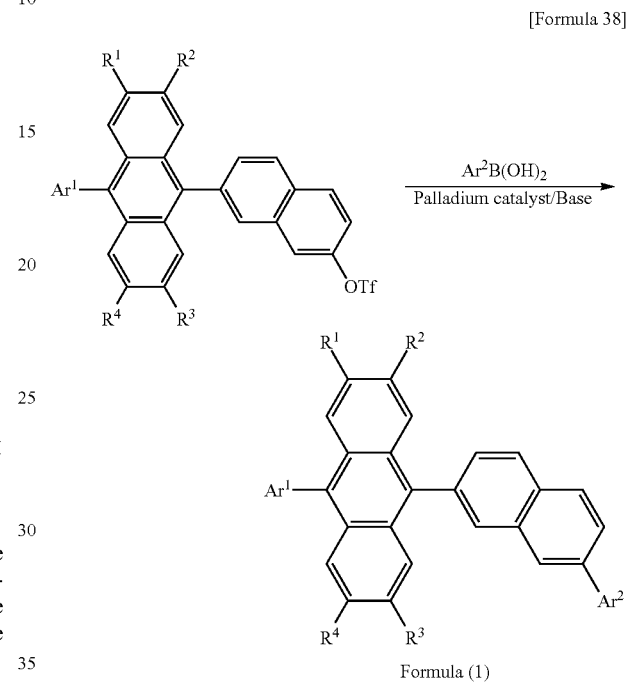

Formula (1)

When a palladium catalyst is used for the reaction (A-2), the reaction (A-3), the reaction (A-3"), the reaction (B-2), and the reaction (B-5) described above, $Pd(PPh_3)_4$, $PdCl_2(PPh_3)_2$, $Pd(OAc)_2$, bis(dibenzylideneacetone)palladium (O) (Pd (dba)$_2$)), tris(dibenzylideneacetone)dipalladium (O), tris(dibenzylideneacetone)dipalladium chloroform complex (O), [1.1'-bis(diphenylphosphino) ferrocene]palladium (II) dichloride dichloromethane complex (1:1), or the like may be used, for example.

A phosphine compound may, if appropriate, be added to these palladium compounds for acceleration of reaction. Examples of a phosphine compound include tri(t-butyl)phosphine, tricyclo hexylphosphine, 1-(N,N-dimethylamino methyl)-2-(di-tert-butylhosphino) ferrocene, 1-(N,N-dibutylaminomethyl)-2-(di-tert-butylhosphino)ferrocene, 1-(methoxymethyl)-2-(di-tert-butylhosphino)ferrocene, 1,1'-bis(di-tert-butylhosphino) ferrocene, 2,2'-bis(di-tert-butylhosphino)-1,1'-binaphthyl, and 2-methoxy-2'-(di-tert-butylhosphino)-1,1'-binaphthyl.

Examples of a base used with a palladium catalyst include sodium carbonate, potassium carbonate, cesium carbonate, sodium hydrogen carbonate, sodium hydroxide, potassium hydroxide, barium hydroxide, sodium ethoxide, sodium t-butoxide, sodium acetate, potassium acetate, tripotassium phosphate, and potassium fluoride.

Further, examples of the solvent used for the reaction (A-2), the reaction (A-3), the reaction (B-2), and the reaction (B-5) described above include benzene, toluene, xylene, N,N-dimethyl formamide, tetrahydrofuran, diethyl ether, t-butyl methyl ether, 1,4-dixoane, methanol, ethanol, isopropyl alcohol, and cyclopentyl methyl ether. The solvent may be used either singly or as mixed solvent. The reaction is generally performed in the temperature range of 50 to 180° C., and more preferably 70 to 130° C.

Where a base is used in a reaction (A-1), a reaction (B-1), and a reaction (B-4), for example, sodium carbonate, potassium carbonate, cesium carbonate, sodium hydrogen carbonate, sodium hydroxide, potassium hydroxide, barium hydroxide, sodium acetate, potassium acetate, tripotassium phosphate, potassium fluoride, cesium fluoride, trimethylamine, triethylamine, and pyridin, can be used.

Further, examples of the solvent used for the reaction (A-1), the reaction (B-1), and the reaction (B-4) include pyridine, toluene, xylene, N,N-dimethyl formamide, N,N-dimethyl acetamide, $CH_2Cl_2$, and $CHCl_3CH_3CN$. The solvent may be used either singly or as mixed solvent. The reaction is generally performed in the temperature range of −10 to 50° C., and more preferably 0 to 30° C.

When an acid catalyst is used for the reaction (B-3), an inorganic acid such as sulfuric acid, hydrochloric acid, and polyphosphoric acid, an organic acid such as methane sulfonic acid and trifluoromethane sulfonic acid, and Lewis acid such as silica gel, alumina, $BF_3.OEt_2$, $AlCl_3$, $AlBr_3$, $EtAlCl_2$, and $Et_2AlCl$ can be used. Further, examples of the reaction solvent include acetic acid, $CH_2Cl_2$, $CHCl_3$, nitrobenzene, and $CS_2$. The reaction is generally performed in the temperature range of −70 to 150° C., and more preferably −10 to 100° C.

Further, examples of the reaction solvent used for the reaction (B-3) include 1-methyl-2-pyrrolidone, N,N-dimethyl acetamide, nitrobenzene, dimethyl sulfoxide, dichlorobenzene, and quinoline. The solvent may be used either singly or as mixed solvent. Depending on a case, a solvent-free system may be used. The reaction is generally performed in the temperature range of 150 to 220° C., and more preferably 180 to 200° C.

Further, the compounds of the invention include those in which at least part of the hydrogen atoms are substituted with deuterium. Such compounds can be synthesized as described above by using a raw material having a deuterium at desired position.

3. Organic Electroluminescence Element

The anthracene compound according to the invention can be used as a material of an organic electroluminescence element, for example. Hereinafter, the organic electroluminescence element according to the present embodiment will be described in detail in view of the drawings. FIG. 1 is a schematic cross-sectional view illustrating the organic electroluminescence element according to the present embodiment.

<Structure of Organic Electroluminescence Element>

An organic electroluminescence element 100 illustrated in FIG. 1 has a substrate 101, a positive electrode 102 provided on the substrate 101, a hole injection layer 103 provided on the positive electrode 102, a hole transport layer 104 provided on the hole injection layer 103, a light emitting layer 105 provided on the hole transport layer 104, an electron transport layer 106 provided on the light emitting layer 105, an electron injection layer 107 provided on the electron transport layer 106, and a negative electrode 108 provided on the electron injection layer 107.

With the fabrication method the other way around, the organic electroluminescence element 100 may have a structure in which it has the substrate 101, the negative electrode 108 provided on the substrate 101, the electron injection layer 107 provided on the negative electrode 108, the electron transport layer 106 provided on the electron injection layer 107, the light emitting layer 105 provided on the electron transport layer 106, the hole transport layer 104 provided on the light emitting layer 105, the hole injection layer 103 provided on the hole transport layer 104, and the positive electrode 102 provided on the hole injection layer 103.

All the respective layers described above do not necessarily have to be present, and the hole injection layer 103, the hole transport layer 104, the electron transport layer 106 and the electron injection layer 107 are layers which are optionally provided, in which a minimum structural unit is assumed as a structure formed by the positive electrode 102, the light emitting layer 105 and negative electrode 108. The respective layers described above each may be formed by a single layer or plural layers.

The mode of the layers constituting the organic electroluminescence element may be, in addition to the structural mode of "substrate/positive electrode/hole injection layer/hole transport layer/light emitting layer/electron transport layer/electron injection layer/negative electrode" described above, the structural modes of "substrate/positive electrode/hole transport layer/light emitting layer/electron transport layer/electron injection layer/negative electrode", "substrate/positive electrode/hole injection layer/light emitting layer/electron transport layer/electron injection layer/negative electrode", "substrate/positive electrode/hole injection layer/hole transport layer/light emitting layer/electron injection layer/negative electrode", "substrate/positive electrode/hole injection layer/hole transport layer/light emitting layer/electron transport layer/negative electrode", "substrate/positive electrode/light emitting layer/electron transport layer/electron injection layer/negative electrode", "substrate/positive electrode/hole transport layer/light emitting layer/electron injection layer/negative electrode", "substrate/positive electrode/hole transport layer/light emitting layer/electron transport layer/negative electrode", "substrate/positive electrode/hole injection layer/light emitting layer/electron injection layer/negative electrode", "substrate/positive electrode/hole injection layer/light emitting layer/electron transport layer/negative electrode", "substrate/positive electrode/light emitting layer/electron transport layer/negative electrode", or "substrate/positive electrode/light emitting layer/electron injection layer/negative electrode".

<Substrate of Organic Electroluminescence Element>

The substrate 101 is a base for the organic electroluminescence element 100, and quartz, glass, metal and plastics are usually used therefor. The substrate 101 is formed in the shape of a plate, a film or a sheet according to the purposes, and a glass plate, a metal plate, a metal foil, a plastic film or a plastic sheet is used. Among them, a glass plate and a plate made of a transparent synthetic resin such as polyester, polymethacrylate, polycarbonate and polysulfone are preferred. Soda lime glass, non-alkali glass and the like are used for the glass substrate. The thickness thereof may be such a thickness as enough for maintaining the mechanical strength, and therefore it is 0.2 mm or more. An upper limit value of the thickness is 2 mm or less, preferably 1 mm or less. The material of glass is preferably non-alkali glass since ions eluted from glass are preferably smaller. Soda lime glass which is provided with a barrier coat such as $SiO_2$ is commercially available, and therefore it can be used. The substrate 101 may be provided at least on one face thereof with a gas barrier film such as a dense silicon oxide film in order to enhance gas barrier property thereof. Particularly when a plate, a film or a sheet made of a synthetic resin having low gas barrier property is used for the substrate 101, a gas barrier film is preferably provided thereon.

<Positive Electrode of Organic Electroluminescence Element>

The positive electrode 102 plays a role of injecting holes into the light emitting layer 105. When the hole injection layer 103 and/or the hole transport layer 104 are provided between the positive electrode 102 and the light emitting layer 105, holes are injected into the light emitting layer 105 via these layers.

A material for forming the positive electrode 102 includes inorganic compounds and organic compounds. The inorganic compounds include, for example, metals (aluminum, gold, silver, nickel, palladium, chromium and the like), metal oxides (oxide of indium, oxide of tin, indium-tin oxide (ITO), indium-zinc oxide (IZO), and the like), halogenated metals (copper iodide and the like), copper sulfide, carbon black, ITO glass, nesa glass, and the like. The organic compounds include, for example, polythiophene such as poly(3-methylthiophene) and electrically conductive polymers such as polypyrrole, polyaniline and the like. In addition thereto, those suitably selected from materials used for a positive electrode of an organic electroluminescence element can be used.

A resistance of the transparent electrode shall not be restricted as long as an electric current sufficient for emission of the light emitting element can be supplied, and it is preferably a low resistance from the viewpoint of power consumption of the light emitting element. For example, an ITO substrate having a resistance of 300Ω/□ or less functions as an element electrode. At present, a substrate having a resistance of about 10Ω/□ can be supplied, and therefore a product having a low resistance of 100 to 5Ω/□, preferably 50 to 5Ω/□ is particularly preferably used. A thickness of ITO can optionally be selected depending on a resistance value thereof, and it is usually used in a range of 50 to 300 nm in many cases.

<Hole Injection Layer and Hole Transport Layer of Organic Electroluminescence Element>

The hole injection layer 103 plays a role of efficiently injecting holes moving from the positive electrode 102 into the light emitting layer 105 or the hole transport layer 104. The hole transport layer 104 plays a role of efficiently transporting holes injected from the positive electrode 102 or holes injected from the positive electrode 102 via the hole injection layer 103 into the light emitting layer 105. The hole injection layer 103 and the hole transport layer 104 are formed respectively by laminating or mixing at least one of hole injecting and transporting materials or from a mixture of the hole injecting and transporting material with a high molecular binder. Further, inorganic salt such as iron chloride (III) may be added to the hole injecting and transporting material to form the layers.

The hole injecting and transporting material has to efficiently inject and transport holes from a positive electrode between the electrodes to which an electrical field is applied, and it is desirable that the hole injection efficiency be high and that the holes injected be efficiently transported. Accordingly, preferred is the material which has small ionization potential and large hole mobility and excellent stability and in which impurities trapped are less liable to be generated during production and use.

Optional compounds selected from compounds which have so far conventionally been used as an electron transport material of a hole in a photoconductive material, p type semiconductors and known compounds used for a hole injection layer and a hole transport layer in an organic electroluminescence element can be used as materials for forming the hole injection layer 103 and the hole transport layer 104. The specific examples thereof include carbazole derivatives (N-phenylcarbazole, polyvinylcarbazole and the like), biscarbazole derivatives such as bis(N-allylcarbazole) and bis (N-alkylcarbazole), triarylamine derivatives (polymers having aromatic tertiary amine on a principal chain or a side chain), triphenylamine derivatives such as 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-diphenyl-1,1'-diamine and 4,4',4"-tris(3-methylphenyl(phenyl)amino)triphenylamine, star burst amine derivatives and the like), stilbene derivatives, heterocyclic compounds such as phthalocyanine derivatives (non-metal phthalocyanines, copper phthalocyanine and the like), pyrazoline derivatives, hydrazone compounds, benzofuran derivatives, thiophene derivatives, oxadiazole derivatives and porphyrin derivatives, polysilane and the like. Among the polymer compounds, polycarbonate, styrene derivatives, polyvinylcarbazole, polysilane and the like which have the monomers described above on side chains are preferred, but they shall not specifically be restricted as long as they are compounds which can form a thin film necessary for preparing a light emitting element and which can inject holes from a positive electrode and can transport the holes.

It is known as well that an electrical conductivity of an organic semiconductor is strongly influenced by doping thereof. Such organic semiconductor matrix substance is constituted from a compound having good electron donating property or a compound having good electron accepting property. Strong electron acceptors such as tetracyanoquinone dimethane (TCNQ) or 2,3,5,6-tetrafluorotetracyano-1,4-benzoquinone dimethane (F4TCNQ) are known for doping electron donating substances (see, for example, the literature "M. Pfeiffer, A. Beyer, T. Fritz, K. Leo, Appl. Phys. Lett., 73 (22), 3202 to 3204 (1998)" and the literature "J. Blochwitz, M. Pheiffer, T. Fritz, K. Leo, Appl. Phys. Lett., 73 (6), 729 to 731 (1998)"). They produce so-called holes by an electron moving process in an electron donating type base material (hole transport material). The conductivity of the base material is changed to a considerably large extent by the number and mobility of holes. Known as a matrix substance having hole transport property are, for example, benzidine derivatives (TPD and the like), starburst amine derivatives (TDATA and the like) and specific metal phthalocyanines (particularly zinc phthalocyanine (ZnPc) and the like) (JP-A No. 2005-167175).

<Light Emitting Layer of Organic Electroluminescence Element>

The light emitting layer 105 emits light by re-binding of holes injected from the positive electrode 102 and the electrons injected from the negative electrode 108 between the electrodes applied with electric field. It is sufficient that the material constituting the light emitting layer 105 is a compound capable of emitting light by excitation caused by re-binding between holes and electrons (i.e., light emitting compound). It is preferably a compound which is capable of forming a stable thin film shape and exhibiting strong light emission (fluorescence) efficiency in solid state. In the invention, the compound represented by Formula (1) can be used as a material for light emitting layer.

The light emitting layer may have either a single layer or plural layers and each may be formed of a light emitting layer material (host material and dopant material). Each of host material and dopant material may be used either singly or in combination of two or more. The dopant material may be contained in either the whole part or a part of the host material. In a doping method, it can be formed by a method of co-depositing with the host material, and it is possible to mix in advance with the host material and then deposited at the same time.

The amount of the host material used varies depending on the type of the host material, and it can be determined in view of the properties of the host material. The standard use amount of the host material is preferably 50 to 99.999% by weight, more preferably 80 to 99.95% by weight, and still more preferably 90 to 99.9% by weight relative to entire light emitting layer material. In particular, the compound represented by Formula (1) of the invention is preferably used as a host material.

The amount of the dopant material used varies depending on the type of the dopant material, and it can be determined in view of the properties of the dopant material. The standard use amount of the dopant material is preferably 0.001 to 50% by weight, more preferably 0.05 to 20% by weight, and still more preferably 0.1 to 10% by weigh by weight relative to entire light emitting layer material. When it is within the above range, it is preferable from the viewpoint that a concentration quenching phenomenon can be prevented, for example.

Examples of the host material which may be used in combination with the compound represented by Formula (1) of the invention include condensed ring derivatives such as anthracene and pyrene which have so far been known as an emission material, bisstyryl derivatives such as bisstyryl anthracene derivatives and distyryl benzene derivatives, tetraphenylbutadiene derivatives, cyclopentadiene derivatives, fluorene derivatives, and benzofluorene derivatives.

As a dopant material, a known compound can be used without any particular limitation, and it can be chosen from various materials according to a desired luminescent color. Specifically, for example, a condensed-ring derivative such as phenanthrene, anthracene, pyrene, tetracene, pentacene, perylene, naphthpyrene, dibenzo-pyrene, rubrene, and chrysene, a benzoxazol derivative, a benzothiazole derivative, a benzimidazole derivative, a benzotriazole derivative, an oxazol derivative, an oxadiazol derivative, a thiazole derivative, imidazole derivative, a thiadiazole derivative, a triazole derivative, a pyrazoline derivative, a stilbene derivative, a thiophene derivative, a tetraphenyl butadiene derivative, a cyclopentadiene derivative, a bis styryl derivative such as a bis styryl anthracene derivative and a distyrylbenzen derivative (JP-A No. 1-245087), a bis styryl arylene derivative (JP-A No. 2-247278), a diaza indacene derivative, a furan derivative, a benzofuran derivative, an isobenzofuran derivative such as phenylisobenzofuran, dimesityl isobenzofuran, di(2-methylphenyl)isobenzofuran, di(2-trifluoromethyl phenyl)isobenzofuran, and phenylisobenzofuran, a dibenzofuran derivative, a coumarin derivative such as a 7-dialkyl amino coumarin derivative, a 7-piperidino coumarin derivative, a 7-hydroxy coumarin derivative, a 7-methoxy coumarin derivative, a 7-acetoxy coumarin derivative, a 3-benzthiazolyl coumarin derivative, a 3-benz imidazolyl coumarin derivative, and a 3-benzoxazolyl coumarin derivative, a dicyanomethylene pyran derivative, a dicyanomethylenethiopyran derivative, a polymethine derivative, a cyanine derivative, an oxobenz anthracene derivative, a xanthene derivative, a rhodamine derivative, a fluorescein derivative, a pyrylium derivative, a carbo styryl derivative, an acridine derivative, an oxazine derivative, a phenylene oxide derivative, a quinacridone derivative, quinazoline delivative, a pyrrolopyridine derivative, a furopyridine derivative, a 1,2,5-thiadiazolopyrene derivative, a pyrromethene derivative, a perinone derivative, a pyrrolo pyrrole derivative, a squarylium derivative, a violanthrone derivative, a phenazine derivative, an acridone derivative, a deazaflavin derivative, a fluorene derivative, and a benzofluorene derivative, are included.

When exemplified for each emission color, examples of the blue to bluish green dopant material include an aromatic hydrocarbon compound such as naphthalene, anthracene, phenanthrene, pyrene, triphenylene, perylene, fluorene, indene, and chrysene, and derivatives thereof, and an aromatic heterocyclic compound such as furan, pyrrol, thiophene, sillol, 9-silafluorene, 9,9'-spirobisilafluorene, benzothiophene, benzofuran, indole, dibenzothiophene, dibenzofuran, imidazopyridine, phenanthroline, pyrazine, naphtyridine, quinoxaline, pyrrolopyridine, and thioxanthene, and derivatives thereof, distyrylbenzene derivatives, tetraphenyl butadiene derivatives, stilbene derivatives, aldazine derivatives, coumarin derivatives, azole derivatives such as imidazole, thiazole, thiadiazole, carbazole, oxazole, oxadiazole, and triazole, and metal complexes thereof, and aromatic amine derivatives represented by N,N'-diphenyl-N, N'-di(3-methylphenyl)-4,4'-diphenyl-1,1'-diamine.

Further, examples of the green to yellow dopant materials include coumarin derivatives, phthalimide derivatives, naphthalimide derivatives, perinone derivatives, pyrrolopyrrol derivatives, cyclopentadiene derivatives, acridone derivatives, quinacridone derivatives, and naphthacene derivatives such as rubrene, and also preferred examples include the compounds exemplified above as the blue to bluish green dopant material that are introduced with a substituent enabling a shift to longer wavelength such as an aryl group, a heteroaryl group, an arylvinyl group, an amino group, and a cyano group.

Further, examples of the orange to red dopant materials include naphthalimide derivative such as bis(diisopropylphenyl)perylene tetracarboxylic imide, perinone derivatives, rare earth complex such as Eu complex having ligands such as acetyl acetone, benzoyl acetone, and phenanthroline, 4-(dicyanomethylene)-2-methyl-6-(p-dimethylaminostyryl)-4H-pyran and its analogs, metal phthalocyanine derivatives such as magnesium phthalocyanine and aluminum chlorophthalocyanine, rhodamin compounds, deazaflavin derivatives, coumarin derivatives, quinacridone derivatives, phenoxazine derivatives, oxazine derivatives, quinazoline derivatives, pyrrolopyridine derivatives, squarylium derivatives, violanthrone derivatives, phenazine derivatives, phenoxazone derivatives, and thiadiazolopyrene derivatives, and also preferred examples include the compounds exemplified above as the blue to bluish green dopant material and the green to yellow dopant material that are introduced with a substituent enabling a shift to longer wavelength such as an aryl group, a heteroaryl group, an arylvinyl group, an amino group, and a cyano group.

In addition to the above compounds, compounds suitably selected from compounds described in Chemical Industry Daily issued in June 2004, page 13, reference documents quoted therein and the like can be used as the dopant.

Among the dopant materials described above, amine having a stilbene structure, perylene derivatives, borane derivatives, aromatic amine derivatives, coumarin derivatives, pyran derivatives, and pyrene derivatives are preferred.

Amine with a stilbene structure is represented by the following formula, for example.

[Formula 39]

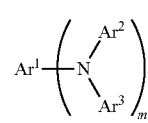

In the formula, $Ar^1$ is a group with valency m derived from aryl having 6 to 30 carbon atoms, $Ar^2$ and $Ar^3$ are each independently aryl having 6 to 30 carbon atoms, in which at least one of $Ar^1$ to $Ar^3$ has a stilbene structure, in which $Ar^1$ to $Ar^3$ may be substituted, and m is an integer of from 1 to 4.

The amine with a stilbene structure is preferably a diaminostilbene represented by the following formula.

[Formula 40]

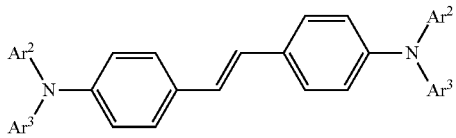

In the formula, $Ar^2$ and $Ar^3$ are each independently aryl having 6 to 30 carbon atoms and $Ar^2$ and $Ar^3$ may be substituted.

Specific examples of aryl having 6-30 carbon atoms include benzene, naphthalene, acenaphthylene, fluorene, phenalene, phenanthrene, anthracene, fluoranthene, triphenylene, pyrene, chrysene, naphthacene, perylene, stilbene, distyrylbenzen, distyrylbiphenyl, and distyryl fluorene.

Specific examples of amine which has a stilbene structure include: N,N,N',N'-tetra(4-biphenylyl)-4,4'-diaminostilbene, N,N,N',N'-tetra(1-naphthyl)-4,4'-diaminostilbene, N,N,N',N'-tetra(2-naphthyl)-4,4'-diaminostilbene, N,N'-di(2-naphthyl)-N,N'-diphenyl-4,4'-diaminostilbene, N,N'-di(9-phenanthryl)-N,N'-diphenyl-4,4'-diaminostilbene, 4,4'-bis [4"-bis(diphenylamino) styryl]-biphenyl, 1,4-bis[4'-bis (diphenylamino) styryl]-benzene, 2,7-bis[4'-bis (diphenylamino)styryl]-9,9-dimethylfluorene, 4,4'-bis(9-ethyl-3-carbazovinylene)-biphenyl, and 4,4'-bis(9-phenyl-3-carbazovinylene)-biphenyl.

Further, amine which has the stilbene structure indicated in JP-A Nos. 2003-347056 and 2001-307884 may also be used.

Examples of a perylene derivative include 3,10-bis(2,6-dimethylphenyl)perylene, 3,10-bis(2,4,6-trimethyl phenyl) perylene, 3,10-diphenyl perylene, 3,4-diphenyl perylene, 2,5,8,11-tetra-t-butyl perylene, 3,4,9,10-tetraphenyl perylene, 3-(1'-pyrenyl)-8,11-di(t-butyl)perylene, 3-(9'-anthryl)-8,11-di(t-butyl)perylene, and 3,3'-bis(8,11-di(t-butyl)perylenyl).

The peryline derivative indicated in JP-A Nos. 11-97178, 2000-133457, 2000-26324, 2001-267079, 2001-267078, 2001-267076, 2000-34234, 2001-267075, and 2001-217077 may also be used.

Examples of a borane derivative include 1,8-diphenyl-10-(dimesitylboryl)anthracene, 9-phenyl-10-(dimesitylboryl) anthracene, 4-(9'-anthryl)dimesitylboryl naphthalene, 4-(10'-phenyl-9'-anthryl)dimesitylboryl naphthalene, 9-(dimesitylboryl)anthracene, 9-(4'-biphenylyl)-10-(dimesitylboryl)anthracene, and 9-(4'-(N-carbazolyl)phenyl)-10-(dimesitylboryl)anthracene.

The borane derivative indicated in WO 2000/40586 A may also be used.

The aromatic amine derivatives are represented by the following formula, for example.

[Formula 41]

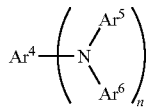

In the formula, $Ar^4$ is a group with valency n derived from aryl having 6 to 30 carbon atoms, $Ar^5$ and $Ar^6$ are each independently aryl having 6 to 30 carbon atoms, in which $Ar^4$ to $Ar^6$ may be substituted, and n is an integer of from 1 to 4.

In particular, an aromatic amine derivative in which $Ar^4$ is a divalent group derived from anthracene, chrysene, or pyrene, $Ar^5$ and $Ar^6$ are each independently aryl having 6 to 30 carbon atoms, in which $Ar^4$ to $Ar^6$ may be substituted, and n is 2 is more preferable.

Specific examples of aryl having 6-30 carbon atoms include benzene, naphthalene, acenaphthylene, fluorene phenalene, phenanthrene, anthracene, fluoranthene, triphenylene, pyrene, chrysene, naphthacene, perylene, and pentacene.

Examples of an aromatic amine derivative include, as chrysene, N,N,N',N'-tetraphenylchrysene-6,12-diamine, N,N,N',N'-tetra(p-tolyl)chrysene-6,12-diamine, N,N,N',N'-tetra(m-tolyl)chrysene-6,12-diamine,N,N,N',N'-tetrakis(4-isopropylphenyl)chrysene-6,12-diamine, N,N,N',N'-tetra (naphthalene-2-yl)chrysene-6,12-diamine, N,N'-diphenyl-N,N'-di(p-tolyl)chrysene-6,12-diamine, N,N'-diphenyl-N,N'-bis(4-ethylphenyl)chrysene-6,12-diamine, N,N'-diphenyl-N,N'-bis(4-ethylphenyl)chrysene-6,12-diamine, N,N'-diphenyl-N,N'-bis(4-isopropylphenyl)chrysene 6,12-diamine, N,N'-diphenyl-N,N'-bis(4-t-butylphenyl)chrysene-6,12-diamine, and N,N'-bis(4-isopropylphenyl)-N,N'-di(p-tolyl)chrysene-6,12-diamine.

Examples of pyrene include N,N,N',N'-tetraphenylpyrene-1,6-diamine, N,N,N',N'-tetra(p-tolyl)pyrene-1,6-diamine, N,N,N',N'-tetra(m-tolyl)pyrene-1,6-diamine, N,N,N',N'-tetrakis(4-isopropylphenyl)pyrene-1,6-diamine, N,N,N',N'-tetrakis(3,4-dimethylphenyl)pyrene-1,6-diamine, N,N'-diphenyl-N,N'-di(p-tolyl)pyrene-1,6-diamine, N,N'-diphenyl-N,N'-bis(4-ethylphenyl)pyrene-1,6-diamine, N,N'-diphenyl-N,N'-bis(4-ethylphenyl)pyrene-1,6-diamine, N,N'-diphenyl-N,N'-bis(4-isopropylphenyl)pyrene-1,6-diamine, N,N'-diphenyl-N,N'-bis(4-t-butylphenyl)pyrene 1,6-diamine, N,N'-bis(4-isopropylphenyl)-N,N'-di(p-tolyl)pyrene-1,6-diamine, and N,N,N',N'-tetrakis(3,4-dimethylphenyl)-3,8-diphenylpyrene-1,6-diamine.

Examples of anthracene include N,N,N,N-tetraphenylanthracen-9,10-diamine, N,N,N',N'-tetra(p-tolyl)anthracen-9,10-diamine, N,N,N',N'-tetra(m-tolyl)anthracen-9,10-diamine, N,N,N',N'-tetrakis(4-isopropylphenyl)anthracen-9,10-diamine, N,N'-diphenyl-N,N'-di(p-tolyl)anthracen-9,10-diamine, N,N'-diphenyl-N,N'-di(m-tolyl)anthracen-9,10-diamine, N,N'-diphenyl-N,N'-bis(4-ethylphenyl)anthracen-9,10-diamine, N,N'-diphenyl-N,N'-bis(4-ethylphenyl) anthracen-9,10-diamine, N,N'-diphenyl-N,N'-bis(4-isopropylphenyl) anthracen-9,10-diamine, N,N'-diphenyl-N,N'-bis (4-t-butylphenyl)anthracen-9,10-diamine, N,N'-bis(4-isopropylphenyl)-N,N'-di(p-tolyl) anthracen-9,10-diamine, 2,6-di-t-butyl-N,N,N',N'-tetra(p-tolyl)anthracen-9,10-diamine, 2,6-di-t-butyl-N,N'-diphenyl-N,N'-bis(4-isopropylphenyl) anthracen-9,10-diamine, 2,6-di-t-butyl-N,N'-bis(4-isopropylphenyl)-N,N'-di(p-tolyl)anthracen-9,10-diamine, 2,6-dicyclohexyl-N,N'-bis(4-isopropylphenyl)-N,N'-di(p-tolyl) anthracen-9,10-diamine, 2,6-dicyclohexyl-N,N'-bis(4-isopropylphenyl)-N,N'-bis(4-t-butylphenyl)anthracen-9,10-diamine, 9,10-bis(4-diphenylamino-phenyl)anthracene, 9,10-bis(4-di(1-naphthylamino)phenyl)anthracene, 9,10-bis (4-di(2-naphthylamino)phenyl) anthracene, 10-di-p-tolylamino-9-(4-di-p-tolylamino-1-naphthyl)anthracene, 10-diphenylamino-9-(4-diphenylamino-1-naphthyl)anthracene, and 10-diphenylamino-9-(6-diphenylamino-2-naphthyl)anthracene.

Examples of pyrene include N,N,N,N-tetraphenyl-1,8-pyrene-1,6-diamine, N-biphenyl-4-yl-N-biphenyl-1,8- pyrene-1,6-diamine, and $N^1,N^6$-diphenyl-$N^1,N^6$-bis-(4-trimethylsilanyl-phenyl)-1H,8H-pyrene-1,6-diamine.

Other examples include [4-(4-diphenylamino-phenyl) naphthalene-1-yl]-diphenylamine, [6-(4-diphenylaminophenyl)naphthalene-2-yl]-diphenylamine, 4,4'-bis[(4-diphenylaminonaphthalene-1-yl)]biphenyl, 4,4'-bis[(6-diphenylaminonaphthalene-2-yl)]biphenyl, 4,4''-bis[4-diphenylaminonaphthalene-1-yl]-p-terphenyl, and 4,4''-bis [6-diphenylaminonaphthalene 2-yl]-p-terphenyl.

The aromatic amine derivative indicated in JP-A No. 2006-156888 may also be used.

Examples of a coumarin derivative include Coumarin 6 and Coumarin 334.

The coumarin derivative indicated in JP-A Nos. 2004-43646, 2001-76876, and 6-298758 may also be used.

Examples of a pyran derivative include DCM and DCJTB.

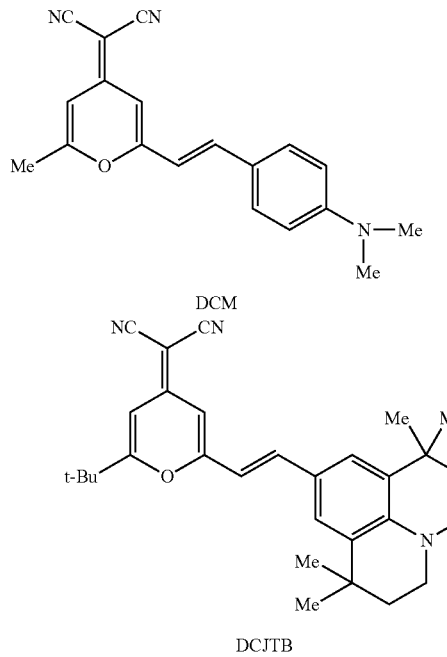

[Formula 42]

DCM

DCJTB

The pyran derivative indicated in JP-A Nos. 2005-126399, 2005-097283, 2002-234892, 2001-220577, 2001-081090, and 2001-052869 may also be used.

<Electron Injection Layer and Electron Transport Layer of Organic Electroluminescence Element>

The electron injection layer 107 plays a role of efficiently injecting electrons moving from the negative electrode 108 into the light emitting layer 105 or the electron transport layer 106. The electron transport layer 106 plays a role of efficiently transporting electrons injected from the negative electrode 108 or electrons injected from the negative electrode 108 via the electron injection layer 107 into the light emitting layer 105. The electron transport layer 106 and the electron injection layer 107 are formed respectively by laminating or mixing at least one of electron transporting and injecting materials or from a mixture of the electron transporting and injecting material with a high molecular binder.

An electron injection and transport layer is a layer for controlling injection of electrons from the negative electrode and transportation of the electrons, and it is desirable that the electron injection efficiency be high and that the electrons injected be efficiently transported. Accordingly, preferred is the material which has large electron affinity and large electron mobility and is excellent in stability and in which impurities trapped are less liable to be generated during production and use. However, when considering a transport balance between a hole and an electron, the material is provided, even if electron transport ability is not so high, with an effect of enhancing light emission efficiency to the same extent as that of a material having high electron transport ability in the case of playing principally a role of efficiently inhibiting holes coming from the positive electrode from moving to a negative electrode side without recombination. Accordingly, a function of a layer which can efficiently inhibit holes from moving may be included as well in the electron injection and transport layer in the present embodiment.

Compounds optionally selected from compounds which have so far conventionally been used as an electron transport compound in a photoconductive material and known compounds used for an electron injection layer and an electron transport layer in an organic electroluminescence element can be used as materials for forming the electron transport layer 106 or the electron injection layer 107 (i.e., electron transport material).

A material used for the electron transport layer or electron injection layer preferably contains at least one selected from a compound consisting of aromatic ring or heteroaromatic ring which consists of one or more atoms selected from carbon, hydrogen, oxygen, sulfur, silicon, and phosphorus, pyrrole derivatives, condensed ring derivatives thereof, and a metal complex having electron-accepting nitrogen. Specific examples thereof include condensed ring-based aromatic ring derivatives such as naphthalene and anthracene, styryl-based aromatic ring derivatives represented by 4,4'-bis(diphenylethenyl)biphenyl, perinone derivatives, coumarin derivatives, naphthalimide derivatives, quinone derivatives such as anthraquinone and diphenoquinone, phosphorus oxide derivatives, carbazole derivatives, and indol derivatives. Examples of the metal complex having electron-accepting nitrogen include a hydroxyazole complex such as hydroxyphenyl oxazole complex, an azomethine complex, a tropolone metal complex, a flavonol metal complex, and a benzoquinoline metal complex. Those materials may be used either singly or as a mixture with different materials.

Specific examples of other electron transport compound include pyridine derivatives, naphthalene derivatives, anthracene derivatives, phenanthroline derivatives, perinone derivatives, coumarin derivatives, naphthalimide derivatives, anthraquinone derivatives, diphenoquinone derivatives, diphenylquinone derivatives, perylene derivatives, oxadiazole derivatives (1,3-bis[(4-t-butylphenyl)1,3,4-oxadiazolyl] phenylene or the like), thiophene derivatives, triazole derivatives (N-naphthyl-2,5-diphenyl-1,3,4-triazole or the like), thiadiazole derivatives, a metal complex of oxine derivatives, a quinolino-based metal complex, quinoxaline derivatives, a polymer of quinoxaline derivatives, a benzazole compound, a gallium complex, pyrazole derivatives, perfluorophenylene derivatives, triazine derivatives, pyrazine derivatives, benzoquinoline derivatives (2,2'-bis(benzo[h]quinolin-2-yl)-9,9'-spirobifluorene or the like), imidazopyrine derivatives, borane derivatives, benzimidazole derivatives (tris(N-phenylbenzimidazol-2-yl)benzene or the like), benzoxazole derivatives, benzthiazole derivatives, quinoline derivatives, oligopyridine derivatives such as terpyridine, bipyridine derivatives, terpyridine derivatives (1,3-bis(4'-(2,2':6'2''-terpyridinyl))benzene or the like), naphthylidine derivatives (bis(1-naphthyl)-4-(1,8-naphthylidin-2-yl)phenylphosphine oxide or the like), aldazine derivatives, carbazole derivatives, indole derivatives, phosphorus oxide derivatives, and bisstyryl derivatives.

Further, a metal complex having electron-accepting nitrogen can be also used, and examples thereof include a quinolinol-based metal complex, a hydroxyazole complex such as hydroxyphenyl oxazole complex, an azomethine complex, a tropolone metal complex, a flavonol metal complex, and a benzoquinoline metal complex.

Those materials may be used either singly or as a mixture with different materials.

Among the materials described above, a quinolinol-based metal complex, bipyridine derivatives, phenanthroline derivatives, and borane derivatives are preferable.

The quinolinol-based metal complex is a compound represented by the following formula (E-1).

[Formula 43]

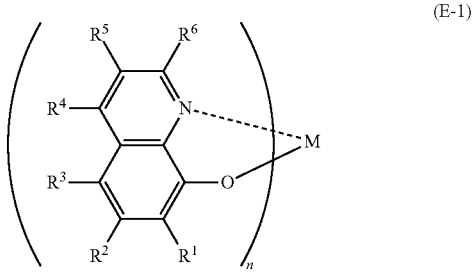

(E-1)

In the formula, $R^1$ to $R^6$ are a hydrogen or a substituent, M is Li, Al, Ga, Be, or Zn, and n is an integer of from 1 to 3.

Example of a quinolinol metal complex include 8-quinolinol lithium, tris(8-quinolate)aluminium, tris(4-methyl-8-quinolate)aluminium, tris(5-methyl-8-quinolate)aluminium, tris(3,4-dimethyl-8-quinolate)aluminium, tris(4,5-dimethyl-8-quinolate)aluminium, tris(4,6-dimethyl-8-quinolate)aluminium, bis(2-methyl-8-quinolate)(phenolate)aluminium, bis(2-methyl-8-quinolate)(2-methylphenolate)aluminium, bis(2-methyl-8-quinolate)(3-methylphenolate)aluminium, bis(2-methyl-8-quinolate)(4-methylphenolate)aluminium, bis(2-methyl-8-quinolate)(2-phenylphenolate)aluminium, bis(2-methyl-8-quinolate)(3-phenylphenolate)aluminium, bis(2-methyl-8-quinolate)(4-phenylphenolate)aluminium, bis(2-methyl-8-quinolate)(2,3-dimethylphenolate)aluminium, bis(2-methyl-8-quinolate)(2,6-dimethylphenolate)aluminium, bis(2-methyl-8-quinolate)(3,4-dimethylphenolate)aluminium, bis(2-methyl-8-quinolate)(3,5-dimethylphenolate)aluminium, bis(2-methyl-8-quinolate)(3,5-di-t-butylphenolate)aluminium, bis(2-methyl-8-quinolate)(2,6-diphenylphenolate)aluminium, bis(2-methyl-8-quinolate)(2,4,6-triphenylphenolate)aluminium, bis(2-methyl-8-quinolate)(2,4,6-trimethyl phenolate)aluminium, bis(2-methyl-8-quinolate)(2,4,5,6-tetramethylphenolate)aluminium, bis(2-methyl-8-quinolate)(1-naphtholate)aluminium, bis(2-methyl-8-quinolate)(2-naphtholate)aluminium, bis(2,4-dimethyl-8-quinolate)(2-phenylphenolate)aluminium, bis(2,4-dimethyl-8-quinolate)(3-phenylphenolate)aluminium, bis(2,4-dimethyl-8-quinolate)(4-phenylphenolate)aluminium, bis(2,4-dimethyl-8-quinolate)(3,5-dimethylphenolate)aluminium, bis(2,4-dimethyl-8-quinolate)(3,5-di-t-butylphenolate)aluminium, bis(2-methyl-8-quinolate)aluminium-μ-oxobis(2-methyl-8-quinolate)aluminium, bis(2,4-dimethyl-8-quinolate)aluminium-μ-oxobis(2,4-dimethyl-8-quinolate)aluminium, bis(2-methyl-4-ethyl-8-quinolate)aluminium-μ-oxobis(2-methyl-4-ethyl-8-quinolate)aluminium, bis(2-methyl-4-methoxy-8-quinolate)aluminium-μ-oxobis(2-methyl-4-methoxy-8-quinolate)aluminium, bis(2-methyl-5-cyano-8-quinolate)aluminium-μ-oxobis(2-methyl-5-cyano-8-quinolate)aluminium, bis(2-methyl-5-trifluoromethyl-8-quinolate)aluminium-μ-oxobis(2-methyl-5-trifluoromethyl-8-quinolate)aluminium, and bis(10-hydroxybenzo[h]quinoline)beryllium.

The bipyridine derivatives are a compound represented by the following formula (E-2).

[Formula 44]

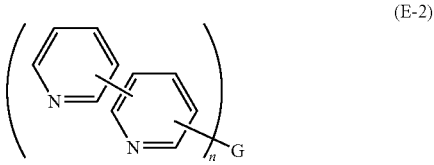

(E-2)

In the formula, G represents a simple bonding arm or a linker group having valency n, and n is an integer of from 2 to 8. Further, the carbon atoms not utilized for bonding between pyridine and pyridine or pyridine and G may be substituted.

Examples of the G in Formula (E-2) include those having following structural formula. Further, R in the following structural formula is each independently hydrogen, methyl, ethyl, isopropyl, cyclohexyl, phenyl, 1-naphthyl, 2-naphthyl, biphenylyl, or terphenylyl.

[Formula 45]

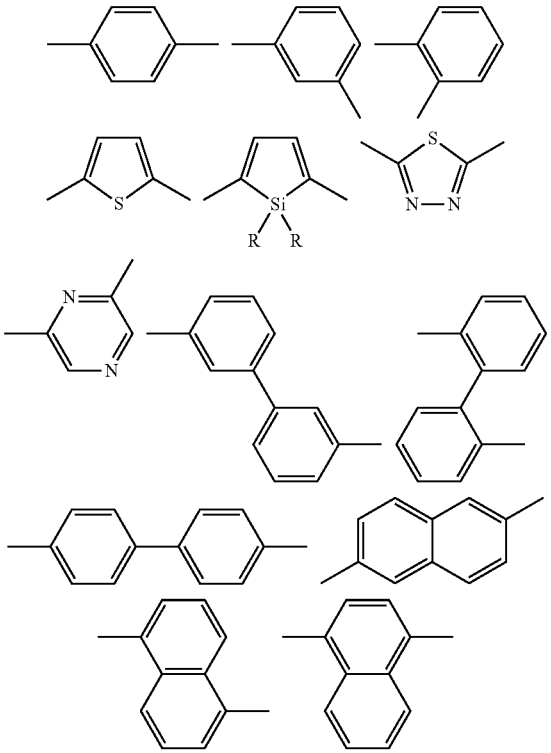

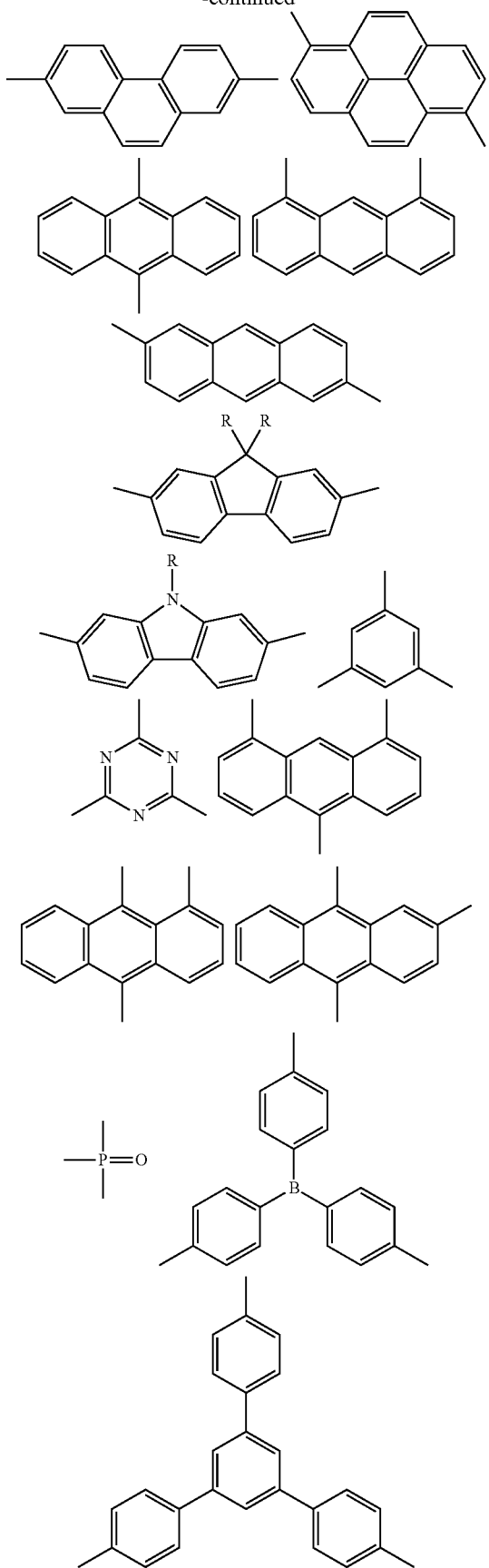

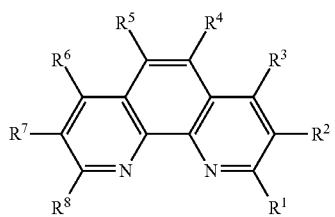

Specific examples of a pyridin derivative include 2,5-bis(2,2'-bipyridine-6-yl)-1,1-dimethyl-3,4-diphenylsilole, 2,5-bis(2,2'-bipyridine-6-yl)-1,1-dimethyl-3,4-dimesitile silole, 2,5-bis(2,2'-bipyridine 5-yl)-1,1-dimethyl-3,4-diphenyl-silole, 2,5-bis(2,2'-bipyridine-5-yl)-1,1-dimethyl-3,4-dimesitile silole, 9,10-di(2,2'-bipyridine-6-yl)anthracene, 9,10-di(2,2'-bipyridine-5-yl)anthracene, 9,10-di(2,3'-bipyridine-6-yl)anthracene, 9,10-di(2,3'-bipyridine-5-yl)anthracene, 9,10-di(2,3'-bipyridine-6-yl)-2-phenylanthracene, 9,10-di(2,3'-bipyridine-5-yl)-2-phenylanthracene, 9,10-di(2,2'-bipyridine-6-yl)-2-phenylanthracene, 9,10-di(2,2'-bipyridine-5-yl)-2-phenylanthracene, 9,10-di(2,4'-bipyridine-6-yl)-2-phenylanthracene, 9,10-di(2,4'-bipyridine-5-yl)-2-phenylanthracene, 9,10-di(3,4'-bipyridine-6-yl)-2-phenylanthracene, 9,10-di(3,4'-bipyridine-5-yl)-2-phenylanthracene, 3,4-diphenyl-2,5-di(2,2'-bipyridine-6-yl)thiophene, 3,4-diphenyl-2,5-di(2,3'-bipyridine-5-yl)thiophene, and 6'6"-di(2-pyridyl) 2,2':4',4": 2"2"'-quaterpyridin.

The phenanthroline derivatives are a compound represented by the following formula (E-3-1) or (E-3-2).

[Formula 46]

(E-3-1)

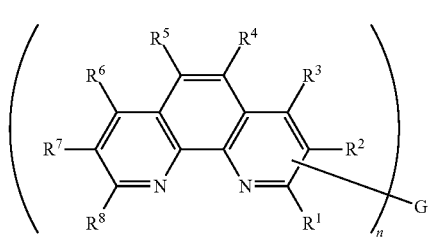

(E-3-2)

In the formula, $R^1$ to $R^8$ are a hydrogen or a substituent, neighboring groups may bind to each other to form a condensed ring, G represents a simple bonding arm or a linker group having valency n, and n is an integer of from 2 to 8. Further, the examples of G in Formula (E-3-2) include the same ones as those in the description of the bipyridine derivatives section.

Examples of a phenanthroline derivative include 4,7-diphenyl-1,10-phenanthroline, 2,9-dimethyl-4,7-diphenyl-1,10-phenanthroline, 9,10-di(1,10-phenanthroline-2-yl)anthracene, 2,6-di(1,10-phenanthroline-5-yl)pyridin, 1,3,5-tri(1,10-phenanthroline-5-yl)benzene, 9,9'-difluor-bis(1,10-phenanthroline-5-yl), bathocuproine, and 1,3-bis(2-phenyl-1,10-phenanthroline-9-yl)benzene.

A case in which a phenanthroline derivative is used for the electron transport layer and electron injection layer will be described. A material which is excellent in thermal stability and ability to form a thin film is desired for obtaining stable light emission over a long period of time. Among the phenanthroline derivatives, preferred are compounds in which a substituent itself has a three-dimensional steric structure or which are provided with a three-dimensional steric structure by steric repulsion against the phenanthroline skeleton or an adjacent substituent and compounds in which plural phenanthroline skeletons are combined. Further, when combining plural phenanthroline skeletons, more preferred are compounds containing a conjugated bond, a substituted or non-substituted aromatic hydrocarbon and a substituted or non-substituted aromatic heterocycle in a combined unit.

The borane derivatives are a compound represented by the following formula (E-4), and they are disclosed in detail in JP-A No. 2007-27587.

[Formula 47]

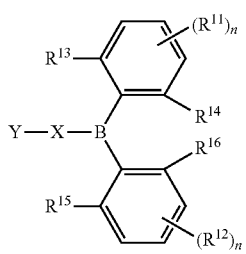

(E-4)

In the formula, $R^{11}$ and $R^{12}$ are each independently at least one of a hydrogen atom, an alkyl group, an aryl group which may be substituted, a substituted silyl group, a nitrogen-containing heterocyclic group which may be substituted, and a cyano group, $R^{13}$ to $R^{16}$ are each independently an alkyl group which may be substituted or an aryl group which may be substituted, X is an arylene group which may be substituted, Y is an aryl group having 16 carbon atoms or less which may be substituted, a substituted boryl group, or a carbazole group which may be substituted, and n is each independently an integer of from 0 to 3.

Among the compounds represented by the above-mentioned formula (E-4), compounds represented by the following formula (E-4-1) and further compounds represented by following the formulae (E-4-1-1) to (E-4-1-4) are preferable. Specific examples of such compounds include 9-[4-(4-dimesitylboryl naphthalene-1-yl)phenyl]carbazole, and 9-[4-(4-dimesitylboryl naphthalene-1-yl)naphthalene-1-yl]carbazole.

[Formula 48]

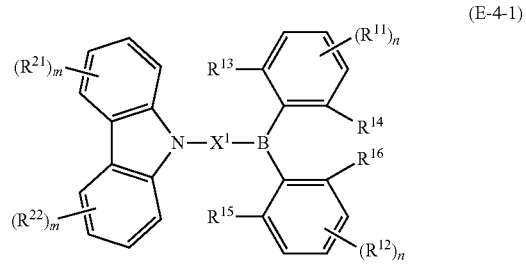

(E-4-1)

In the formula, $R^{11}$ and $R^{12}$ are each independently at least one of a hydrogen atom, an alkyl group, an aryl group which may be substituted, a substituted silyl group, a nitrogen-containing heterocyclic group which may be substituted, and a cyano group, $R^{13}$ to $R^{16}$ are each independently an alkyl group which may be substituted or an aryl group which may be substituted, $R^{21}$ and $R^{22}$ are each independently at least one of a hydrogen atom, an alkyl group, an aryl group which may be substituted, a substituted silyl group, a nitrogen-containing heterocyclic group which may be substituted, and a cyano group, $X^1$ is an arylene group having 20 carbon atoms or less which may be substituted, n is each independently an integer of from 0 to 3, and m is each independently an integer of from 0 to 4.

[Formula 49]

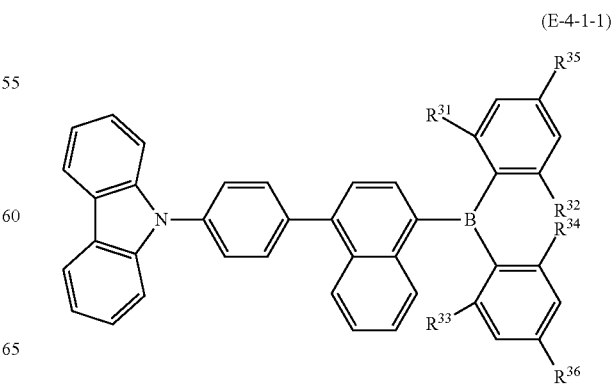

(E-4-1-1)

-continued

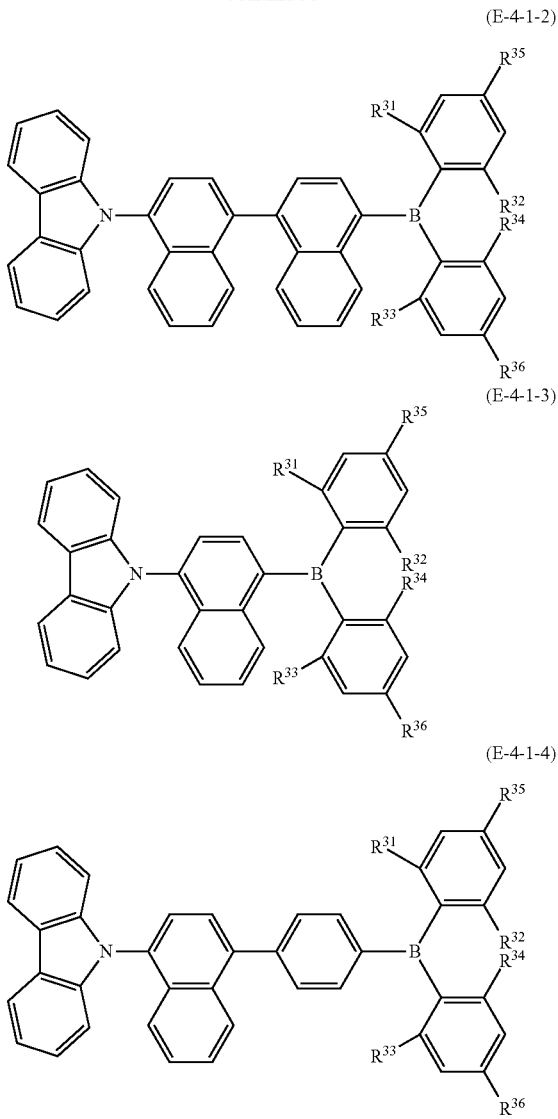

(E-4-1-2)

(E-4-1-3)

(E-4-1-4)

In each formula, $R^{31}$ to $R^{34}$ each independently are any one of methyl, isopropyl, and phenyl, and $R^{35}$ and $R^{36}$ each independently are any one of hydrogen, methyl, isopropyl, and phenyl.

Also in compounds represented by the above-mentioned formula (E-4), compounds represented by the following formula (E-4-2) and further compounds represented by the following formula (E-4-2-1) are preferable.

[Formula 50]

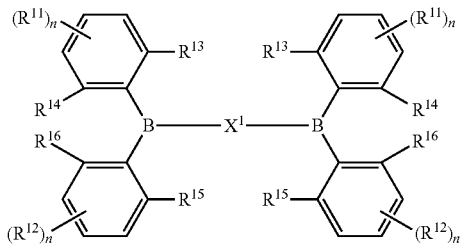

(E-4-2)

In the formula, $R^{11}$ and $R^{12}$ are each independently at least one of a hydrogen atom, an alkyl group, an aryl group which may be substituted, a substituted silyl group, a nitrogen-containing heterocyclic group which may be substituted, and a cyano group, $R^{13}$ to $R^{16}$ are each independently an alkyl group which may be substituted or an aryl group which may be substituted, $X^1$ is an arylene group having 20 carbon atoms or less which may be substituted, n is each independently an integer of from 0 to 3.

[Formula 51]

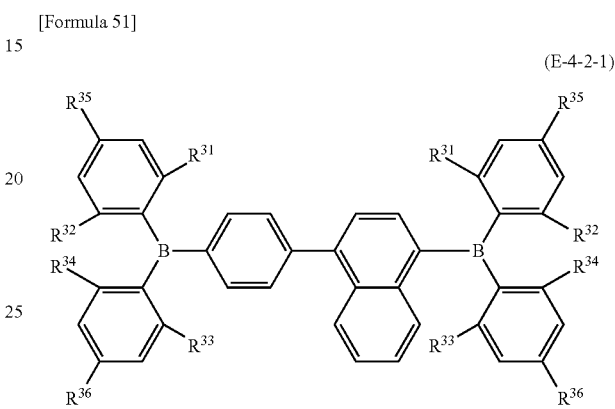

(E-4-2-1)

In the formula, $R^{31}$ to $R^{34}$ each independently are any one of methyl, isopropyl, and phenyl, and $R^{35}$ and $R^{36}$ each independently are any one of hydrogen, methyl, isopropyl, and phenyl.

Among the compounds represented by the above-mentioned formula (E-4), compounds represented by the following formula (E-4-3) is preferable, and the compound represented by the following formula (E-4-3-1) or (E-4-3-2) is further preferable.

[Formula 52]

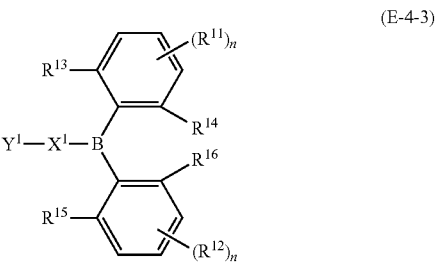

(E-4-3)

In the formula, $R^{11}$ and $R^{12}$ are each independently at least one of a hydrogen atom, an alkyl group, an aryl group which may be substituted, a substituted silyl group, a nitrogen-containing heterocyclic group which may be substituted, and a cyano group, $R^{13}$ to $R^{16}$ are each independently an alkyl group which may be substituted or an aryl group which may be substituted, $X^1$ is an arylene group having 10 carbon atoms or less which may be substituted, $Y^1$ is an arylene group having 14 carbon atoms or less which may be substituted, and n is each independently an integer of from 0 to 3.

[Formula 53]

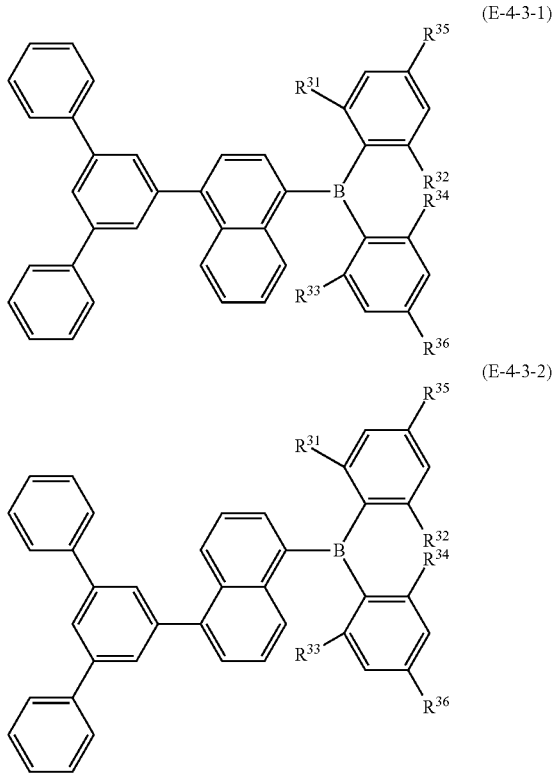

In each formula, $R^{31}$ to $R^{34}$ each independently are any one of methyl, isopropyl, and phenyl, and $R^{35}$ and $R^{36}$ each independently are any one of hydrogen, methyl, isopropyl, and phenyl.

The benzimidazole derivatives are a compound represented by the following formula (E-5).

[Formula 54]

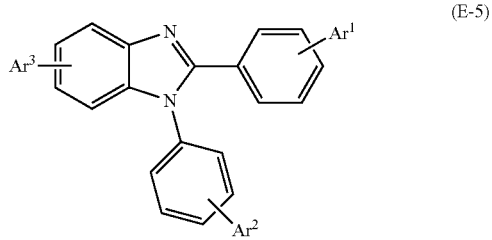

In the formula, $Ar^1$ to $Ar^3$ each independently are a hydrogen or an aryl having 6 to 30 carbon atoms which may be substituted. In particular, benzimidazole derivatives in which $Ar^1$ is substitutable anthryl are preferable.

Specific examples of aryl having 6-30 carbon atoms include phenyl, 1-naphthyl, 2-naphthyl, Acenaphthylene-1-yl, acenaphthylene-3-yl, acenaphthylene 4-yl, Acenaphthylene 5-yl, fluorene-1-yl, fluorene-2-yl, fluorene-3-yl, fluorene-4-yl, fluorene-9-yl, phenalene-1-yl, phenalene-2-yl, 1-phenanthryl, 2-phenanthryl, 3-phenanthryl, 4-phenanthryl, 9-phenanthryl, 1-anthryl, 2-anthryl, 9-anthryl, fluoranthene-1-yl, fluoranthene-2-yl, fluoranthene-3-yl, fluoranthene-7-yl, fluoranthene-8-yl, triphenylene-1-yl, triphenylene-2-yl, pyrene-1-yl, pyrene-2-yl, pyrene-4-yl, chrysene-1-yl, chrysene-2-yl, chrysene-3-yl, chrysene-4-yl, chrysene-5-yl, Chrysene-6-yl, naphthacene-1-yl, naphthacene-2-yl, naphthacene-5-yl, perylene-1-yl, perylene-2-yl, perylene-3-yl, pentacene-1-yl, pentacene-2-yl, pentacene-5-yl, and pentacene-6-yl.

Specific examples of a benzimidazole derivative include 1-phenyl-2-(4-(10-phenylanthracen-9-yl)phenyl)-1H-benzo[d]imidazole, 2-(4-(10-(naphthalene-2-yl)anthracen-9-yl)phenyl)-1-phenyl-1H-benzo[d]imidazole, 2-(3-(10-(naphthalene-2-yl)anthracen-9-yl)phenyl)-1-phenyl-1H-benzo[d]imidazole, 5-(10-(naphthalene-2-yl)anthracen-9-yl)-1,2-diphenyl-1H-benzo[d]imidazole, 1-(4-(10-(naphthalene-2-yl)anthracen-9-yl)phenyl)-2-phenyl-1H-benzo[d]imidazole, 2-(4-(9,10-di(naphthalene-2-yl)anthracen-2-yl)phenyl)-1-phenyl-H-benzo[d]imidazole, 1-(4-(9,10-di(naphthalene-2-yl)anthracen-2-yl)phenyl)-2-phenyl-1H-benzo[d]imidazole, and 5-(9,10-di(naphthalene-2-yl)anthracen-2-yl)-1,2-diphenyl-1H-benzo[d]imidazole.

The electron transport layer or electron injection layer may contain a material capable of reducing a material for forming the electron transport layer or electron injection layer. Various materials can be used as a reducing material as long as it has a certain reducing ability. Preferred examples thereof which may be used include at least one selected from a group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal.

Preferred examples of the reducing material include an alkali metal such as Na (work function; 2.36 eV), K (ditto; 2.28 eV), Rb (ditto; 2.16 eV), and Cs (ditto; 1.95 eV), and an alkali earth metal such as Ca (ditto; 2.9 eV), Sr (ditto; 2.0 to 2.5 eV), and Ba (ditto; 2.52 eV). Those with work function of 2.9 eV or less are particularly preferable. Of them, examples of the more preferred reducing material include an alkali metal such as K, Rb, and Cs. Examples of the still more preferred reducing material include Rb and Cs. Most preferably, it is Cs. The alkali metals have high reducing ability, in particular, and according to addition of a relatively small amount to a material for forming the electron transport layer or electron injection layer, improved emission luminance or long service life of the organic EL element can be achieved. In addition, as a reducing material having work function of 2.9 eV or less, a combination with two or more types of the above alkali metal is also preferable. In particular, a combination including Cs, for example a combination of Cs and Na, Cs and K, Cs and Rb, or Cs, Na, and K is preferable. By including Cs, the reducing ability is efficiently exhibited, and according to addition to a material for forming an electron transport layer or an electron injection layer, improved emission luminance or long service life of the organic EL element can be achieved.

<Negative Electrode of Organic Electroluminescence Element>

The negative electrode 108 plays a role of injecting electrons into the light emitting layer 105 via the electron injection layer 107 and the electron transport layer 106.

A material for forming the negative electrode 108 is not specifically limited as long as it is a material which can efficiently inject electrons into the organic layers, and the same materials as the materials for forming the positive electrode 102 can be used. Among them, preferred are metals such as tin, indium, calcium, aluminum, silver, copper, nickel, chromium, gold, platinum, iron, zinc, lithium, sodium, potassium, cesium, and magnesium and alloys thereof (magnesium-silver alloys, magnesium-indium alloys, and aluminum-lithium alloys such as lithium fluoride/aluminum alloys). Lithium, sodium, potassium, cesium, calcium, magnesium and alloys containing the above metals having a low work function are effective for elevating the electron injection efficiency to enhance the device characteristics. However, the above metals having a low work function are usually unstable in the air in many cases. Thus, to solve such problems, a method in which a small amount of lithium, cesium, and magnesium is doped onto an organic layer and using it as an electrode having high stability can be given as the preferred method. As other dopants, inorganic salts such as lithium fluoride, cesium fluoride, lithium oxide, and cesium oxide can be used as well, and therefore it is not specifically limited to the above materials.

Further, a preferred example for protecting the electrodes includes lamination of metals such as platinum, gold, silver, copper, iron, tin, aluminum, and indium, alloys using these metals, inorganic substances such as silica, titania, and silicon nitride, polyvinyl alcohol, polyvinyl chloride, and hydrocarbon high molecular compounds. A method for preparing the above electrodes is not specifically limited as long as the electrodes can conduct electricity. Examples include resistance heating, electron beam, sputtering, ion plating, coating and the like.

<Binder Usable for Each Layer>

The materials used for the hole injection layer, the hole transport layer, the light emitting layer, the electron transport layer, and the electron injection layer each described above can form alone the respective layers, and the materials which are dispersed in solvent-soluble resins such as polyvinyl chloride, polycarbonate, polystyrene, poly(N-vinylcarbazole), polymethyl methacrylate, polybutyl methacrylate, polyester, polysulfone, polyphenylene oxide, polybutadiene, hydrocarbon resins, ketone resins, phenoxy resins, polyamide, ethyl cellulose, vinyl acetate, ABS resins, and polyurethane resins; curing resins such as phenol resins, xylene resins, petroleum resins, urea resins, melamine resins, unsaturated polyester resins, alkyd resins, epoxy resins, and silicon resins; and the like as high molecular binders can be used as well.

<Method for Manufacturing Organic Electroluminescence Element>

The respective layers constituting the organic electroluminescence element can be formed by forming thin films from the materials for constituting the respective layers by methods such as a vapor deposition method, resistance heating deposition, electron beam deposition, sputtering, a molecular lamination method, a printing method, a spin coat method, a cast method, and a coating method. The film thicknesses of the respective layers thus formed is not specifically limited and can suitably be set according to the properties of the materials, and they fall usually in a range of 2 nm to 5000 nm. The film thickness can usually be measured by a quartz oscillation type film thickness measuring apparatus and the like. When a thin film is formed by a vapor deposition method, vapor deposition conditions thereof vary depending on the kind of the materials, the crystal structure and the aggregate structure which are aimed by the film. In general, the vapor deposition conditions can suitably be set preferably in the ranges of a boat heating temperature of 50 to 400° C., a vacuum degree of $10^{-6}$ to $10^{-3}$ Pa, a vapor deposition rate of 0.01 to 50 nm/second, a substrate temperature of $-150$ to $+300°$ C., and a film thickness of 2 nm to 5 μm.

Next, a preparing method for an organic electroluminescence element including a positive electrode/a hole injection layer/a hole transport layer/an light emitting layer including a host material and a dopant material/an electron transport layer/an electron injection layer/a negative electrode will be described as one example of a preparing method for the organic electroluminescence element. A thin film of a positive electrode material is formed on a suitable substrate by a deposition method and the like to prepare a positive electrode, and then the thin films of a hole injection layer and a hole transport layer are formed on the positive electrode. A host material and a dopant material are co-deposited thereon to form a thin film, whereby an light emitting layer is prepared, and an electron transport layer and an electron injection layer are formed on the light emitting layer. Further, a thin film including a substance for a negative electrode is formed thereon by a deposition method and the like to prepare a negative electrode, whereby the targeted organic electroluminescence element is obtained. In preparing the organic electroluminescence element described above, the preparing order may be in the other way around to prepare it as well in the order of the negative electrode, the electron injection layer, the electron transport layer, the light emitting layer, the hole transport layer, the hole injection layer and the positive electrode.

When direct voltage is applied to the organic electroluminescence element thus obtained, it may be applied with the positive electrode being set to a polarity of + and the negative electrode being set to a polarity of −, and when a voltage of approximately 2 to 40 V is applied, emission can be observed from a transparent or semi-transparent electrode side (the positive electrode or the negative electrode and both). This organic electroluminescence element emits light as well when applied with a pulse current and an alternating current. A waveform of the alternating current applied may have any form.

<Application Examples of Organic Electroluminescence Element>

The present invention can be applied as well to display units equipped with an organic electroluminescence element, lighting devices equipped with an organic electroluminescence element and the like.

The display units or lighting devices equipped with an organic electroluminescence element can be produced by such known methods that the organic electroluminescence element according to the present embodiment is connected with known drive apparatuses, and they can be driven by suitably using known drive methods such as direct current drive, pulse drive, and alternating current drive.

The display unit includes, for example, panel displays such as color flat panel displays and flexible displays such as flexible color electroluminescent (EL) displays (see, for example, JP-A Nos. 10-335066, 2003-321546, and 2004-281086). A display system of the displays includes, for example, a matrix display system and/or a segment display system. A matrix display system and a segment display system may be coexistent in the same panel.

A matrix means a state in which pixels for display are two-dimensionally arranged in a lattice form, a mosaic form and the like, and characters and images are displayed by aggregate of the pixels. The form and the size of the pixels are determined by applications. For example, square pixels having a side of 300 μm or less are usually used for display of images and characters in personal computers, monitors and TV. In the case of a large-sized display such as display panels, pixels having a side of mm order are used. In the case of monochrome display, pixels having the same color are arranged, and in the case of color display, red, green, and blue pixels are arranged for display. In this case, to be typical, a delta type and a stripe type are available. A drive method of this matrix may be either a linear sequential drive method and an active matrix. The linear sequential drive method has an advantage that it has a simpler structure. However, considering the operation characteristics, the active matrix is more excellent in a certain case, and therefore this has to be used separately depending on the applications.

In the segment system (type), patterns are formed so that information determined in advance is displayed, and light is emitted in a determined area. It includes, for example, display of time and temperature in digital watches and thermometers, display of operation states in audio devices and electromagnetic cookers and display of panels in automobiles.

A lighting device includes, for example, lighting devices such as indoor lighting devices and backlights for liquid crystal displays (see, for example, JP-A Nos. 2003-257621, 2003-277741, and 2004-119211). The backlights are used principally for a purpose of enhancing a visibility of display equipments which do not spontaneously emit light, and they are used for liquid crystal displays, watches, audio devices, car panels, display boards, indicators and the like. In particular, considering that backlights of a conventional system for uses in liquid crystal displays, especially, personal computers in which a reduction in a size is a problem include fluorescent lamps and light guide plates, so that it is difficult to make them thin-shaped, a backlight using the light emitting element according to the present embodiment is characterized by that it is thin-shaped and lightweight.

EXAMPLES

First, synthetic examples of the anthracene compounds used in the examples are described herein after.

Synthesis Example of Compound Represented by Formula (1-2)

[Formula 55]

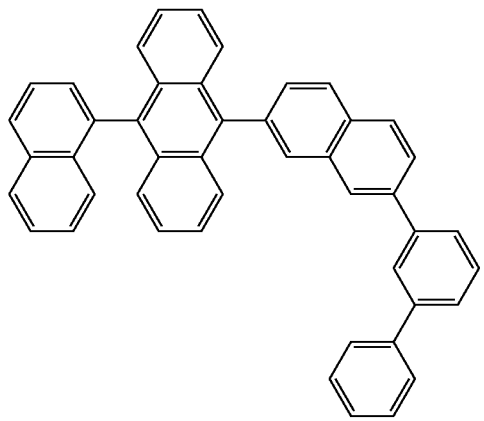

(1-2)

Synthesis of naphthalene-2,7-diyl bis(trifluoromethanesulfonate)

First, under the nitrogen atmosphere, 2,7-naphthalene diol (48.1 g) and pyridine (380 ml) were added to a flask, cooled to 0° C., and then slowly added dropwise with trifluoromethane sulfonic acid anhydride (203.1 g). After that, the reaction solution was stirred at 0° C. for 1 hour and at room temperature for 2 hours. Then, the reaction solution was added with water and the target component was extracted with toluene. The crude product obtained by concentrating the organic layer under reduced pressure was purified by silica gel column chromatography (solvent: heptane/toluene=6/1 (volume ratio)) to give naphthalene-2,7-diyl bis(trifluoromethane sulfonate) (112.4 g) as a first intermediate compound. The scheme is shown in the following "Reaction 1".

Reaction 1

[Formula 56]

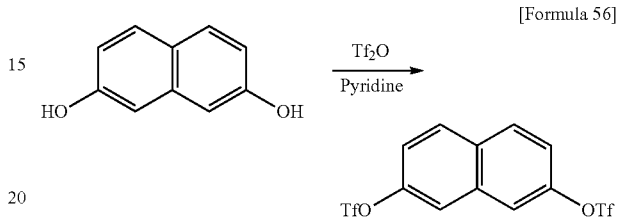

Synthesis of 7-([1,1'-biphenyl]-3-yl)naphthalene-2-yl trifluoromethanesulfonate

Under the nitrogen atmosphere, naphthalene-2,7-diyl-bis (trifluoromethane sulfonate) (25.5 g), which is the first intermediate compound obtained from the Reaction 1 above, m-biphenylboronic acid (11.9 g), tetrakis(triphenylphosphine)palladium (0) (Pd(PPh$_3$)$_4$) (1.39 g), potassium phosphate (25.5 g), and a mixture solvent (100 ml) of tetrahydrofuran (THF) and isopropyl alcohol (IPA) (THF/IPA=4/1 (volume ratio)) were added to a flask and refluxed for 4 hours. Once the heating is completed, the reaction solution was cooled, added with water, and the target component was extracted with toluene. The crude product obtained by concentrating the organic layer under reduced pressure was purified by silica gel column chromatography (solvent: heptane) to give 7-([1,1'-biphenyl]-3-yl)naphthalen-2-yl trifluoromethane sulfonate (14.8 g) as a second intermediate compound. The scheme is shown in the following "Reaction 2".

Reaction 2

[Formula 57]

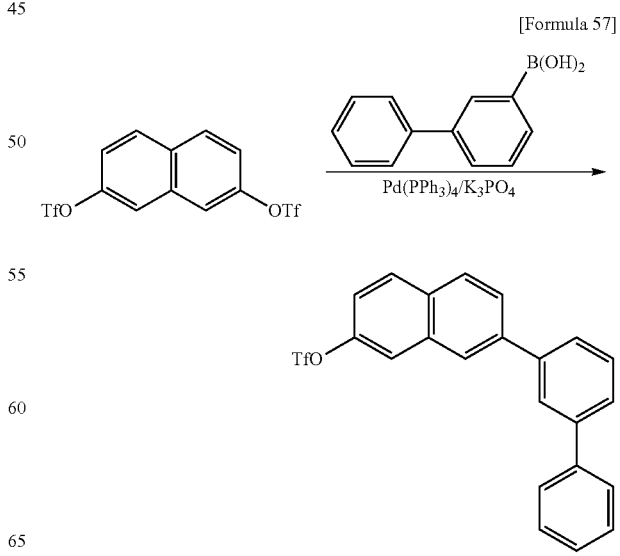

Synthesis of 9-(7-([1,1'-biphenyl]-3-yl)naphthalene-2-yl)-10-(naphthalene-1-yl)anthracene Under the nitrogen atmosphere, 7-([1,1'-biphenyl]-3-yl)naphthalen-2-yl trifluoromethane sulfonate (1.50 g) as the second intermediate compound, (10-(naphthalen-1-yl)anthracen-9-yl)boronic acid (1.22 g), tetrakis(triphenylphosphine)palladium (0) (Pd(PPh$_3$)$_4$) (0.12 g), potassium phosphate (1.49 g), and a mixture solvent (13 ml) of 1,2,4-trimethylbenzene (pseudo cumene), IPA, and water (pseudo cumene/IPA/water=10/2/1 (volume ratio)) were added to a flask and refluxed for 5 hours. Once the heating is completed, the reaction solution was cooled. Liquid separation was performed by adding toluene and water. The organic layer was distilled off under reduced pressure and the resulting solid was washed with methanol and purified by active carbon column chromatography (solvent: toluene) to give 9-(7-([1,1'-biphenyl]-3-yl)naphthalen-2-yl)-10-(naphthalen-1-yl)anthracene (0.7 g) as the target compound represented by Formula (1-2). The scheme is shown in the following "Reaction 3". As for the (10-(naphthalen-1-yl)anthracen-9-yl)boronic acid, a commercially available product was used.

Reaction 3

[Formula 58]

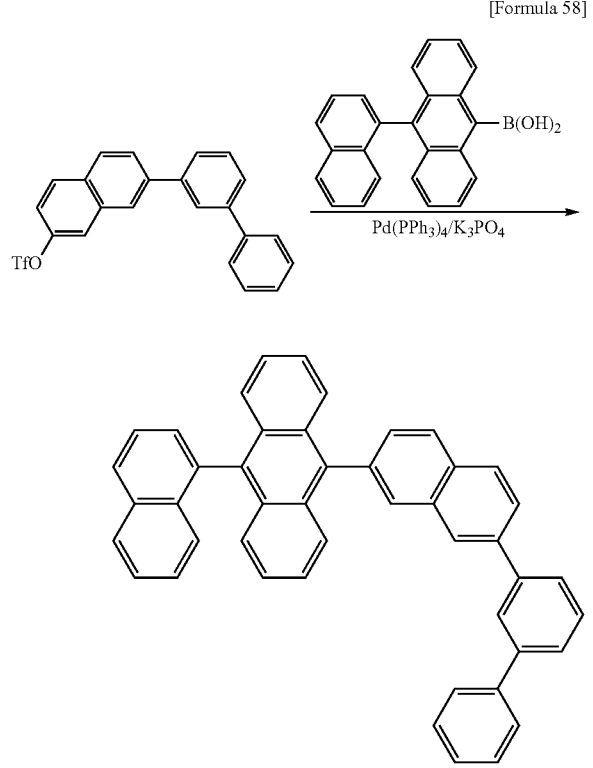

According to MS spectrum and NMR measurement, structure of the target compound (1-2) was determined.

$^1$H-NMR (CDCl$_3$): δ=8.19 (d, 1H), 8.07-8.17 (m, 4H), 8.03 (d, 1H), 7.99 (m, 1H), 7.94 (d, 1H), 7.80 (d, 2H), 7.56-7.78 (m, 8H), 7.45-7.52 (m, 5H), 7.38 (m, 1H), 7.32 (m, 2H), 7.20-7.28 (m, 4H).

Glass transition temperature (Tg) of the target compound (1-2) was 133.4° C.

[Measurement instrument: Diamond DSC (manufactured by PERKIN-ELMER); measurement condition: cooling rate of 200° C./Min., and temperature increase rate of 10° C./Min.]

A Synthetic Example of Compounds Represented by the Formula (1-1)

[Formula 59]

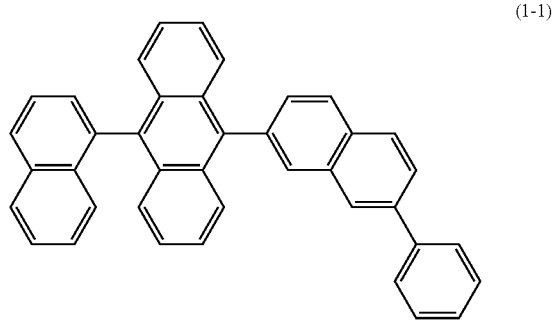

(1-1)

Synthesis of 9-(7-methoxynaphthalene-2-yl)-10-(naphthalene-1-yl)anthracene

Under the nitrogen atmosphere, (10-(naphthalen-1-yl)anthracen-9-yl)boronic acid (25.1 g), 7-methoxynaphthalen-2-yl trifluoromethane sulfonate (24.3 g), Pd(PPh$_3$)$_4$ (0.9 g), potassium phosphate (30.6 g), and a mixture solvent (260 ml) of pseudo cumene, IPA, and water (pseudo cumene/IPA/water=8/4/1 (volume ratio)) were added to a flask and refluxed for 4.5 hours. Once the heating is completed, water was added. After cooling to room temperature, a solid was collected by suction filtration. The obtained solid was washed with water and subsequently with methanol, dissolved in toluene, and purified with a silica gel short column. Crystals obtained by slow distillation of the solvent under reduced pressure were collected by suction filtration to give 9-(7-methoxynaphthalen-2-yl)-10-(naphthalen-1-yl)anthracene (17.5 g) as a third intermediate compound. The scheme is shown in the following "Reaction 4".

Reaction 4

[Formula 60]

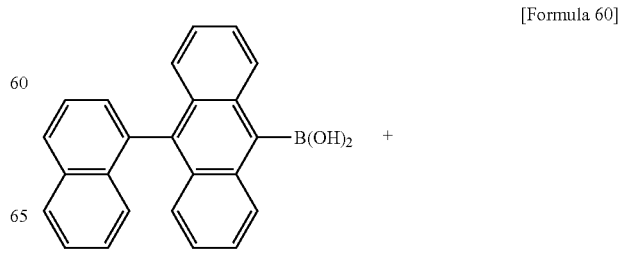

-continued

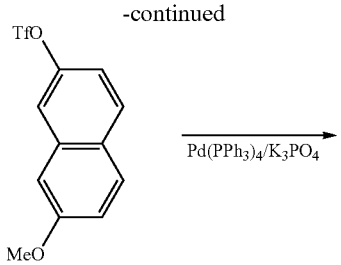

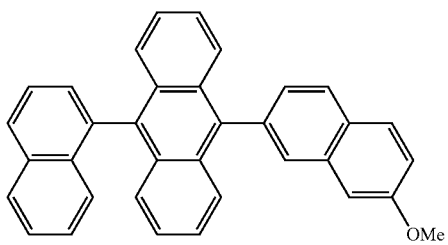

Synthesis of 7-(10-(naphthalene-1-yl)anthracen-9-yl)naphthalene-2-ol

Under the nitrogen atmosphere, 9-(7-methoxynaphthalen-2-yl)-10-(naphthalen-1-yl)anthracene (17.5) as the third intermediate compound, pyridine hydrochloride (22.0 g) and N-methylpyrrolidone (35 ml) were added to a flask and stirred for 6.5 hours at 200° C. Once the heating is completed, the reaction solution was cooled to 100° C. or less, added with water, and the precipitated solid was collected by suction filtration. The crude product obtained was purified by silica gel column chromatography (solvent: toluene) to give 7-(10-(naphthalen-1-yl)anthracen-9-yl)naphthalene-2-ol (16.0 g) as a fourth intermediate compound. The scheme is shown in the following "Reaction 5".

Reaction 5

[Formula 61]

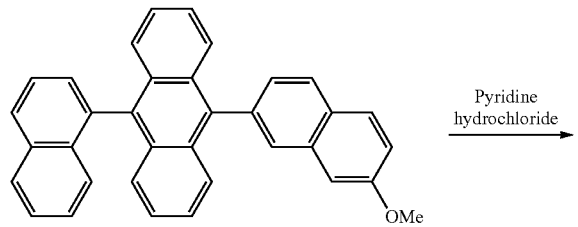

Synthesis of 7-(10-(naphthalene-1-yl)anthracen-9-yl)naphthalene-2-yl trifluoromethanesulfonate Under the nitrogen atmosphere, 7-(10-(naphthalen-1-yl)anthracen-9-yl) naphthalene-2-ol (16.0 g) as the fourth intermediate compound and pyridine (150 ml) were added to a flask. After cooling to 0° C., trifluoromethane sulfonic acid anhydride (15.2 g) was slowly added dropwise thereto. After stirring for 3 hours at room temperature, it was cooled again to 0° C. and the reaction was terminated by adding water. The target compound was extracted with toluene. The crude product obtained by concentration of organic layer under reduced pressure was purified by silica gel column chromatography (solvent: toluene) to give 7-(10-(naphthalen-1-yl)anthracen-9-yl)naphthalen-2-yl trifluoromethane sulfonate (20.0 g) as a fifth intermediate compound. The scheme is shown in the following "Reaction 6".

Reaction 6

[Formula 62]

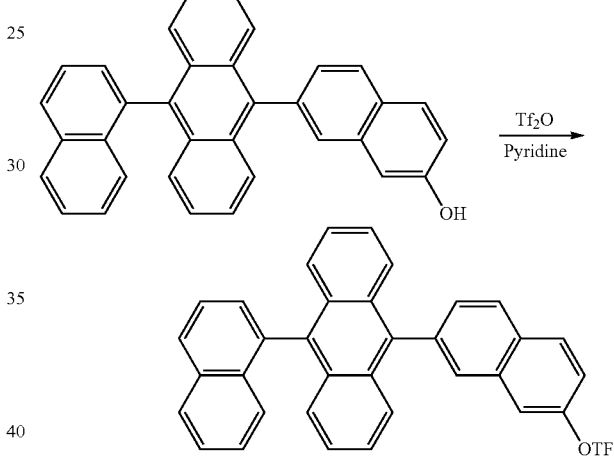

Synthesis of 9-(naphthalene-1-yl)-10-(7-phenylnaphthalene-2-yl)anthracene

Under the nitrogen atmosphere, (7-(10-(naphthalen-1-yl)anthracen-9-yl)naphthalen-2-yl trifluoromethane sulfonate (3.0 g) as the fifth intermediate compound, phenylboronic acid (0.8 g), bis(dibenzylideneacetone)palladium (0) (Pd(dba)$_2$) (0.03 g), tricyclohexyl phosphine (PCy$_3$) (0.03 g), potassium phosphate (2.2 g), and a mixture solvent (22 ml) of toluene, ethanol, and water (toluene/ethanol/water=9/1/1 (volume ratio)) were added to a flask and refluxed for 2.5 hours. Once the heating is completed, the reaction solution was cooled to room temperature and added with methanol. The precipitates were collected by suction filtration. The obtained solid was washed with water followed by methanol, and washed further with ethyl acetate. The obtained crude product was dissolved in toluene, and colored components were removed by passing through an active carbon short column. After re-crystallization with chlorobenzene, 9-(naphthalen-1-yl)-10-(7-phenylnaphthalen-2-yl)anthracene (1.2 g) was obtained as the target compound represented by Formula (1-1). The scheme is shown in the following "Reaction 7".

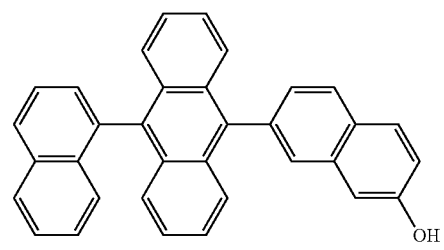

Reaction 7

[Formula 63]

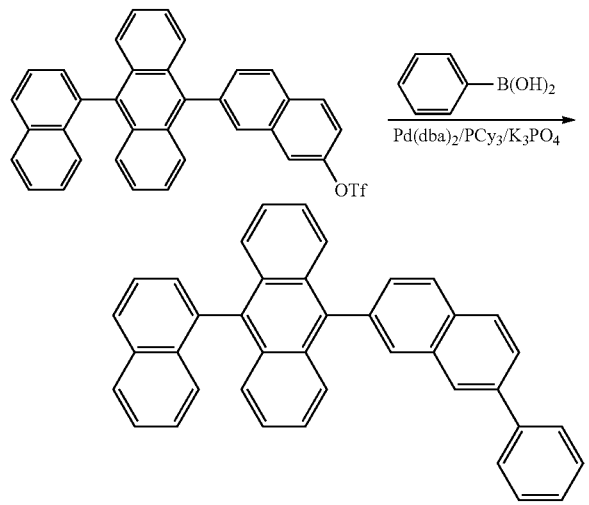

According to NMR measurement, structure of the target compound (1-1) was determined.

$^1$H-NMR (CDCl$_3$): δ=8.07-8.17 (m, 5H), 8.04 (d, 1H), 7.89 (dd, 1H), 7.76-7.82 (m, 4H), 7.65-7.75 (m, 2H), 7.61 (d, 1H), 7.46-7.54 (m, 5H), 7.41 (m, 1H), 7.29-7.33 (m, 2H), 7.20-7.28 (m, 4H).

Synthetic Example of Compounds Represented by the Formula (1-34)>

[Formula 64]

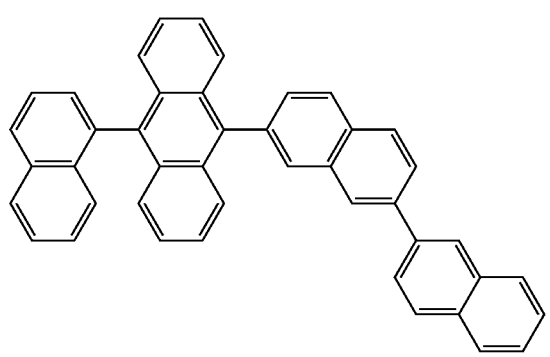

(1-34)

Synthesis of 9-([2,2'-binaphthalene]-7-yl)-10-(naphthalene-1-yl)anthracene

Under the nitrogen atmosphere, 7-(10-(naphthalen-1-yl)anthracen-9-yl)naphthalen-2-yl trifluoromethane sulfonate (3.0 g) as the fifth intermediate compound, 2-naphthalene boronic acid (1.0 g), (Pd(dba)$_2$) (0.03 g), tricyclohexyl phosphine (0.03 g), potassium phosphate (2.2 g) and a mixture solvent (22 ml) of toluene, ethanol and water (toluene/ethanol/water=9/1/1 (volume ratio)) were added to a flask and refluxed for 3 hours. Once the heating is completed, the reaction solution was cooled to room temperature and added with methanol. The precipitates were collected by suction filtration. The obtained solid was washed with water followed by methanol, and washed further with ethyl acetate. The obtained crude product was dissolved in chlorobenzene, and colored components were removed by passing through a silica gel short column. After re-crystallization with chlorobenzene, 9-([2,2'-binaphthalen]-7-yl)-10-(naphthalen-1-yl)anthracene (1.5 g) was obtained as the target compound represented by Formula (1-34). The scheme is shown in the following "Reaction 8".

Reaction 8

[Formula 65]

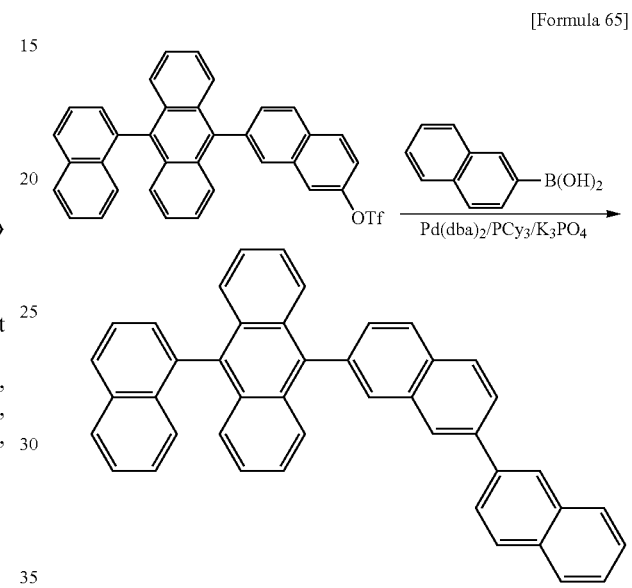

According to NMR measurement, structure of the target compound (1-34) was determined.

$^1$H-NMR (CDCl$_3$): δ=8.26 (dd, 1H), 8.24 (s, 1H), 8.11-8.18 (m, 3H), 8.08 (d, 1H), 7.88-8.05 (m, 6H), 7.81 (dd, 2H), 7.66-7.75 (m, 2H), 7.61 (d, 1H), 7.46-7.56 (m, 5H), 7.29-7.34 (m, 2H), 7.20-7.28 (m, 4H).

Synthetic Example of Compounds Represented by the Formula (1-21)

[Formula 66]

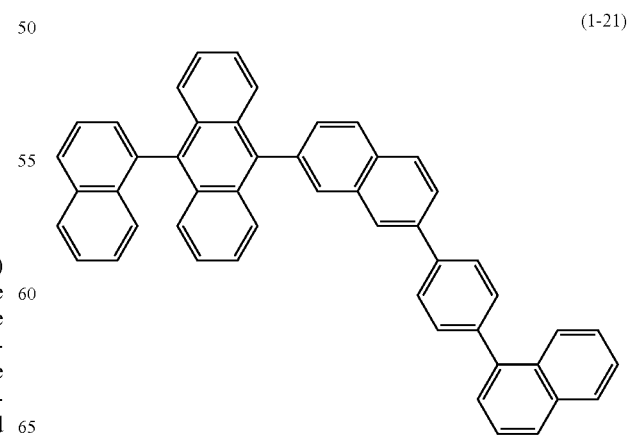

(1-21)

Synthesis of 9-(naphthalene-1-yl)-10-(7-(naphthalene-1-yl)phenyl) naphthalene-2-yl anthracene Under the nitrogen atmosphere, 7-(10-(naphthalen-1-yl) anthracen-9-yl)naphthalen-2-yl trifluoromethane sulfonate (3.0 g) as the fifth intermediate compound, (4-(naphthalen-1-yl)phenyl)boronic acid (1.9 g), bis(dibenzylideneacetone) palladium (0) (Pd(dba)$_2$) (0.03 g), tricyclohexyl phosphine (0.03 g), potassium phosphate (2.2 g) and a mixture solvent (22 ml) of toluene, ethanol, and water (toluene/ethanol/water=9/1/1 (volume ratio)) were added to a flask and refluxed for 6.5 hours. Once the heating is completed, the reaction solution was cooled to room temperature and added with methanol. The precipitates were collected by suction filtration. The obtained solid was washed with water followed by methanol, and washed further with ethyl acetate. The obtained crude product was dissolved in toluene, and colored components were removed by passing through a silica gel short column. The solvent was distilled off under reduced pressure. The obtained oily phase substance was added with ethyl acetate and the precipitated products were collected by suction filtration to give 9-(naphthalen-1-yl)-10-(7-(naphthalen-1-yl)phenyl)naphthalen-2-yl)anthracene (2.6 g) as the target compound represented by Formula (1-21). The scheme is illustrated in the following "Reaction 9".

Reaction 9

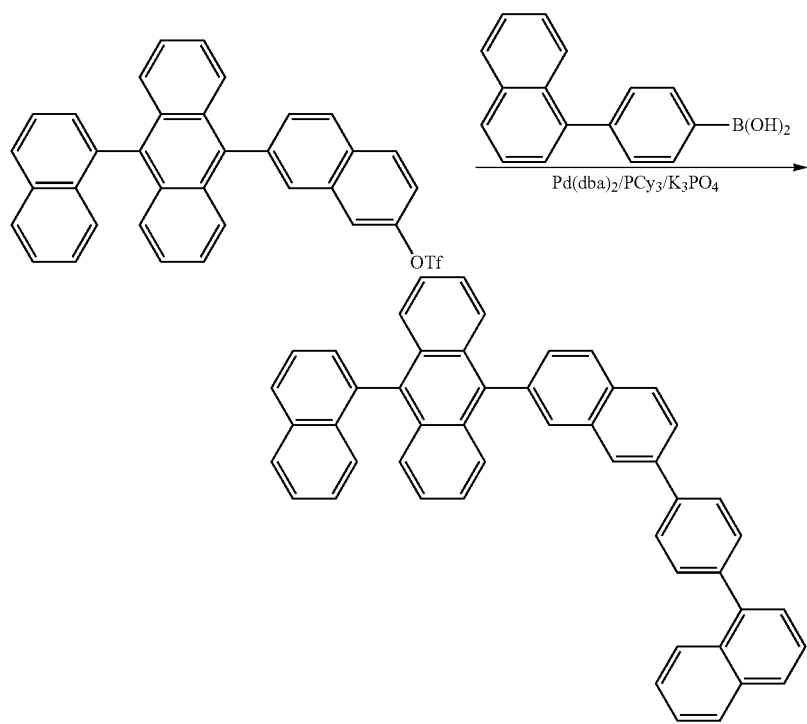

According to NMR measurement, structure of the target compound (1-21) was determined.

$^1$H-NMR (CDCl$_3$): δ=8.24 (d, 1H), 8.12-8.19 (m, 3H), 8.09 (d, 1H), 8.03 (m, 2H), 7.99 (dd, 1H), 7.88-7.96 (m, 4H)7.83 (d, 2H), 7.64-7.76 (m, 4H), 7.62 (d, 1H), 7.46-7.59 (m, 7H), 7.31-7.35 (m, 2H), 7.20-7.28 (m, 4H), 7.83 (d, 2H), 7.64-7.76 (m, 4H), 7.62 (d, 1H), 7.46-7.59 (m, 7H), 7.31-7.35 (m, 2H), 7.20-7.28 (m, 4H).

Synthetic Example of Compounds Represented by the Formula (1-38)

[Formula 68]

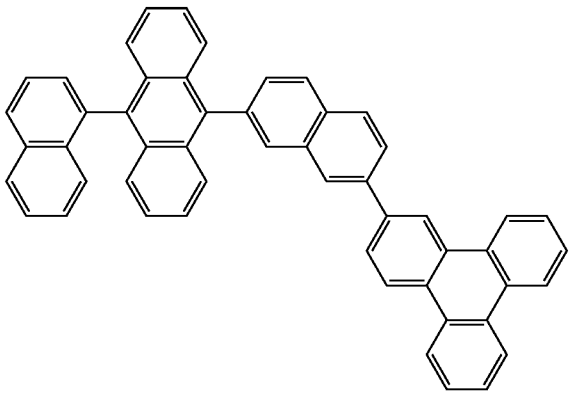

(1-38)

Synthesis of 2-(7-(10-(naphthalene-1-yl)anthracen-9-yl)naphthalene-2-yl)triphenylene Under the nitrogen atmosphere, 7-(10-(naphthalen-1-yl) anthracen-9-yl)naphthalen-2-yl trifluoromethane sulfonate (3.0 g) as the fifth intermediate compound, 2-triphenylene boronic acid (2.1 g), Pd(dba)$_2$ (0.03 g), tricyclohexyl phosphine (0.03 g), potassium phosphate (2.2 g), and a mixture solvent (22 ml) of toluene, ethanol and water (toluene/ethanol/water=9/1/1 (volume ratio)) were added to a flask and refluxed for 2 hours. Once the heating is completed, the reaction solution was cooled to room temperature and added with methanol. The precipitates were collected by suction filtration. The obtained solid was washed with water followed by methanol, and washed further with ethyl acetate. The obtained crude product was dissolved in chlorobenzene, and colored components were removed by passing through a silica gel short column. After re-crystallization with chlorobenzene, 2-(7-(10-(naphthalen-1-yl)anthracen-9-yl)naphthalen-2-yl)triphenylene (1.9 g) was obtained as the target compound represented by Formula (1-38). The scheme is shown in the following "Reaction 10".

Reaction 10

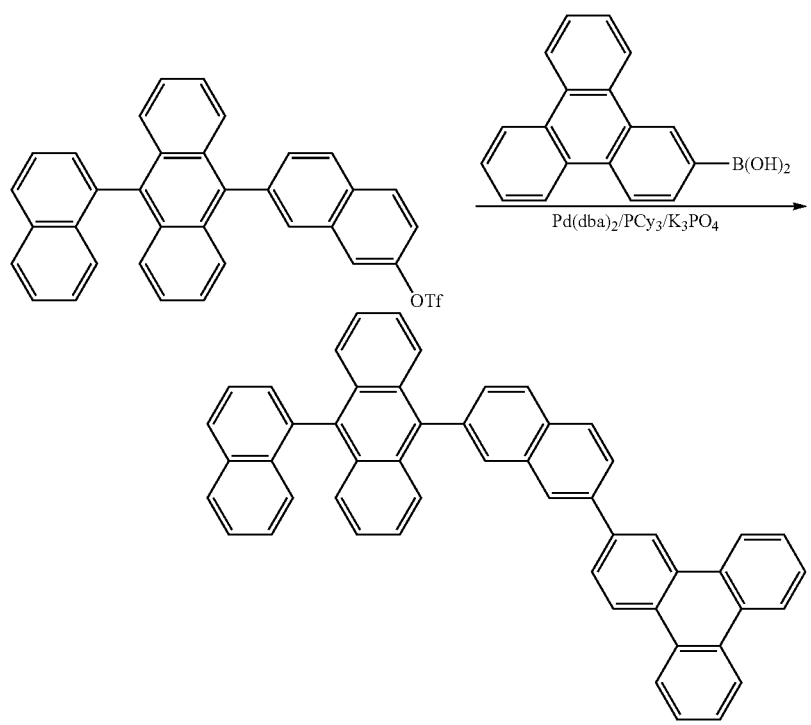

According to NMR measurement, structure of the target compound (1-38) was determined.

$^1$H-NMR (CDCl$_3$): δ=9.75 (s, 1H), 8.68-8.90 (m, 6H), 8.38 (m, 1H), 8.02-8.30 (m, 8H), 7.60-7.90 (m, 10H), 7.53 (m, 3H), 7.35 (m, 3H).

Synthetic Example of Compounds Represented by the Formula (1-160)

[Formula 70]

(1-160)

Synthesis of synthesis of 7-methoxy-2,2'-binaphthalene

Under the nitrogen atmosphere, 2-naphthalene boronic acid (33.7 g), naphthalene-2,7-diyl-bis(trifluoromethane sulfonate) (50.0 g), Pd(PPh$_3$)$_4$ (5.7 g), potassium phosphate (69.3 g) and a mixture solvent (400 ml) of toluene and ethanol (toluene/ethanol=5/1 (volume ratio)) were added to a flask and then refluxed for 7 hours. Once the heating is completed, the reaction solution was cooled and added with water. The target component was extracted with toluene. Subsequently, the organic layer was concentrated under reduced pressure and purified by silica gel column chromatography (solvent: toluene) to give 7-methoxy-2,2'-binaphthalene (32.0 g) as a sixth intermediate compound. The scheme is shown in the following "Reaction 11".

Reaction 11

[Formula 71]

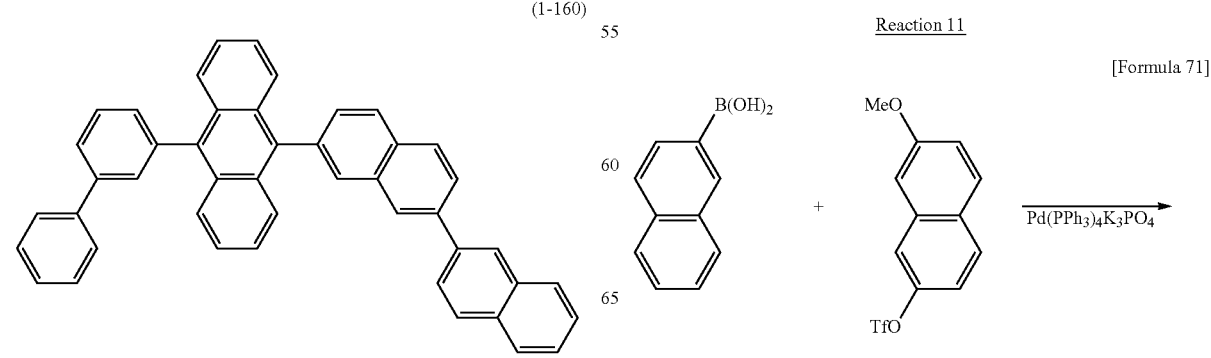

-continued

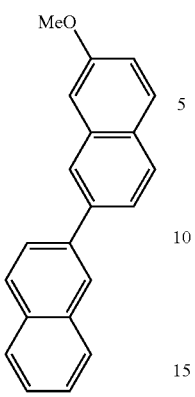

Synthesis of [2,2'-binaphthalene]-7-ol

Under the nitrogen atmosphere, 7-methoxy-2,2'-binaphthalen (31.0) as the sixth intermediate compound, pyridine hydrochloride (63.0 g) and N-methylpyrrolidone (20 ml) were added to a flask and then stirred for 7 hours at 200° C. Once the heating is completed, it was cooled to 100° C. or less and added with water. The solid precipitated by adding water was collected by suction filtration. The obtained solid was purified by silica gel column chromatography (solvent: toluene) to give [2,2'-binaphthalen]-7-ol (22.0 g) as a seventh intermediate compound. The scheme is shown in the following "Reaction 12".

Reaction 12

[Formula 72]

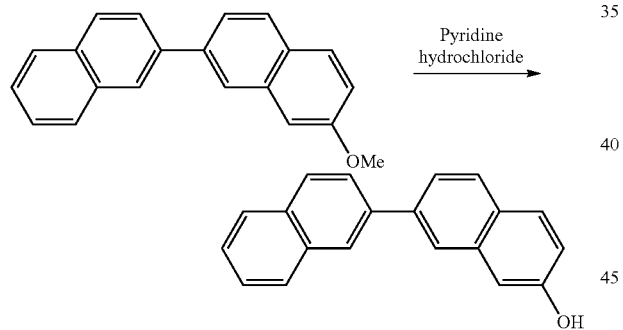

Synthesis of [2,2'-binaphthalene]-7-yl trifluoromethanesulfonate

Under the nitrogen atmosphere, [2,2'-binaphthalen]-7-ol (20.0 g) as the seventh intermediate compound and pyridine (200 ml) were added to a flask. After cooling to 0° C., trifluoromethane sulfonic acid anhydride (30.2 g) was slowly added dropwise thereto. After that, the mixture was stirred for 2 hours at room temperature, cooled again to 0° C., and then added with water to terminate the reaction. The target component was extracted with toluene. Subsequently, the organic layer was concentrated under reduced pressure and purified by silica gel column chromatography (solvent: toluene). The obtained crude product was dissolved in acetone and subjected to re-precipitation by adding heptane. As a result, [2,2'-binaphthalen]-7-yl trifluoromethane sulfonate (16.2 g) was obtained as an eighth intermediate compound. The scheme is shown in the following "Reaction 13".

Reaction 13

[Formula 73]

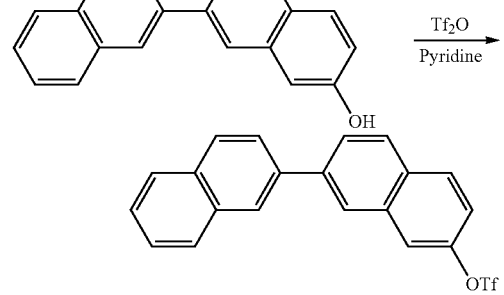

Synthesis of 9-([2,2'-binaphthalene]-7-yl)anthracene

Under the nitrogen atmosphere, [2,2'-binaphthalen]-7-yl trifluoromethane sulfonate (16.0 g) as the eighth intermediate compound, anthracen-9-ylboronic acid (13.3 g), $Pd(dba)_2$ (0.7 g), tricyclohexyl phosphine (0.8 g), potassium phosphate (16.9 g), and a mixture solvent (120 ml) of toluene and ethanol (toluene/ethanol=4/1 (volume ratio)) were added to a flask and refluxed for 2.5 hours. Once the heating is completed, the reaction solution was cooled. Liquid separation was performed by adding water and toluene. Subsequently, the organic layer was distilled off under reduced pressure and the obtained crude product was purified by silica gel column chromatography (solvent: toluene). The solid obtained by distillation of the solvent under reduced pressure was washed with heptane to give 9-([2,2'-binaphthalen]-7-yl)anthracene (10.0 g) as a ninth intermediate compound. The scheme is shown in the following "Reaction 14".

Reaction 14

[Formula 74]

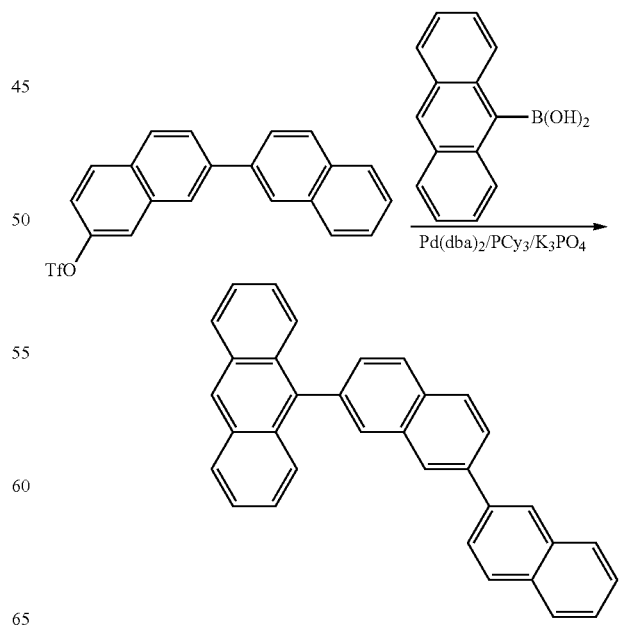

Synthesis of 9-([2,2'-binaphthalene]-7-yl)-10-bromoanthracene

Under the nitrogen atmosphere, 9-([2,2'-binaphthalen]-7-yl) anthracene (10.0 g) as the ninth intermediate compound, N-bromosuccinimide (NBS) (4.6 g), iodine (0.1 g), and THF (60 ml) were added to a flask and stirred overnight at room temperature. By adding an aqueous solution of sodium thiosulfate, the reaction was terminated. Liquid separation was performed by adding water and toluene. Subsequently, the solid obtained by distillation of the organic layer under reduced pressure was purified by silica gel column chromatography (solvent: toluene). The solid obtained by distillation of the solvent under reduced pressure was washed with heptane to give 9-([2,2'-binaphthalen]-7-yl)-10-bromoanthracene (11.0 g) as a tenth intermediate compound. The scheme is shown in the following "Reaction 15".

Reaction 15

[Formula 75]

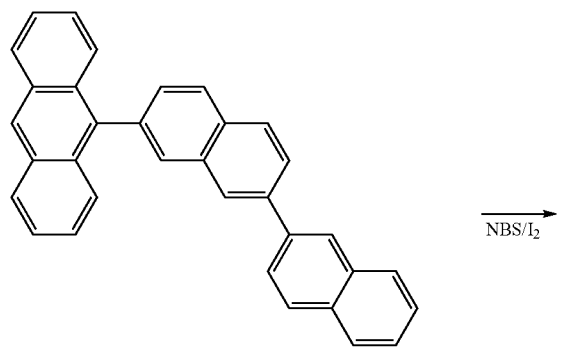

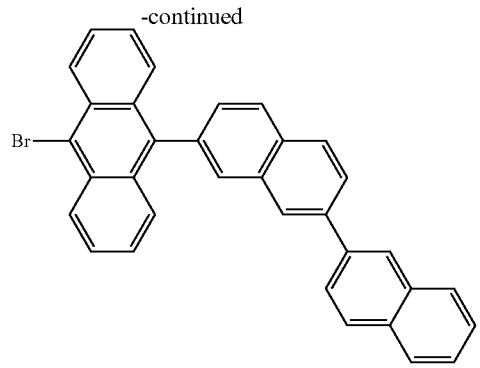

Synthesis of 9-([1,1'-biphenyl]-3-yl)-10-([2,2'-binaphthalene]-7-yl)anthracene Under the nitrogen atmosphere, ([9-([2,2'-binaphthalen]-7-yl)-10-bromoanthracene (2.0 g) as the tenth intermediate compound, m-biphenylboronic acid (1.4 g), Pd(PPh$_3$)$_4$ (0.1 g), potassium phosphate (1.7 g), and a mixture solvent (16 ml) of toluene and ethanol (toluene/ethanol=4/1 (volume ratio)) were added to a flask and refluxed for 10 hours. Once the heating is completed, the reaction solution was cooled to room temperature and added with water. The precipitates were collected by suction filtration. The obtained solid was washed with water followed by methanol, and washed further with ethyl acetate. The obtained crude product was purified by silica gel column chromatography (solvent: chlorobenzene). Finally, after re-crystallization with chlorobenzene, 9-([1,1'-biphenyl]-3-yl)-10-([2,2'-binaphthalen]-7-yl)anthracene (0.5 g) was obtained as the target compound represented by Formula (1-160). The scheme is shown in the following "Reaction 16".

Reaction 16

[Formula 76]

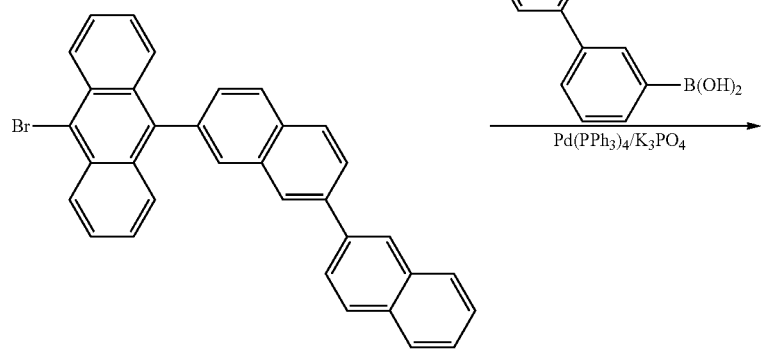

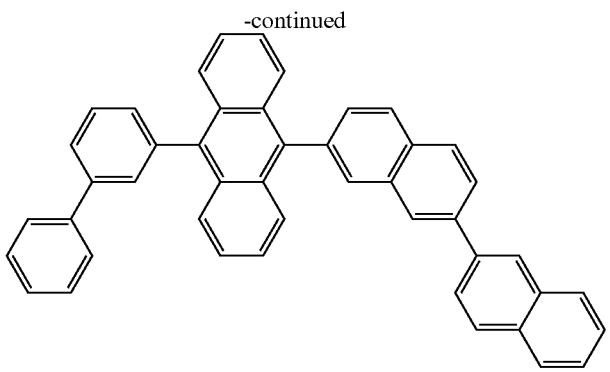

According to NMR measurement, structure of the target compound (1-160) was determined.

¹H-NMR (CDCl₃): δ=8.24 (d, 2H), 8.14 (t, 2H), 8.09 (m, 1H), 7.88-8.15 (m, 5H), 7.76-7.84 (m, 6H), 7.71 (m, 3H), 7.64 (m, 1H), 7.44-7.56 (m, 5H), 7.32-7.38 (m, 5H).

Synthetic Example of Compounds Represented by the Formula (1-162)

[Formula 77]

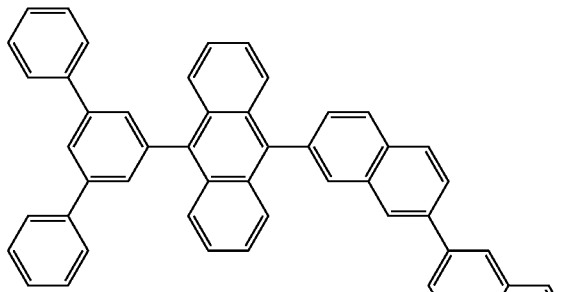

(1-162)

Synthesis of 9-([1,1':3',1''-terphenyl]-5'-yl)-10-([2,2'-binaphthalene]-7-yl)anthracene Under the nitrogen atmosphere, [9-([2,2'-binaphthalen]-7-yl)-10-bromoanthracene (2.0 g) as the tenth intermediate compound, [1,1':3',1''-terphenyl]-5'-ylboronic acid (1.0 g), Pd(dba)₂ (0.03 g), tricyclohexyl phosphine (0.03 g), potassium phosphate (1.3 g), and a mixture solvent of toluene and ethanol (20 ml) (toluene/ethanol=4/1 (volume ratio)) were added to a flask and refluxed for 2 hours. Once the heating is completed, the reaction solution was cooled to room temperature. The reaction was terminated by adding water. The target compound was extracted with toluene. The solvent was distilled off under reduced pressure, and the obtained crude product was purified by silica gel column chromatography (solvent: toluene) and also by active carbon column chromatography (solvent: toluene) to give 9-([1,1':3',1''-terphenyl]-5'-yl)-10-([2,2'-binaphthalen]-7-yl)anthracene (1.0 g) as the target compound represented by Formula (1-162). The scheme is shown in the following "Reaction 17".

Reaction 17

[Formula 78]

According to NMR measurement, structure of the target compound (1-162) was determined.

¹H-NMR (CDCl₃): δ=8.22-8.27 (m, 2H), 8.14 (t, 2H), 8.09 (s, 1H), 8.05 (m, 1H), 8.02 (dd, 1H), 7.88-8.00 (m, 6H), 7.76-7.81 (m, 8H), 7.65 (dd, 1H), 7.46-7.55 (m, 6H), 7.33-7.41 (m, 6H).

147

Synthetic Example of Compounds Represented by the Formula (1-164)

[Formula 79]

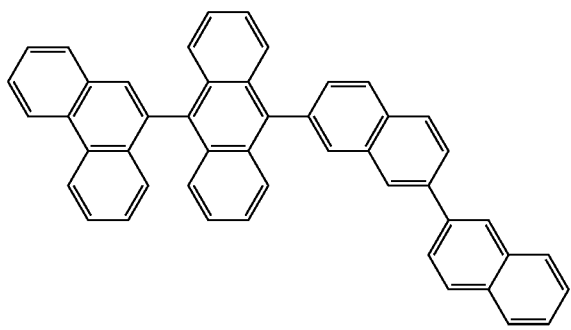

(1-164)

Synthesis of 9-([2,2'-binaphthalene]-7-yl)-10-(phenanthrene-9-yl)anthracene

Under the nitrogen atmosphere, [9-([2,2'-binaphthalen]-7-yl)-10-bromoanthracene (2.0 g) as the tenth intermediate compound, phenanthren-9-ylboronic acid (1.1 g), palladium acetate (Pd (OAc)$_2$) (0.06 g), 2-dicyclohexylphosphino-2',6'-dimethoxybiphenyl (SPhos, manufactured by Aldrich Company) (0.02 g), potassium phosphate (1.7 g), and a mixture solvent (10 ml) of toluene and ethanol (toluene/ethanol=4/1 (volume ratio)) were added to a flask and refluxed for 10 hours. Once the heating is completed, the reaction solution was cooled to room temperature and added with water. The precipitates were collected by suction filtration. The obtained solid was washed with water followed by methanol, and then purified by silica gel column chromatography (solvent: toluene). Additionally, after re-crystallization with chlorobenzene, 9-([2,2'-binaphthalen]-7-yl)-10-(phenanthren-9-yl)anthracene (0.7 g) was obtained as the target compound represented by Formula (1-164). The scheme is shown in the following "Reaction 18".

Reaction 18

[Formula 80]

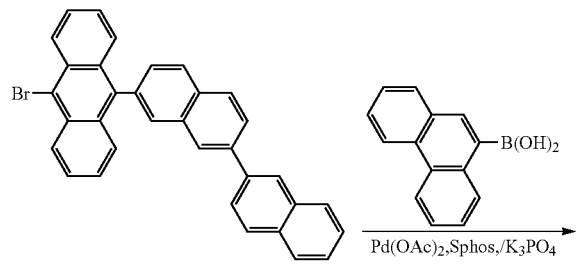

148

-continued

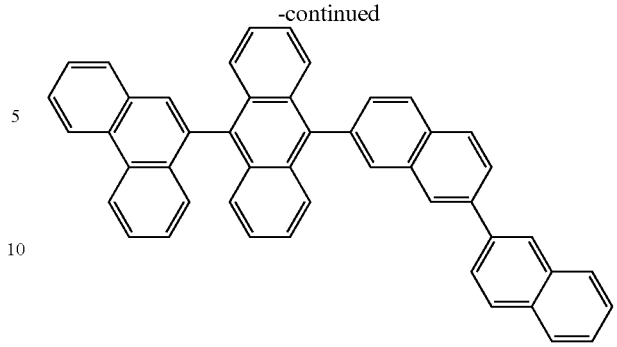

According to NMR measurement, structure of the target compound (1-164) was determined.

$^1$H-NMR (CDCl$_3$): δ=8.90 (m, 2H), 8.28 (m, 1H), 8.25 (s, 1H), 8.13-8.20 (m, 3H), 7.89-8.04 (m, 7H), 7.83 (d, 2H), 7.66-7.81 (m, 4H), 7.62 (d, 2H), 7.53 (m, 2H), 7.28-7.38 (m, 4H), 7.23 (m, 2H).

Synthetic Example of Compounds Represented by the Formula (1-117)

[Formula 81]

(1-117)

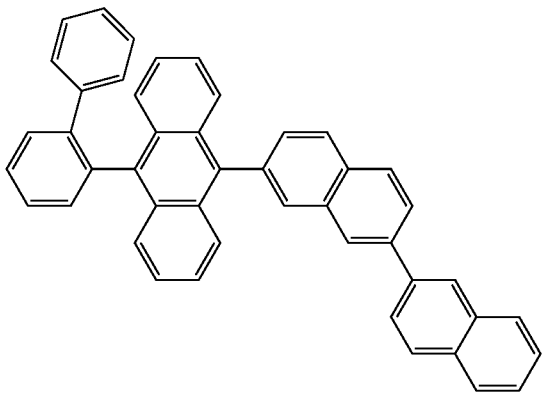

Synthesis of 9-([1,1'-biphenyl]-2-yl)-10-([2,2'-binaphthalene]-7-yl)anthracene Under the nitrogen atmosphere, [9-([2,2'-binaphthalen]-7-yl)-10-bromoanthracene (2.0 g) as the tenth intermediate compound, o-biphenylboronic acid (0.9 g), Pd(OAc)$_2$ (0.03 g), SPhos (manufactured by Aldrich Company) (0.12 g), potassium phosphate (1.7 g), and a mixture solvent of pseudo cumene, t-butyl alcohol, and water (14 ml) (pseudo cumene/t-butyl alcohol/water=10/3/1 (volume ratio)) were added to a flask and refluxed for 8 hours. Once the heating is completed, the reaction solution was cooled to room temperature. The reaction was terminated by adding water. The target compound was extracted with toluene. The solvent was distilled off under reduced pressure, and the obtained solid was purified by silica gel column chromatography (solvent: toluene) and further by active carbon column chromatography (solvent: toluene) to give 9-([1,1'-biphenyl]-2-yl)-10-([2,2'-binaphthalen]-7-yl)]anthracene (0.5 g) as the target compound represented by Formula (1-117). The scheme is shown in the following "Reaction 19".

Reaction 19

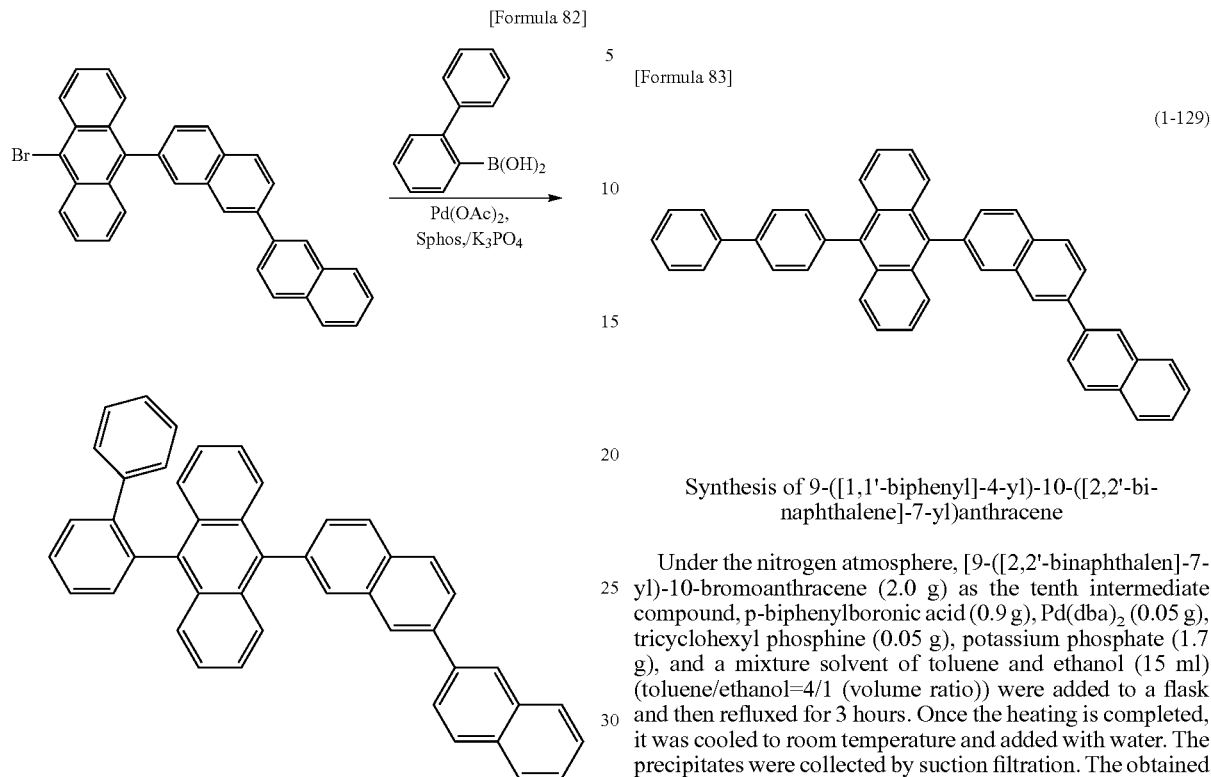

According to NMR measurement, structure of the target compound (1-117) was determined.

$^1$H-NMR (CDCl$_3$): δ=8.21 (m, 2H), 8.12 (d, 1H), 8.08 (dd, 1H), 7.87-8.03 (m, 6H), 7.71 (d, 2H), 7.67 (m, 4H), 7.45-7.59 (m, 5H), 7.23-7.32 (m, 4H), 7.03 (m, 2H), 6.88-6.97 (m, 3H).

Synthetic Example of Compounds Represented by the Formula (1-129)

Synthesis of 9-([1,1'-biphenyl]-4-yl)-10-([2,2'-binaphthalen]-7-yl)anthracene

Under the nitrogen atmosphere, [9-([2,2'-binaphthalen]-7-yl)-10-bromoanthracene (2.0 g) as the tenth intermediate compound, p-biphenylboronic acid (0.9 g), Pd(dba)$_2$ (0.05 g), tricyclohexyl phosphine (0.05 g), potassium phosphate (1.7 g), and a mixture solvent of toluene and ethanol (15 ml) (toluene/ethanol=4/1 (volume ratio)) were added to a flask and then refluxed for 3 hours. Once the heating is completed, it was cooled to room temperature and added with water. The precipitates were collected by suction filtration. The obtained solid was washed with water followed by methanol and purified by silica gel column chromatography (solvent: toluene) and further by active carbon column chromatography (solvent: toluene) to give 9-([1,1'-biphenyl]-4-yl)-10-([2,2'-binaphthalen]-7-yl)anthracene (0.6 g) as the target compound represented by Formula (1-129). The scheme is shown in the following "Reaction 20".

Reaction 20

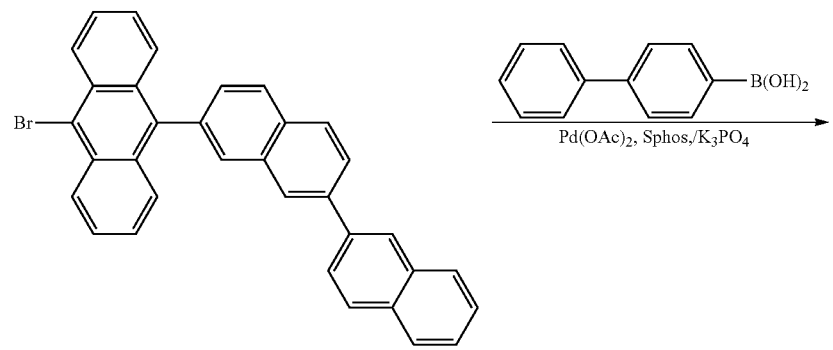

-continued

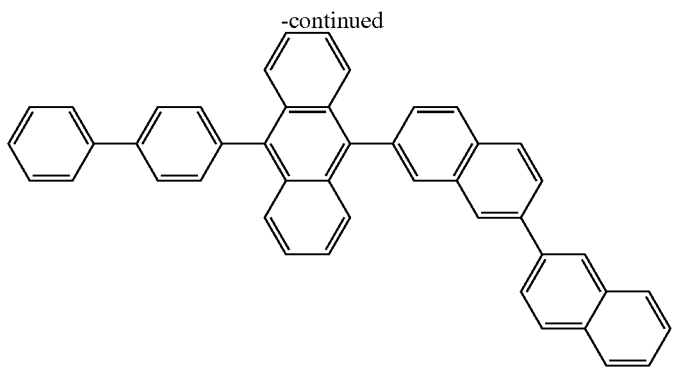

According to NMR measurement, structure of the target compound (1-129) was determined.

$^1$H-NMR (CDCl$_3$): δ=8.24 (d, 2H), 8.12 (t, 2H), 8.09 (s, 1H), 7.88-8.03 (m, 5H), 7.86 (d, 2H), 7.83 (d, 2H), 7.79 (m, 4H), 7.64 (dd, 1H), 7.60 (d, 2H), 7.48-7.56 (m, 4H), 7.43 (t, 1H), 7.33-7.40 (m, 4H).

Synthetic Example of Compounds Represented by the Formula (1-166)

[Formula 85]

(1-166)

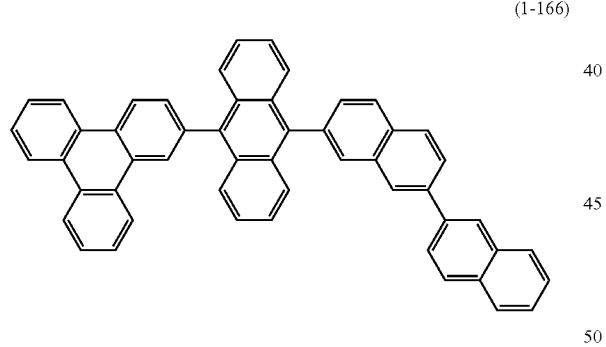

Synthesis of 2-(anthracen-9-yl)triphenylene

Under the nitrogen atmosphere, triphenylen-2-ylboronic acid (5.6 g), 9-bromoanthracene (3.5 g), (Pd(PPh$_3$)$_4$) (0.5 g), potassium phosphate (5.8 g), and a mixture solvent of pseudo cumene, t-butyl alcohol, and water (48 ml) (pseudo cumene/t-butyl alcohol/water=10/1/1 (volume ratio)) were added to a flask and then refluxed for 8 hours. After adding water, the precipitates were collected by suction filtration. The obtained solid was washed with water followed by methanol and purified by silica gel column chromatography (solvent: toluene). After re-crystallization with a mixture solution of toluene/ethyl acetate, 2-(anthracen-9-yl)triphenylene (3.3 g) was obtained as an eleventh intermediate compound. The scheme is represented in the following "Reaction 21".

Reaction 21

[Formula 86]

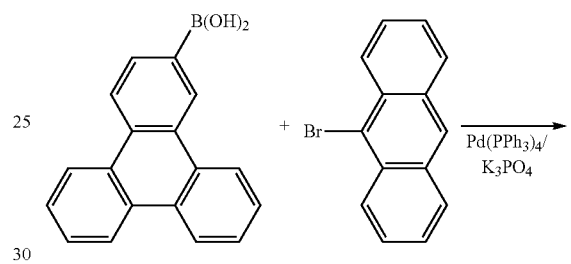

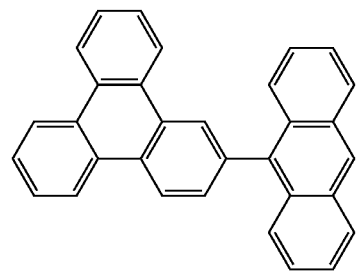

Synthesis of 2-(10-bromoanthracen-9-yl)triphenylene

Under the nitrogen atmosphere, 2-(anthracen-9-yl)triphenylene (3.3 g) as the eleventh intermediate compound, N-bromosuccinimide (NBS) (1.7 g), iodine (0.1 g) and THF (25 ml) were added to a flask, and stirred at room temperature for 5 hours. An aqueous solution of sodium thiosulfate was added and the reaction was terminated. The precipitates were collected by suction filtration. The obtained solid was washed with methanol and subsequently with heptane and purified by silica gel column chromatography (solvent: toluene) to give 2-(10-bromoanthracen-9-yl)triphenylene (3.5 g) as a twelfth intermediate compound. The scheme is shown in the following "Reaction 22".

Reaction 22

[Formula 87]

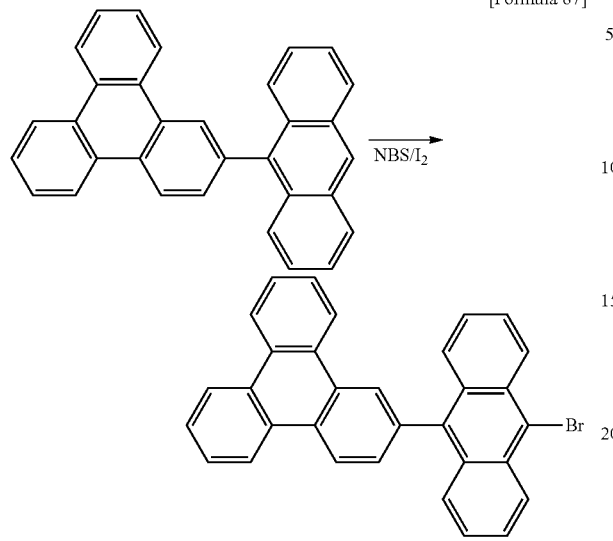

Synthesis of 4,4,5,5-tetramethyl-2-(10-(triphenylene-2-yl)anthracen-9-yl)-1,3,2-dioxaborolan Under the nitrogen atmosphere, 2-(10-bromoanthracen-9-yl)triphenylene (3.5 g) as the twelfth intermediate compound, bispinacolate diborone (2.2 g), PdCl$_2$ (dppf) (0.2 g), potassium carbonate (2.0 g), potassium acetate (1.4 g) and cyclopentyl methyl ether (20 ml) were added to a flask and refluxed for 5 hours. After that, the reaction solution was cooled to room temperature. Liquid separation was performed by adding water and toluene. The solvent was distilled off under reduced pressured. The obtained crude product was purified by active carbon column chromatography (solvent: toluene) to give 4,4,5,5-tetramethyl-2-(10-(triphenylen-2-yl)anthracen-9-yl)-1,3,2-dioxaborolane (2.0 g) as a thirteenth intermediate compound. The scheme is shown in the following "Reaction 23".

Reaction 23

[Formula 88]

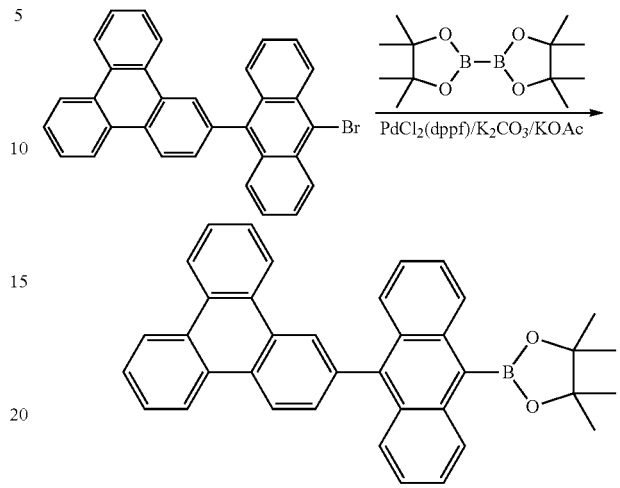

Synthesis of 2-(10-([2,2'-binaphthalene]-7-yl)anthracen-9-yl)triphenylene

Under the nitrogen atmosphere, 4,4,5,5-tetramethyl-2-(10-(triphenylen-2-yl)anthracen-9-yl)-1,3,2-dioxaborolane (1.5 g) as the thirteenth intermediate compound, [2,2'-binaphthalen]-7-yl trifluoromethane sulfonate (1.3 g), Pd(PPh$_3$)$_4$ (0.2 g), potassium phosphate (1.2 g), and a mixture solvent (11 ml) of toluene, ethanol, and water (toluene/ethanol/water=8/2/1 (volume ratio)) were added to a flask and refluxed for 4 hours. Once the heating is completed, the reaction solution was cooled to room temperature and added with water. The precipitates were collected by suction filtration. The obtained solid was washed with water followed by methanol. It was then dissolved in chlorobenzene and passed through active alumina column chromatography (solvent: toluene). Additionally, after re-crystallization with chlorobenzene, 2-(10-([2,2'-binaphthalen]-7-yl)anthracen-9-yl)triphenylene (0.9 g) was obtained as the target compound represented by Formula (1-166). The scheme is represented in the following "Reaction 24".

Reaction 24

[Formula 89]

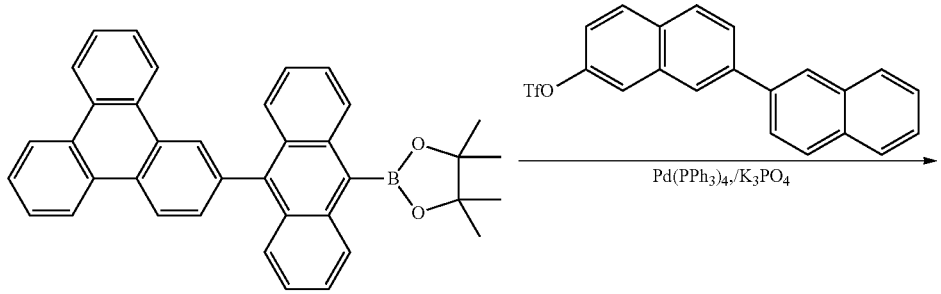

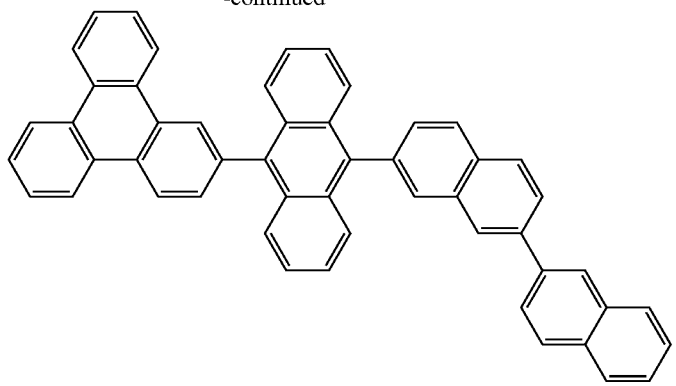

According to NMR measurement, structure of the target compound (1-166) was determined.

$^1$H-NMR (CDCl$_3$): δ=8.93 (d, 1H), 8.83 (m, 2H), 8.74 (m, 2H), 8.61 (d, 1H), 8.28 (m, 1H), 8.24 (m, 1H), 8.15 (m, 3H), 7.90-8.05 (m, 5H), 7.80-7.87 (m, 5H), 7.76 (m, 2H), 7.69 (m, 2H), 7.61 (t, 1H), 7.52 (m, 2H), 7.36 (m, 4H).

Synthetic Example of Compounds Represented by the Formula (1-172)

[Formula 90]

(1-172)

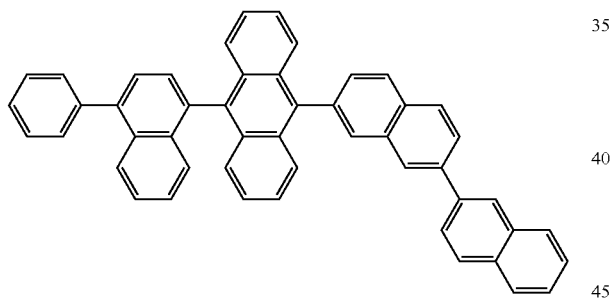

Synthesis of 9-(4-ethoxynaphthalene-1-yl)anthracene 9-bromoanthracene (75.0 g), (4-ethoxynaphthalen-1-yl) boronic acid (78.0 g), Pd(dba)$_2$ (5.0 g), tricyclohexyl phosphine (4.9 g), potassium phosphate (124.0 g), and a mixture solvent (440 ml) of pseudo cumene and t-butyl alcohol (pseudo cumene/t-butyl alcohol=10/1 (volume ratio)) were added to a flask and refluxed for 8 hours. The reaction solution was cooled to room temperature and the precipitated solid were collected by suction filtration. The obtained solid was washed with aqueous solution of EDTA.4Na, water, and methanol in order. It was then dissolved in heated chlorobenzene and then subjected to suction filtration by using a Kiriyama funnel layered with silica gel. The crude product obtained by removing filtrate by distillation under reduced pressure was washed with heptane while being heated to give 9-(4-ethoxynaphthalen-1-yl)anthracene (87.1 g) as a fourteenth intermediate compound. The scheme is shown in the following "Reaction 25".

Reaction 25

[Formula 91]

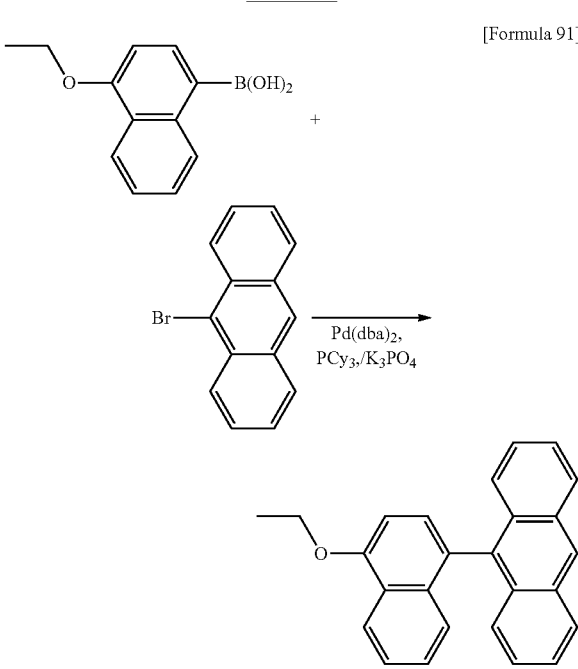

Synthesis of 4-(anthracen-9-yl)naphthalene-1-ol

Under the nitrogen atmosphere, 9-(4-ethoxynaphthalen-1-yl)anthracene (87.1 g) as the fourteenth intermediate compound, pyridine hydrochloride (289.0 g) and 1-methyl-2-pyrrolidone (87 ml) were added to a flask, and stirred for 16 hours at 175° C. The reaction solution was cooled to room temperature, added with water, and washed while being heated. After suction filtration, the solid remained after dissolution was collected. The obtained solid was washed with methanol while being heated. It was then dissolved in heated chlorobenzene and subjected to suction filtration by using a Kiriyama funnel layered with silica gel. An appropriate amount of filtrate was distilled off under reduced pressure, and by adding heptane, re-precipitation was performed to give 4-(anthracen-9-yl)naphthalen-1-ol (74.3 g) as a fifteenth intermediate compound. The scheme is shown in the following "Reaction 26".

Reaction 26

[Formula 92]

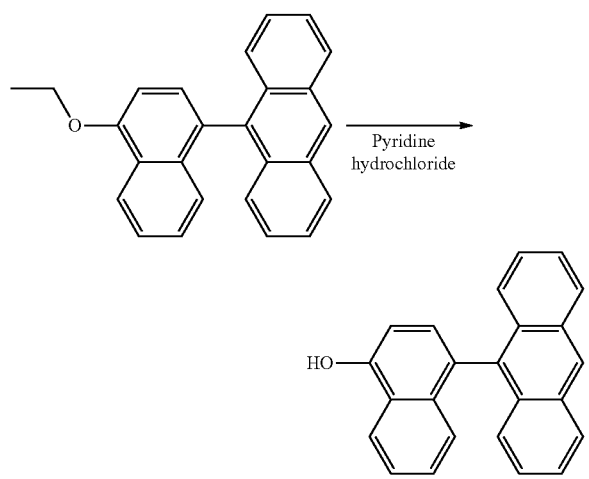

Synthesis of <4-(anthracen-9-yl)naphthalene-1-yl trifluoromethanesulfonate>

Under the nitrogen atmosphere, a flask containing 4-(anthracen-9-yl)naphthalen-1-ol (74.0 g) as the fifteenth intermediate compound and pyridine (500 ml) was cooled in an ice bath, and then added dropwise with trifluoromethane sulfonic acid anhydride (98.0 g). Once the dropwise reaction is completed, it was stirred for 1 hour at room temperature and added with water. The precipitated solid was collected by suction filtration. The obtained solid was washed with methanol, dissolved in toluene, and then subjected to suction filtration by using a Kiriyama funnel layered with silica gel. The crude product obtained by distillation of the filtrate under reduced pressure was re-crystallized with heptane to give 4-(anthracen-9-yl)naphthalen-1-yl trifluoromethane sulfonate (100.2 g) as a sixteenth intermediate compound. The scheme is shown in the following "Reaction 27".

Reaction 27

[Formula 93]

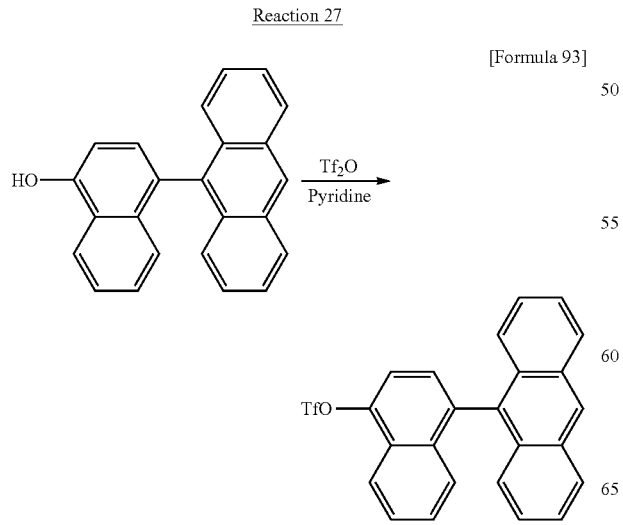

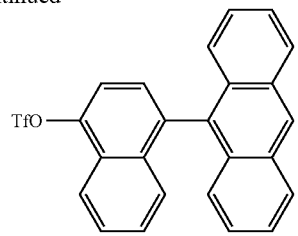

Synthesis of 9-(4-phenylnaphthalene-1-yl)anthracene

Under the nitrogen atmosphere, 4-(anthracen-9-yl)naphthalen-1-yl trifluoromethane sulfonate (30.0 g) as the sixteenth intermediate compound, phenylboronic acid (12.1 g), Pd(PPh$_3$)$_4$ (2.3 g), potassium phosphate (28.1 g), and a mixture solvent of pseudo cumene, t-butyl alcohol, and water (150 ml) (pseudo cumene/t-butyl alcohol/water=8/1/1 (volume ratio)) were added to a flask and refluxed for 5.5 hours. Once the heating is completed, the reaction solution was cooled to room temperature and added with water to terminate the reaction. It was then extracted with toluene. The solvent was distilled off under reduced pressure and purified by silica gel column chromatography (solvent: heptane/toluene mixture solvent). At that time, with reference to the method described in "Guideline for Experiments of Organic Chemistry (1)—Method of handling substance and separation and purification method"—published by Kagaku-Dojin Publishing Company, INC., page 94, the target compound was eluted by gradually increasing the ratio of toluene in the eluent. The crude product obtained by removing the solvent by distillation under reduced pressure was washed with heptane, followed with methanol to give 9-(4-phenylnaphthalen-1-yl)anthracene (24.1 g) as a seventeenth intermediate compound. The scheme is shown in the following "Reaction 28".

Reaction 28

[Formula 94]

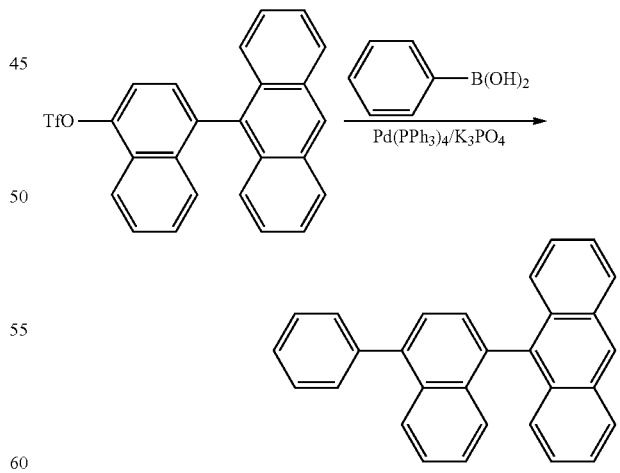

Synthesis of 9-bromo-10-(4-phenylnaphthyl-1-yl)anthracene

Under the nitrogen atmosphere, 9-(4-phenylnaphthalen-1-yl)anthracene (24.0 g) as the seventeenth intermediate compound, N-bromosuccinimide (NBS) (13.5 g), iodine (0.1 g) and THF (200 ml) were added to a flask and stirred for 3.5 hours at room temperature. By adding an aqueous solution of sodium thiosulfate, the reaction was terminated. Extraction was performed using ethyl acetate. Subsequently, the solvent was distilled off under reduced pressure and the solid precipitated during distillation was collected by suction filtration. The obtained crude product was washed with methanol to give 9-bromo-10-(4-phenylnaphthyl-1-yl)anthracene (26.2 g) as an eighteenth intermediate compound. The scheme is shown in the following "Reaction 29".

column (solvent: toluene) to remove the colored components. The solvent was distilled off under reduced pressure, and by adding ethanol to the obtained oily phase substance, re-precipitation was performed to give 4,4,5,5-tetramethyl-2-(10-(4-phenylnaphthalen-1-yl)anthracen-9-yl)-1,3,2-dioxaborolane (26.6 g) as a nineteenth intermediate compound. The scheme is shown in the following "Reaction 30".

Reaction 29

[Formula 95]

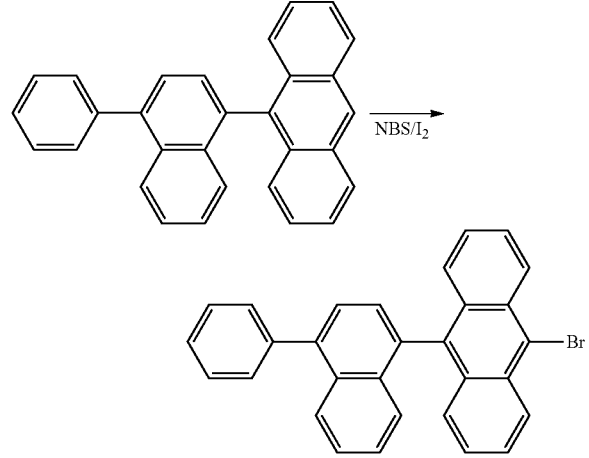

Reaction 30

[Formula 96]

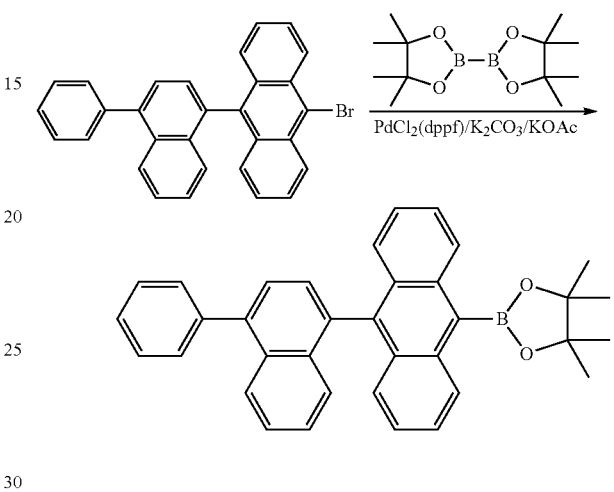

Synthesis of 4,4,5,5-tetramethyl-2-(10-(4-phenyl-naphthalene-1-yl)anthracen-9-yl)-1,3,2-dioxaborolan Under the nitrogen atmosphere, 9-bromo-10-(4-phenyl-naphthyl-1-yl)anthracene (26.0 g) as the eighteenth intermediate compound, bispinacolate diborone (17.3 g), PdCl$_2$(dppf) (1.4 g), potassium carbonate (15.6 g), potassium acetate (11.1 g) and cyclopentyl methyl ether (200 ml) were added to a flask and refluxed for 5 hours. After cooling to room temperature, the reaction solution was added with toluene to dissolve those other than inorganic salts, which were then removed by suction filtration. The solvent was distilled off under reduced pressure, and the obtained solid was washed with heptane and purified with a silica gel short Synthesis of 2-(10-([2,2'-binaphthalene]-7-yl)anthracen-9-yl)triphenylene Under the nitrogen atmosphere, 4,4,5,5-tetramethyl-2-(10-(4-phenylnaphthalen-1-yl)anthracen-9-yl)-1,3,2-dioxaborolane (3.0 g) as the nineteenth compound, [2,2'-binaphthalen]-7-yl trifluoromethane sulfonate (2.6 g), Pd(PPh$_3$)$_4$ (0.3 g), potassium phosphate (2.5 g), and a mixture solvent (26 ml) of toluene, ethanol, and water (toluene/ethanol/water=8/4/1 (volume ratio)) were added to a flask and refluxed for 2 hours. Once the heating is completed, the reaction solution was cooled to room temperature. Liquid separation was performed by adding water and toluene. The solvent was distilled off under reduced pressure and the resulting solid was purified by silica gel column chromatography (solvent: heptane/toluene=4/1). The obtained crude product was washed with ethyl acetate to give 9-([2,2'-binaphthalen]-7-yl)-10-(4-phenylnaphthalen-1-yl)anthracene (1.7 g) as the target compound represented by Formula (1-172). The scheme is shown in the following "Reaction 31".

Reaction 31

[Formula 97]

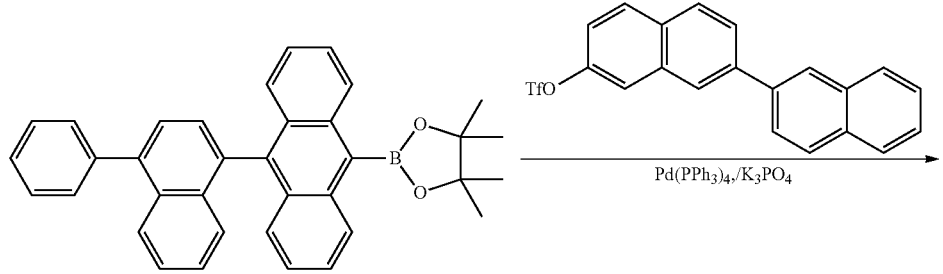

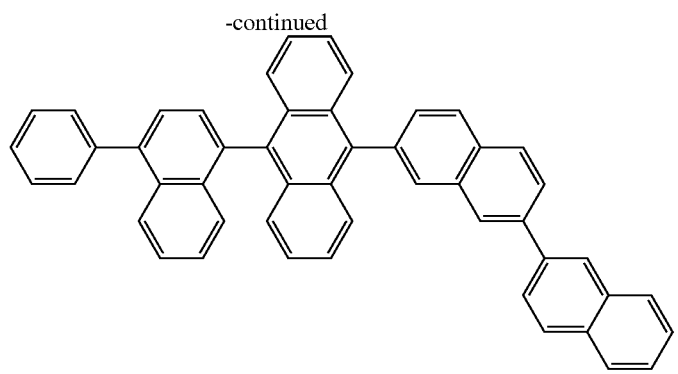

According to NMR measurement, structure of the target compound (1-172) was determined.

$^1$H-NMR (CDCl$_3$): δ=8.28 (d, 1H), 8.24 (s, 1H), 8.13-8.20 (m, 3H), 8.10 (d, 1H), 8.04 (d, 1H), 7.88-8.02 (m, 4H), 7.84 (d, 2H), 7.65-7.76 (m, 5H), 7.49-7.62 (m, 7H), 7.45 (m, 1H), 7.25-7.37 (m, 6H).

Synthetic Example of Compounds Represented by the Formula (1-184)

[Formula 98]

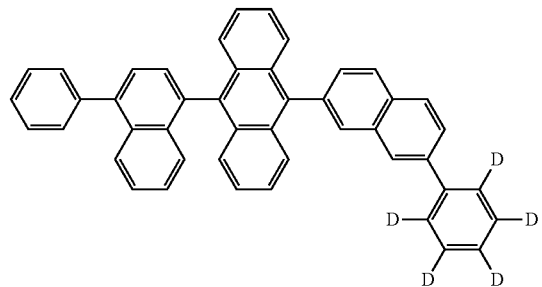

(1-184)

Synthesis of 9-(7-methoxynaphthalene-2-yl)-10-(4-phenylnaphthalene-1-yl)anthracene Under the nitrogen atmosphere, 4,4,5,5-tetramethyl-2-(10-(4-phenylnaphthalen-1-yl)anthracen-9-yl)-1,3,2-dioxaborolane (23.0 g) as the nineteenth intermediate compound, 7-methoxynaphthalen-2-yl trifluoromethane sulfonate (18.0 g), Pd(PPh$_3$)$_4$ (1.6 g), potassium phosphate (19.3 g), and a mixture solvent (125 ml) of pseudo cumene, IPA, and water (pseudo cumene/IPA/water=20/4/1 (volume ratio)) were added to a flask and refluxed for 5 hours. Once the heating is completed, liquid separation was performed by adding water and toluene. The solvent was distilled off under reduced pressure and the resulting solid was purified by silica gel column chromatography (solvent: heptane/toluene=1/1). The obtained crude product was washed further with methanol to give 9-(7-methoxynaphthalen-2-yl)-10-(4-phenylnaphthalen-1-yl)anthracene (16.3 g) as a twentieth intermediate compound. The scheme is shown in the following "Reaction 32".

Reaction 32

[Formula 99]

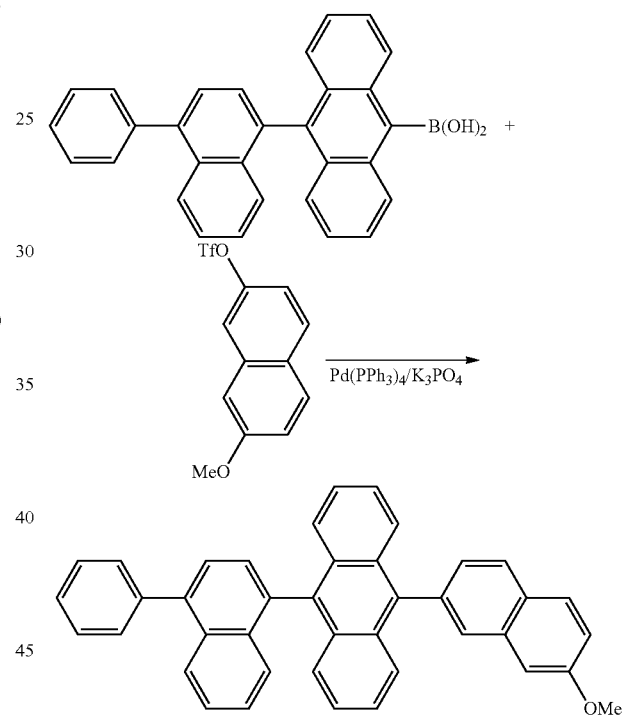

Synthesis of 7-(10-(4-phenylnaphthalene-1-yl)anthracen-9-yl)naphthalene-2-ol

Under the nitrogen atmosphere, 9-(7-methoxynaphthalen-2-yl)-10-(4-phenylnaphthalen-1-yl)anthracene (16.0 g) as the twentieth intermediate compound, pyridine hydrochloride (17.3 g) and N-methylpyrrolidone (30 ml) were added to a flask and stirred for 8 hours at 200° C. Once the heating is completed, the mixture was cooled to 100° C. or lower. Liquid separation was performed by adding water and toluene. The solvent was distilled off under reduced pressure and the resulting solid was purified by silica gel column chromatography (solvent: toluene) to give 7-(10-(4-phenylnaphthalen-1-yl)anthracen-9-yl)naphthalen-2-ol (15.5 g) as a twenty-first intermediate compound. The scheme is shown in the following "Reaction 33".

Reaction 33

[Formula 100]

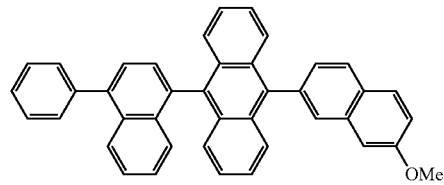

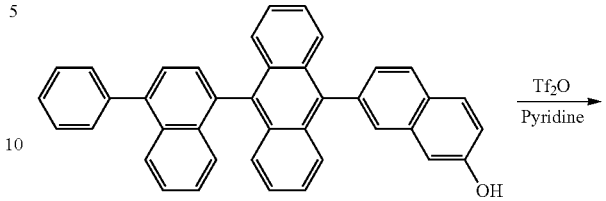

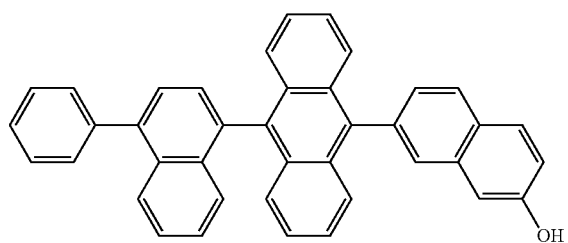

Synthesis of <7-(10-(4-phenylnaphthalene-1-yl)anthracen-9-yl)naphthalene-2-yl trifluoromethanesulfonate>

Under the nitrogen atmosphere, 7-(10-(4-phenylnaphthalen-1-yl)anthracen-9-yl)naphthalen-2-ol (15.5 g) as the twenty-first intermediate compound and pyridine (100 ml) were added to a flask, cooled to 0° C., and then gradually added dropwise with trifluoromethane sulfonic acid anhydride (16.9 g). After that, it was stirred for 3 hours at room temperature and again cooled to 0° C. The reaction was terminated by adding water and the target component was extracted with toluene. The organic layer was concentrated under reduced pressure and then purified by silica gel column chromatography (solvent: toluene). The obtained crude product was washed again with heptane to give 7-(10-(4-phenylnaphthalen-1-yl)anthracen-9-yl)naphthalen-2-yl trifluoromethane sulfonate (16.2 g) as a twenty-second intermediate compound. The scheme is shown in the following "Reaction 34".

Reaction 34

[Formula 101]

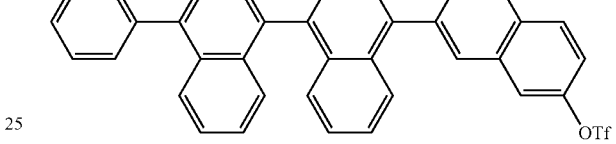

Synthesis of 9-(4-phenylnaphthalene-1-yl)-10-(7-([2,3,4,5,6-$^2$H$_5$]phenyl)naphthalene-2-yl)anthracene Under the nitrogen atmosphere, 7-(10-(4-phenylnaphthalen-1-yl)anthracen-9-yl)naphthalen-2-yl trifluoromethane sulfonate (3.5 g) as the twenty-second intermediate compound, [2,3,4,5,6-$^2$H$_5$]phenylboronic acid (1.0 g), bis(dibenzylideneacetone)palladium (0) (Pd(dba)$_2$) (0.03 g), tricyclohexyl phosphine (PCy$_3$) (0.03 g), potassium phosphate (2.3 g), and a mixture solvent (22 ml) of toluene, ethanol, and water (toluene/ethanol/water=9/1/1 (volume ratio)) were added to a flask and then refluxed for 3 hours. Once the heating is completed, the reaction solution was cooled to room temperature. Liquid separation was performed by adding water and toluene. The solvent was distilled off under reduced pressure and the resultant was purified by silica gel column chromatography (solvent: heptane/toluene=3/1 (volume ratio)) to give 9-(4-phenylnaphthalen-1-yl)-10-(7-([2,3,4,5,6-$^2$H$_5$]phenyl) naphthalen-2-yl)anthracene (1.7 g) as the target compound represented by Formula (1-184). The scheme is shown in the following "Reaction 35".

Reaction 35

[Formula 102]

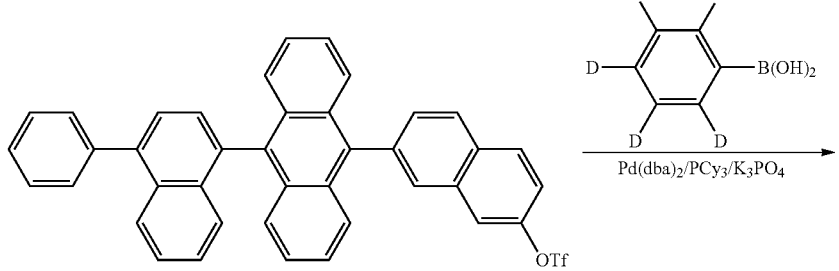

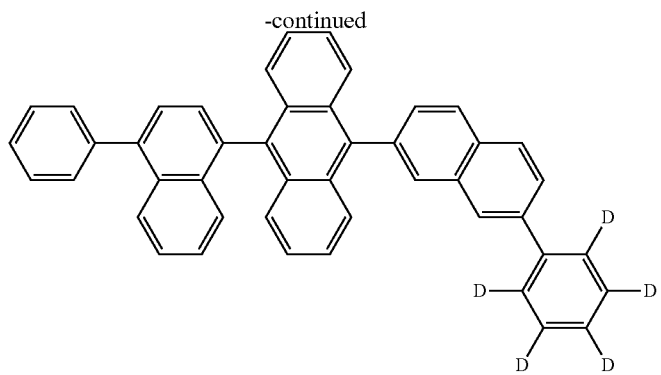

According to NMR measurement, structure of the target compound (1-184) was determined.

$^1$H-NMR (CDCl$_3$): δ=8.08-8.16 (m, 5H), 7.89 (d, 1H), 7.82 (d, 2H), 7.64-7.73 (m, 5H), 7.56-7.61 (m, 4H), 7.51 (t, 1H), 7.44 (t, 1H), 7.23-7.35 (m, 6H).

Herein after, examples of an organic EL element using the compound of the invention are given to describe the invention in greater detail. However, the invention is not limited to them.

Elements according to Example 1 and Comparative example 1 were prepared, and each of them was subjected to a constant current driving test at current density set to have luminance of 2000 cd/m² and the voltage for driving initiation (V) and the time (hours) during which luminance is maintained at the level of 80% (1600 cd/m²) or more of the initial luminance were measured. Detailed explanations are given in the following Examples and Comparative examples.

Material constitution of each layer in the organic EL elements which have been fabricated in Example 1 and Comparative example 1 is represented in the following Table 1.

TABLE 1

| | Hole Injection Layer | Hole Transport Layer | light Emitting layer (25 nm) | | Electron Transport Layer | Negative Electrode |
|---|---|---|---|---|---|---|
| | (40 nm) | (25 nm) | Host | Dorpant | (25 nm) | (1 nm/100 nm) |
| Example 1 | HI | NPD | Compound (1-2) | BD1 | ET1 + Liq | Liq/Al |
| Comparative Example 1 | HI | NPD | BH1 | BD1 | ET1 + Liq | Liq/Al |

In Table 1, "HI" indicates N$^4$,N$^{4'}$-diphenyl-N$^4$,N$^{4'}$-bis(9-phenyl-9H-carbazol-3-yl)-[1,1'-biphenyl]-4,4'-diamine, "NPD" indicates N,N'-diphenyl-N,N'-dinaphthyl-4,4'-diaminobiphenyl, "BH1" indicates 9-(6-([1,1'-biphenyl]-3-yl)naphthalen-2-yl)-10-phenylanthracene, "BD1" indicates 7,7,N$^5$,N$^9$-tetraphenyl-N$^5$,N$^9$-bis-(4-trimethylsilanyl-phenyl)-7H-benzo[c]fluorene-5,9-diamine, "ET1" indicates 2-(4-(9,10-di(naphthalen-2-yl)anthracen-2-yl)-phenyl)-1-phenyl-1H-benzo[d]imidazole, and "Liq" indicates 8-quinolinol lithium. Chemical structures are represented below.

[Formula 103]

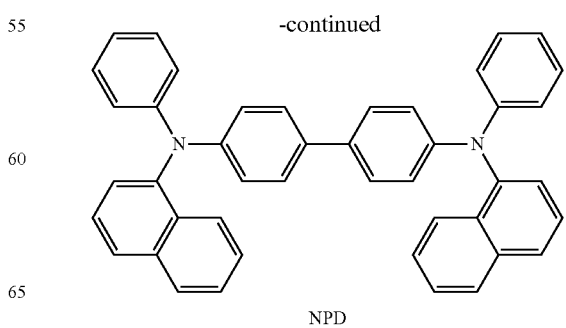

-continued

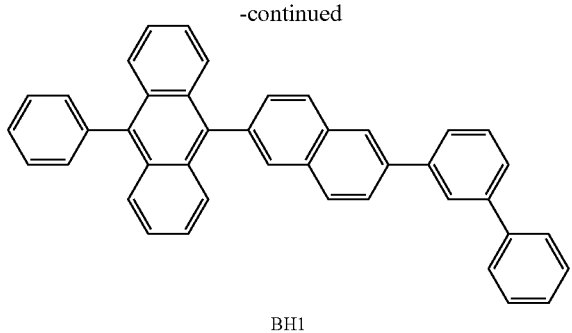

BH1

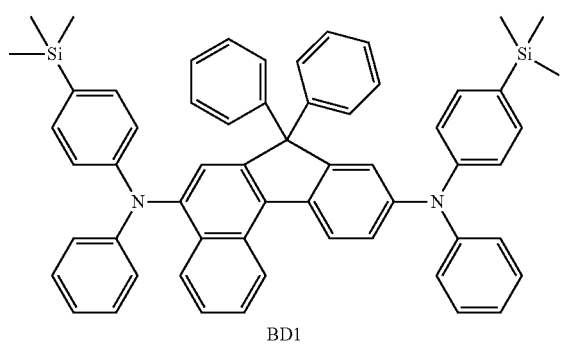

BD1

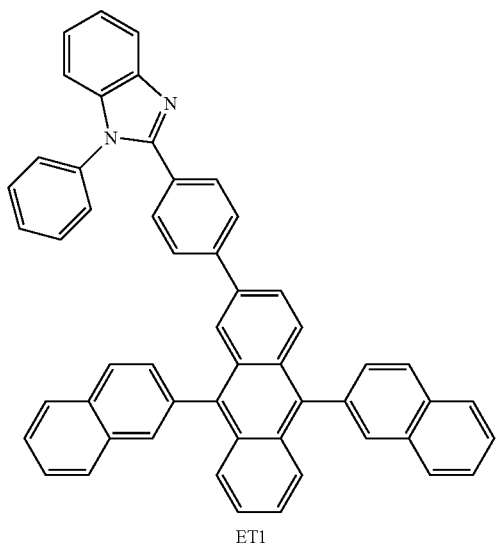

ET1

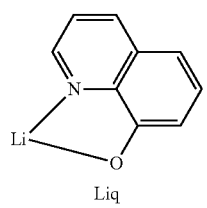

Liq

Example 1

Element Using the Compound (1-2) as Host Material of Light Emitting Layer

ITO was deposited as a film with a thickness of 180 nm by sputtering onto a glass substrate (26 mm×28 mm×0.7 mm, manufactured by Opto Science, Inc.) and polished to a thickness of 150 nm to give a transparent supporting substrate. The transparent supporting substrate was fixed on a substrate holder of a commercially available deposition device (manufactured by Showa Shinku Co., Ltd.), and loaded therein were a molybdenum-made boat for deposition added with HI, a molybdenum-made boat for deposition added with NPD, a molybdenum-made boat for deposition added with the compound (1-2) of the invention, a molybdenum-made boat for deposition added with BD1, a molybdenum-made boat for deposition added with ET1, a molybdenum-made boat for deposition added with Liq, and a tungsten-made boat for deposition added with aluminum.

The respective layers described below were formed in order on the ITO film of the transparent supporting substrate. A vacuum chamber was reduced in pressure down to $5 \times 10^{-4}$ Pa, and the boat for deposition containing HI was first heated to deposit it in a layer thickness of 40 nm, whereby a hole injection layer was formed. Then, the boat for deposition containing NPD was heated to deposit it in a layer thickness of 25 nm, whereby a hole transport layer was formed. Next, the boat for deposition containing the compound (1-2) and the boat for deposition containing BD1 were heated at the same time to deposit them in a layer thickness of 25 nm, whereby a light emitting layer was formed. The deposit rate was controlled so that a weight ratio of the compound (1-2) to BD1 was approximately 95 to 5. Then, the boat for deposition containing ET1 and the boat for deposition containing Liq were simultaneously heated to deposit it in a layer thickness of 25 nm, whereby an electron transport layer was formed. The deposit rate was controlled so that a weight ratio of the ET1 to Liq was approximately 1 to 1. The deposit rates of the respective layers were 0.01 to 1 nm/second.

Thereafter, the boat for deposition containing Liq was heated to deposit it at a deposit rate of 0.01 to 0.1 nm/second so that a layer thickness was 1 nm, and then the boat for deposition containing aluminum was heated to deposit it at a deposit rate of 0.01 to 2 nm/second so that a layer thickness was 100 nm, whereby a negative electrode was formed. Thus, an organic EL element was obtained.

With the ITO electrode set to a positive electrode and the Liq/aluminum electrode set to a negative electrode, blue light emission with wavelength of about 460 nm was obtained when direct voltage was applied. Further, when the constant current driving test was performed at current density set to have initial luminance of 2000 cd/m$^2$, the voltage for driving initiation was 4.16 V and the time during which luminance is maintained at the level of 80% (1600 cd/m$^2$) or more of the initial luminance was 720 hours.

Comparative Example 1

The organic EL element was obtained in the same manner as Example 1 except that the compound (1-2) as a host material of the light emitting layer is replaced with BH1. With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.34 V and the time during which luminance is maintained at the level of 80% (1600 cd/m$^2$) or more of the initial luminance was 455 hours.

The above results are summarized in Table 2.

TABLE 2

| | Host Material | Driving Voltage (V) at 2000 cd/m$^2$ | Time during luminance is maintained at level of 80% or more of the initial luminance (hour) |
|---|---|---|---|
| Example 1 | Compound (1-2) | 4.16 | 720 |
| Comparative Example 1 | BH1 | 4.34 | 455 |

Next, the elements according to Examples 2 to 11 and Comparative examples 2 to 4 were fabricated, and for the constant current driving test performed at current density set to have luminance of 2000 cd/m$^2$, the voltage for driving initiation (V) and the time (hours) during which luminance is maintained at the level of 80% (1600 cd/m$^2$) or more of the initial luminance were measured for each element. Detailed explanations are given in the following Examples and Comparative examples.

Material constitution of each layer in the organic EL elements which have been fabricated in Examples 2 to 11 and Comparative examples 2 to 4 is represented in the following Table 3.

TABLE 3

| | Hole Injection Layer (40 nm) | Hole Transport Layer (25 nm) | light Emitting layer (25 nm) | | Electron Transport Layer (20 nm) | Negative Electrode (1 nm/100 nm) |
|---|---|---|---|---|---|---|
| | | | Host | Dorpant | | |
| Example 2 | HI | NPD | Compound (1-1) | BD2 | ET2 | Liq/Mg + Ag |
| Example 3 | HI | NPD | Compound (1-34) | BD2 | ET2 | Liq/Mg + Ag |
| Example 4 | HI | NPD | Compound (1-21) | BD2 | ET2 | Liq/Mg + Ag |
| Example 5 | HI | NPD | Compound (1-38) | BD2 | ET2 | Liq/Mg + Ag |
| Example 6 | HI | NPD | Compound (1-160) | BD2 | ET2 | Liq/Mg + Ag |
| Example 7 | HI | NPD | Compound (1-162) | BD2 | ET2 | Liq/Mg + Ag |
| Example 8 | HI | NPD | Compound (1-164) | BD2 | ET2 | Liq/Mg + Ag |
| Example 9 | HI | NPD | Compound (1-172) | BD2 | ET2 | Liq/Mg + Ag |
| Example 10 | HI | NPD | Compound (1-117) | BD2 | ET2 | Liq/Mg + Ag |
| Example 11 | HI | NPD | Compound (1-184) | BD2 | ET2 | Liq/Mg + Ag |
| Comparative Example 2 | HI | NPD | BH1 | BD2 | ET2 | Liq/Mg + Ag |
| Comparative Example 3 | HI | NPD | BH2 | BD2 | ET2 | Liq/Mg + Ag |
| Comparative Example 4 | HI | NPD | BH3 | BD2 | ET2 | Liq/Mg + Ag |

In Table 3, "BD2" indicates 7,7-dimethyl-$N^5,N^9$-diphenyl-$N^5,N^9$-bis-(4-trimethylsilanyl-phenyl)-7H-benzo [c] fluorene-5,9-diamine, "ET2" indicates 4,4'-((2-phenylanthracen-9,10-diyl)bis(4,1-phenylene))dipyridine, "BH2" indicates 9-([2,2'-binaphthalen]-6-yl)-10-phenylanthracene, and "BH3" indicates 9-phenyl-10-(6-phenylnaphthalen-2-yl)anthracene.

Chemical structures are represented below.

[Formula 104]

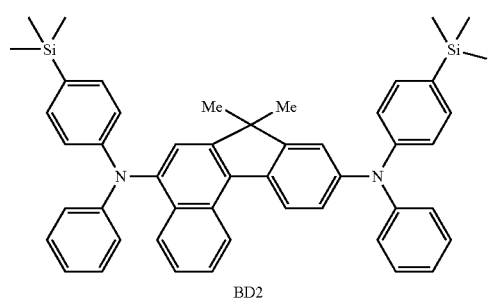

BD2

TABLE 3-continued

| Hole Injection Layer | Hole Transport Layer | light Emitting layer (25 nm) | | Electron Transport Layer | Negative Electrode |
|---|---|---|---|---|---|
| (40 nm) | (25 nm) | Host | Dorpant | (20 nm) | (1 nm/100 nm) |

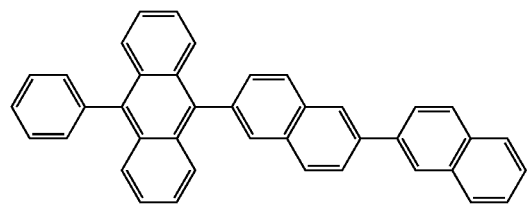

BH2

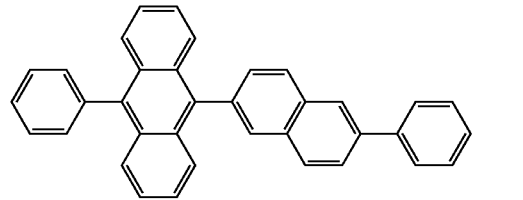

BH3

Example 2

Element Using the Compound (1-1) as Host Material of Light Emitting Layer

ITO was deposited as a film with a thickness of 180 nm by sputtering onto a glass substrate (26 mm×28 mm×0.7 mm, manufactured by Opto Science, Inc.) and polished to a thickness of 150 nm to give a transparent supporting substrate. The transparent supporting substrate was fixed on a substrate holder of a commercially available deposition device (manufactured by Showa Shinku Co., Ltd.), and loaded therein were a molybdenum-made boat for deposition added with HI, a molybdenum-made boat for deposition added with NPD, a molybdenum-made boat for deposition added with the compound (1-1) of the invention, a molybdenum-made boat for deposition added with BD2, a molybdenum-made boat for deposition added with ET2, a molybdenum-made boat for deposition added with Liq, a molybdenum-made boat for deposition added with magnesium, and a tungsten-made boat for deposition added with silver.

The respective layers described below were formed in order on the ITO film of the transparent supporting substrate. A vacuum chamber was reduced in pressure down to 5×10$^{-4}$ Pa, and the boat for deposition containing HI was first heated to deposit it in a layer thickness of 40 nm, whereby a hole injection layer was formed. Then, the boat for deposition containing NPD was heated to deposit it in a layer thickness of 25 nm, whereby a hole transport layer was formed. Next, the boat for deposition containing the compound (1-1) and the boat for deposition containing BD2 were heated at the same time to deposit them in a layer thickness of 25 nm, whereby an light emitting layer was formed. The deposit rate was controlled so that a weight ratio of the compound (1-1) to BD2 was approximately 95 to 5. Then, the boat for deposition containing ET2 was heated to deposit it in a layer thickness of 20 nm, whereby an electron transport layer was formed. The deposit rates of the respective layers were 0.01 to 1 nm/second.

After that, the boat for deposition containing Liq was heated to deposit it in a layer thickness of 1 nm. The deposit rate of the respective layer was 0.01 to 0.1 nm/second. Subsequently, the boat containing magnesium and the boat containing silver were simultaneously heated to deposit them in a layer thickness of 100 nm, and thus the negative electrode was formed. At that time, the deposit rate was controlled so that the ratio of the number of atoms of magnesium to silver was approximately 10 to 1, and the negative electrode was formed such that the deposit rate is 0.1 to 10 nm/second. As a result, an organic electroluminescence element was obtained.

With the ITO electrode set to a positive electrode and the magnesium/silver electrode set to a negative electrode, blue light emission with wavelength of about 460 nm was obtained when direct voltage was applied. Further, when the constant current driving test was performed at current density set to have initial luminance of 2000 cd/m$^2$, the voltage for driving test initiation was 4.03 V and the time during which luminance is maintained at the level of 80% (1600 cd/m$^2$) or more of the initial luminance was 235 hours.

Example 3

The organic EL element was obtained in the same manner as Example 2 except that the compound (1-1) as a host material of the light emitting layer is replaced with the compound (1-34). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 3.93 V and the time during which luminance is maintained at the level of 80% (1600 cd/m$^2$) or more of the initial luminance was 276 hours.

Example 4

The organic EL element was obtained in the same manner as Example 2 except that the compound (1-1) as a host material of the light emitting layer is replaced with the compound (1-21). With the ITO electrode set to a positive electrode and the Liq/aluminum electrode set to a negative electrode, the constant current driving test was performed at current density set to have initial luminance of 2000 cd/m$^2$. As a result, the

Example 5

The organic EL element was obtained in the same manner as Example 2 except that the compound (1-1) as a host material of the light emitting layer is replaced with the compound (1-38). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 3.70 V and the time during which luminance is maintained at the level of 80% (1600 cd/m$^2$) or more of the initial luminance was 235 hours.

Example 6

The organic EL element was obtained in the same manner as Example 2 except that the compound (1-1) as a host material of the light emitting layer is replaced with the compound (1-160). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 3.98 V and the time during which luminance is maintained at the level of 80% (1600 cd/m$^2$) or more of the initial luminance was 228 hours.

Example 7

The organic EL element was obtained in the same manner as Example 2 except that the compound (1-1) as a host material of the light emitting layer is replaced with the compound (1-162). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.15 V and the time during which luminance is maintained at the level of 80% (1600 cd/m$^2$) or more of the initial luminance was 263 hours.

Example 8

The organic EL element was obtained in the same manner as Example 2 except that the compound (1-1) as a host material of the light emitting layer is replaced with the compound (1-164). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 3.67 V and the time during which luminance is maintained at the level of 80% (1600 cd/m$^2$) or more of the initial luminance was 271 hours.

Example 9

The organic EL element was obtained in the same manner as Example 2 except that the compound (1-1) as a host material of the light emitting layer is replaced with the compound (1-172). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 3.82 V and the time during which luminance is maintained at the level of 80% (1600 cd/m$^2$) or more of the initial luminance was 261 hours.

Example 10

The organic EL element was obtained in the same manner as Example 2 except that the compound (1-1) as a host material of the light emitting layer is replaced with the compound (1-117). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.30 V and the time during which luminance is maintained at the level of 80% (1600 cd/m$^2$) or more of the initial luminance was 275 hours.

Example 11

The organic EL element was obtained in the same manner as Example 2 except that the compound (1-1) as a host material of the light emitting layer is replaced with the compound (1-184). With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.21V and the time during which luminance is maintained at the level of 80% (1600 cd/m$^2$) or more of the initial luminance was 231 hours.

Comparative Example 2

The organic EL element was obtained in the same manner as Example 2 except that the compound (1-1) as a host material of the light emitting layer is replaced with the BH1. With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.78 V and the time during which luminance is maintained at the level of 80% (1600 cd/m$^2$) or more of the initial luminance was 178 hours.

Comparative Example 3

The organic EL element was obtained in the same manner as Example 2 except that the compound (1-1) as a host material of the light emitting layer is replaced with the BH2. With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.35 V and the time during which luminance is maintained at the level of 80% (1600 cd/m$^2$) or more of the initial luminance was 189 hours.

Comparative Example 4

The organic EL element was obtained in the same manner as Example 2 except that the compound (1-1) as a host material of the light emitting layer is replaced with the BH3. With the ITO electrode set to a positive electrode and the Liq/aluminum electrode set to a negative electrode, the constant current driving test was performed at current density set to have initial luminance of 2000 cd/m$^2$. As a result, the voltage for driving test initiation was 4.64 V and the time during which luminance is maintained at the level of 80% (1600 cd/m$^2$) or more of the initial luminance was 171 hours.

The above results are summarized in Table 4.

TABLE 4

| | Host Material | Driving Voltage (V) at 2000 cd/m² | Time during luminance is maintained at level of 80% or more of the initial luminance (hour) |
|---|---|---|---|
| Example 2 | Compound (1-1) | 4.03 | 235 |
| Example 3 | Compound (1-34) | 3.93 | 276 |
| Example 4 | Compound (1-21) | 4.03 | 265 |
| Example 5 | Compound (1-38) | 3.70 | 235 |
| Example 6 | Compound (1-160) | 3.98 | 228 |
| Example 7 | Compound (1-162) | 4.15 | 263 |
| Example 8 | Compound (1-164) | 3.67 | 271 |
| Example 9 | Compound (1-172) | 3.82 | 261 |
| Example 10 | Compound (1-117) | 4.30 | 275 |
| Example 11 | Compound (1-184) | 4.21 | 231 |
| Comparative Example 2 | BH1 | 4.78 | 178 |
| Comparative Example 3 | BH2 | 4.35 | 189 |
| Comparative Example 4 | BH3 | 4.64 | 171 |

INDUSTRIAL APPLICABILITY

According to the preferred embodiment of the invention, capable of being provided are an organic electroluminescence element having excellent light emission efficiency and element service life, a display device equipped with the same, a lighting device equipped with the same and the like.

REFERENCE SIGNS LIST

100 organic electroluminescence element
101 substrate
102 positive electrode
103 hole injection layer
104 hole transport layer
105 light emitting layer
106 electron transport layer
107 electron injection layer
108 negative electrode

The invention claimed is:

1. A compound represented by the following Formula (1)

[Formula 1]

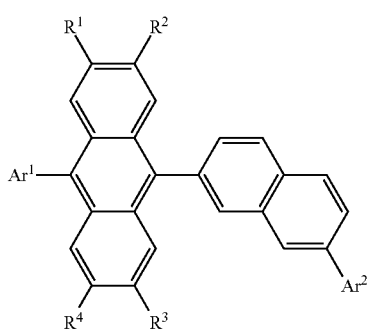

(1)

In formula (1),
$Ar^1$ is an aryl having 10-30 carbon atoms which may be substituted,
$Ar^2$ is an aryl having 6-30 carbon atoms which may be substituted,
$R^1$-$R^4$ are, each independently, a hydrogen or an alkyl having 1-4 carbon atoms, and
at least one hydrogen in the compound represented by the formula (1) may be substituted with deuterium.

2. The compound according to claim 1, in which
$Ar^1$ is naphthyl, biphenylyl, binaphthyl, terphenylyl, quaterphenylyl, naphthylphenyl, phenylnaphthyl, phenanthryl, phenanthrylphenyl, chrysenyl, pyrenylphenyl, or triphenylenyl, which may be substituted with alkyl having 1-12 carbon atoms, or cycloalkyl having 3-12 carbon atoms,
$Ar^2$ is phenyl, naphthyl, biphenylyl, binaphthyl, terphenylyl, quaterphenylyl, naphthylphenyl, phenylnaphthyl, phenanthryl, phenanthrylphenyl, chrysenyl, pyrenylphenyl, or triphenylenyl, which may be substituted with alkyl having 1-12 carbon atoms, or cycloalkyl having 3-12 carbon atoms,
$R^1$-$R^4$ are, each independently, hydrogen, methyl, isopropyl, or t-butyl, and
at least one hydrogen in compounds represented by the formula (1) may be substituted with deuterium.

3. The compound according to claim 1, in which
$Ar^1$ is 1-naphthyl, 2-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl,
$Ar^2$ is phenyl, 1-naphthyl, 2-naphthyl, 2-biphenylyl, 3-biphenylyl, 4-biphenylyl, m-terphenyl-5'-yl, 4-(naphthalene-1-yl)phenyl, 4-(naphthalene-2-yl)phenyl, phenanthrene-9-yl or triphenylene-2-yl,
$R^1$-$R^4$ are hydrogen, and
at least one hydrogen in the compound represented by the formula (1) may be substituted with deuterium.

4. The compound according to claim 3, in which $Ar^1$ is 1-naphthyl, 2-biphenylyl, 3-biphenylyl, 4-biphenylyl, 4-phenyl-1-naphthyl, m-terphenyl-5'-yl, phenanthrene-9-yl, or triphenylene-2-yl, and
at least one hydrogen in $Ar^2$ may be substituted with deuterium.

5. The compound represented by the following formula (1-2).

[Formula 2]

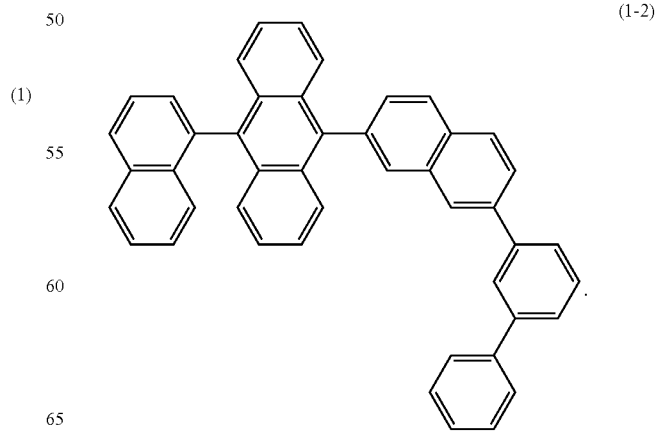

(1-2)

6. Compounds represented by the following formula (1-1), formula (1-21), formula (1-34), formula (1-38), formula (1-117), or formula (1-129).
[Formula 3]
(1-1)
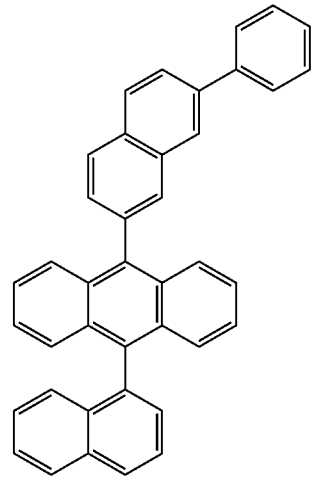
(1-21)
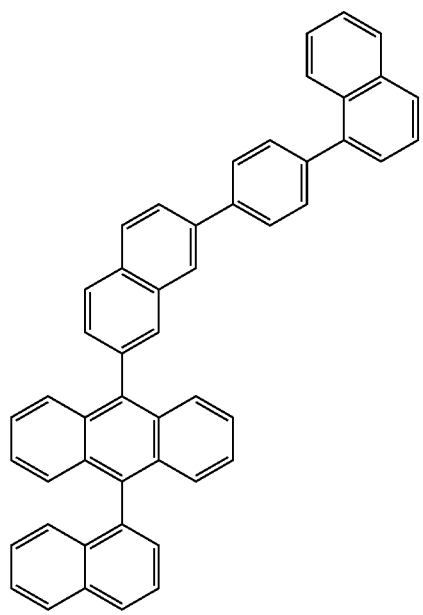
(1-34)
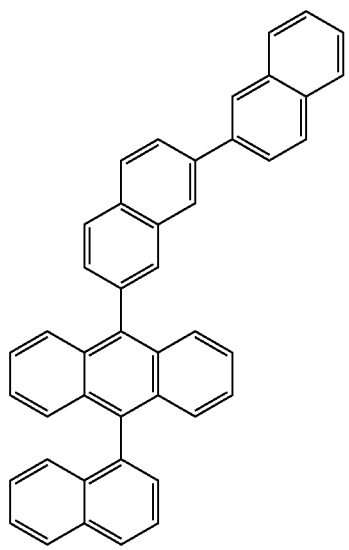
(1-38)
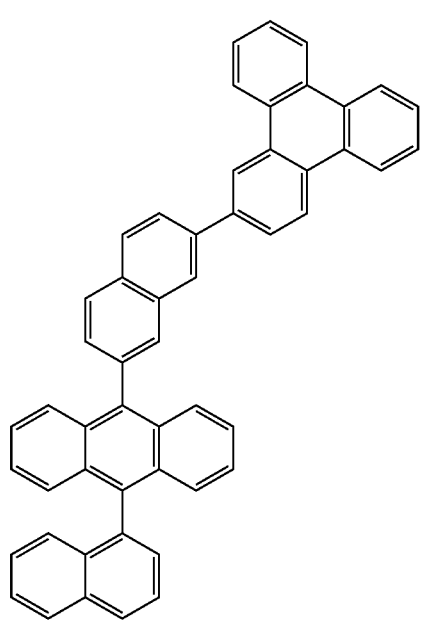

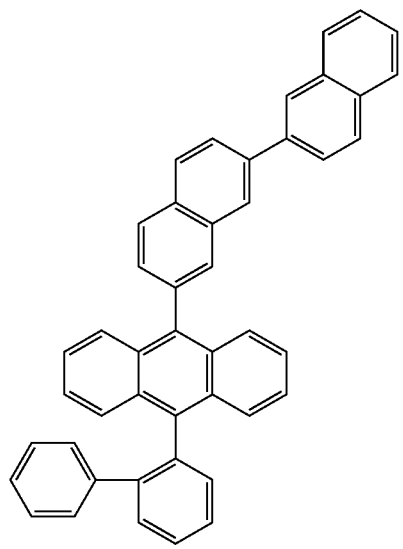
(1-117)
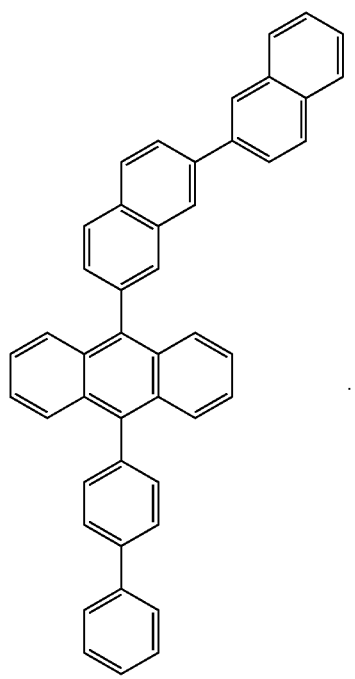
(1-129)
7. Compounds represented by the following formula (1-160), formula (1-162), formula (1-164), formula (1-166), formula (1-172), or the formula (1-184).
[Formula 4]
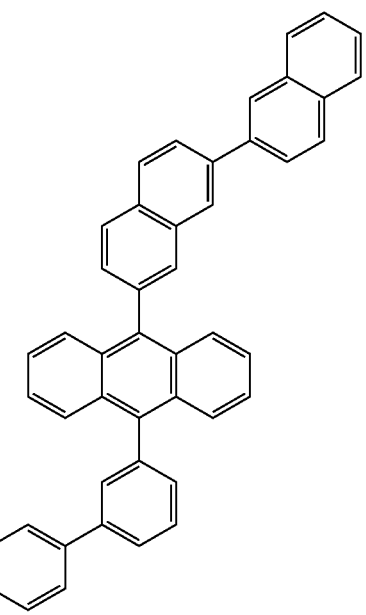
(1-160)
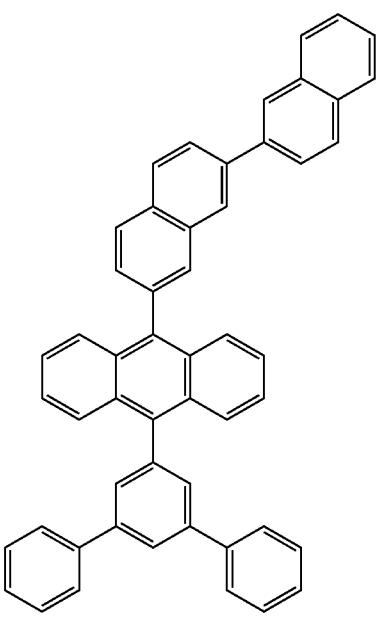
(1-162)

(1-164)

(1-166)

(1-172)

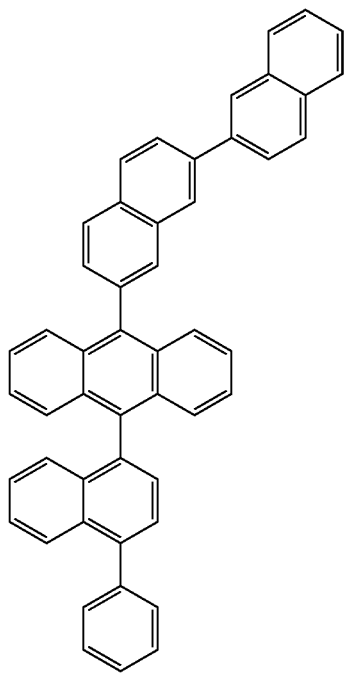

(1-184)

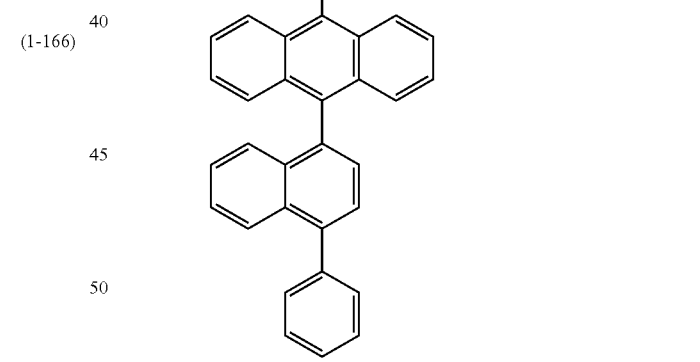

8. A light emitting layer material represented by the compound according to claim 1.

9. An organic electroluminescence element having a pair of electrodes consisting of a positive electrode and a negative electrode and a light emitting layer containing the light emitting layer material according to claim 8 as disposed between the pair of electrodes.

10. The organic electroluminescence element according to claim 9, which has in the light emitting layer at least one selected from the group consisting of amine with a stilbene structure, an aromatic amine derivative, and a coumarin derivative.

11. The organic electroluminescence element according to claim 9, which has an electron transport layer and/or an electron injection layer disposed between the negative electrode and the light emitting layer, in which at least one of the electron transport layer and the electron injection layer contains at least one selected from the group consisting of a quinolinol-based metal complex, a pyridine derivative, a phenanthroline derivative, a borane derivative, and a benzimidazole derivative.

12. The organic electroluminescence element according to claim 11, in which at least one of the electron transport layer and the electron injection layer also contains at least one selected from the group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal.

13. A display device having the organic electroluminescence element according to claim 9.

14. A lighting device having the organic electroluminescence element according to claim 9.

\* \* \* \* \*